(12) United States Patent
Zennadi

(10) Patent No.: US 10,195,204 B2
(45) Date of Patent: Feb. 5, 2019

(54) METHODS OF TREATING HEMOGLOBINOPATHIES

(71) Applicant: DUKE UNIVERSITY, Durham, NC (US)

(72) Inventor: Rahima Zennadi, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 15/428,461

(22) Filed: Feb. 9, 2017

(65) Prior Publication Data

US 2017/0319591 A1 Nov. 9, 2017

Related U.S. Application Data

(62) Division of application No. 14/114,456, filed as application No. PCT/US2012/035837 on Apr. 30, 2012, now Pat. No. 9,592,236.

(60) Provisional application No. 61/480,157, filed on Apr. 28, 2011.

(51) Int. Cl.

| A61K 31/5377 | (2006.01) |
|---|---|
| A61K 31/166 | (2006.01) |
| A61K 31/277 | (2006.01) |
| A61K 31/18 | (2006.01) |
| A61K 31/352 | (2006.01) |
| A61K 31/404 | (2006.01) |
| A61K 31/4412 | (2006.01) |
| A61K 31/444 | (2006.01) |

(52) U.S. Cl.
CPC ........ *A61K 31/5377* (2013.01); *A61K 31/166* (2013.01); *A61K 31/18* (2013.01); *A61K 31/277* (2013.01); *A61K 31/352* (2013.01); *A61K 31/404* (2013.01); *A61K 31/444* (2013.01); *A61K 31/4412* (2013.01)

(58) Field of Classification Search
CPC .... A61K 31/166; A61K 31/18; A61K 31/277; A61K 31/352; A61K 31/404; A61K 31/4412; A61K 31/444; A61K 31/5377
See application file for complete search history.

(56) References Cited

U.S. PATENT DOCUMENTS

| 2001/0027215 A1 | 10/2001 | Perrine |
| 2007/0049591 A1 | 3/2007 | Pinkerton et al. |
| 2009/0285786 A1 | 11/2009 | Zon et al. |

(Continued)

FOREIGN PATENT DOCUMENTS

| WO | WO 02/076496 A1 | 10/2002 |
| WO | WO 02/102232 A2 | 12/2002 |

(Continued)

OTHER PUBLICATIONS

Ballas, S.K. et al., "Red blood cell changes during the evolution of the sickle cell painful crisis," Blood 1992, 79:2154-2163.

(Continued)

*Primary Examiner* — Savitha M Rao
(74) *Attorney, Agent, or Firm* — Andrus Intellectual Property Law, LLP

(57) ABSTRACT

Methods of alleviating the symptoms of hemoglobinopathies, including, but not limited to, sickle cell disease, β-thalassemia, and hemoglobin H disease are provided. In some embodiments, the methods comprise administering an inhibitor selected from an ERK inhibitor, a MEK inhibitor, and, a Raf inhibitor. Methods of inhibiting adhesion of sickle red blood cells to endothelial cells are also provided.

12 Claims, 25 Drawing Sheets

Specification includes a Sequence Listing.

(56) References Cited

U.S. PATENT DOCUMENTS

| | | | |
|---|---|---|---|
| 2010/0286178 | A1 | 11/2010 | Ibrahim et al. |
| 2011/0293558 | A1 | 12/2011 | Suresh et al. |
| 2014/0179700 | A1 | 6/2014 | Zennadi |
| 2015/0265684 | A1 | 9/2015 | Zennadi |

FOREIGN PATENT DOCUMENTS

| | | |
|---|---|---|
| WO | WO 2014/081760 | 5/2014 |
| WO | WO 2015/179855 | 11/2015 |

OTHER PUBLICATIONS

Brunati, A.M. et al., "Sequential phosphorylation of protein band 3 by Syk and Lyn tyrosine kinases in intact human erythrocytes: identification of primary and secondary phosphorylation sites," Blood 2000, 96:1550-1557.

Brzostowski, J.A. et al., "Signaling at zero G: G-protein-independent functions for 7-TM receptors," Trends Biochem Sci 2001, 26:291-297.

Crews, C. et al., "Erks: Their Fifteen Minutes Has Arrived," Cell Growth Differentiation 1992, 3:135-142.

De Castro, L.M. et al., "Effect of propranolol as anti-adhesive therapy in sickle cell disease," (2012) Clin Transl Sci 5(6):437-444.

European Search Report for European Patent Application No. EP12775962.9 dated Sep. 4, 2014 (18 pages).

Fincham, V.J. et al., "Active ERK/MAP kinase is targeted to newly forming cell-matrix adhesions by integrin engagement and v-Src," EMBO Journal 2000, 19:2911-2923.

Frenette, P.S. & Atweh, G.F. "Sickle cell disease: old discoveries, new concepts, and future promise," J Clin Invest 2007, 117:850-858.

George, A. et al, "Altered phosphorylation of cytoskeleton proteins in sickle red blood cells: the role of protein kinase C, Rac GTPases, and reactive oxygen species," Blood Cells Mol Dis 2010, 45:41-45.

Hebbel, R.P. et al., "Erythrocyte adherence to endothelium in sickle-cell anemia: A possible determinant of disease severity," N Engl J Med 1980, 302:992-995.

Hines, P.C. et al., "Novel epinephrine and cyclic AMP-mediated activation of BCAM/Lu-dependent sickle (SS) RBC adhesion," Blood 2003, 101:3281-3287.

Houslay, M.D. & Kolch, W. Cell-type specific integration of cross-talk between extracellular signal-regulated kinase and cAMP signaling, Mol Pharmacol 2000, 58:659-668.

International Search Report and Written Opinion for International Application No. PCT/US2012/035837 dated Aug. 16, 2012 (16 pages).

International Search Report and Written Opinion for International Application No. PCT/US2013/070895 dated Jan. 17, 2014 (10 pages).

International Search Report and Written Opinion for International Patent Application PCT/US2015/032366 dated Aug. 12, 2015.

Jindal, H.K. et al., Specific loss of protein kinase activities in senescent erythrocytes, Blood 1996, 88:1479-1487.

Jo, S.-K. et al, "MEK inhibitor, U0126, attenuates cisplatin-induced renal injury by decreasing inflammation and apoptosis," Kidney Int. 2005;67(2):458-66.

Joslin, E.J. et al., EGF-receptor-mediated mammary epithelial cell migration is driven by sustained ERK signaling from autocrine stimulation, J. Cell Sci 2007, 120:3688-3699.

Kaul, D.K. et al., Vaso-occlusion by sickle cells: evidence for selective trapping of dense red cells, Blood 1986, 68:1162-116.

Kaul, D.K. et al. "Adhesion of sickle cells to vascular endothelium is critically dependent on changes in density and shape of the cells," Blood 1994, 83:3006-3017.

Koch, W.J. et al., "Direct evidence that Gi-coupled receptor stimulation of mitogen-activated protein kinase is mediated by G$\beta\gamma$ activation of p21ras," (1994) Proc Natl Acad Sci USA 91:12706-112710.

Laubach, J.P. et al., "Polycythemia vera erythroid precursors exhibit increased proliferation and apoptosis resistance associated with abnormal RAS and PI3K pathway activation," (2009) Experimental Hematology 37:1411-1422.

McElveen, R.L. et al., "Erk pathway inhibitor U0126 induces gamma-globin expression in erythroid cells," (2005) Cell Mol Biol (Noisy-le-grand) 51(2):215-227.

Mohandas, N. et al. "Sickle erythrocyte adherence to vascular endothelium. Morphologic correlates and the requirement for divalent cations and collagen-binding plasma proteins," J Clin Invest 1985, 76:1605-1612.

Nagata, Y. et al., "Requirement of activation of JNK and p38 for environmental stress-induced erythroid differentiation and apoptosis and of inhibition of ERK for apoptosis," (1999) Blood 94(3):853-863.

Polanowska-Grabowska, R. et al., "P-Selectin-mediated platelet-neutrophil aggregate formation activates neutrophils in mouse and human sickle cell disease," (2010) Arteriosclerosis, Thrombosis, and Vascular Biology 30:2392-2399.

Raghupathy, R. et al., "Promising Therapies in Sickle Cell Disease," (2009) Cardiovascular & Haematological Disorders-Drug Targets 9:1-18.

Rengo, G. et al., "GRK2 as a novel gene therapy target in heart failure," (2011) J. Mol Cell Cardiol 50(5):785-792.

Schmidt, E.K. et al., PI3 kinase is important for Ras, MEK and Erk activation of Epo-stimulated human erythroid progenitors, BMC Biol 2004, 2:7.

Schmitt, J.M. et al., "beta 2-adrenergic receptor activates extracellular signal-regulated kinases (ERKs) via the small G protein rap1 and the serine/threonine kinase B-Raf," J Biol Chem 2000, 275:25342-25350.

Selvaraj, S.K. et al., "Mechanisms of monocyte activation and expression of proinflammatory cytochemokines by placenta growth factor," (2003) Blood 102:1515-1524; prepublished online Apr. 10, 2003.

Serjeant, G.R., "Sickle-cell disease," (1997) The Lancet 350:725-730.

Soderblom, E. et al., "Proteomic analysis of ERK1/2-mediated human sickle red blood cell membrane protein phosphorylation," (2013) Clinical Proteomics 10:1-16.

Turhan, A. et al., Primary role for adherent leukocytes in sickle cell vascular occlusion: a new paradigm, Proc Natl Acad Sci U S A 2002, 99:3047-3051.

Udani, M. et al., Basal cell adhesion molecule/lutheran protein. The receptor critical for sickle cell adhesion to laminin, J Clin Invest 1998, 101:2550-2558.

Wannatung, T. et al., "Increased erythropoiesis of $\beta$-thalassaemia/Hb E proerythroblasts is mediated by high basal levels of ERK1/2 activation," (2009) British J. of Haematology 146:557-568.

Zambuzzi, W.F. et al., "On the road to understanding of the osteoblast adhesion: cytoskeleton organization is rearranged by distinct signaling pathways," J Cell Biochem 2009, 108:134-144.

Zennadi, R. et al., "Sickle red cells induce adhesion of lymphocytes and monocytes to endothelium," Blood 2008, 112:3474-3483.

Zennadi, R. et al., Atypical activation of plasma membrane-bound ERK1/2 is associated with regulation of sickle red cell adhesion to endothelium, Dec. 6, 2010, Retrieved from the Internet: https://ash.confex.com/ash/2010/webprogram/Paper33039.html (Abstract).

Zennadi, R. et al., "Epinephrine acts through erythroid signaling pathways to activate sickle cell adhesion to endothelium via LW-alphavbeta3 interactions," Blood 2004, 104:3774-3781.

Zennadi, R. et al., "Epinephrine-induced activation of LW-mediated sickle cell adhesion and vaso-occlusion in vivo," Blood 2007, 110:2708-2717.

Zennadi, R. et al., "Erythrocyte plasma membrane-bound ERK1/2 activation promotes ICAM-4-mediated sickle red cell adhesion to endothelium," (2012) Blood 119(5):1217-1227; prepublished online as Blood First Edition paper, Dec. 6, 2011.

Zennadi, R. "MEK inhibitors, novel anti-adhesive molecules, reduce sickle red blood cell adhesion in vitro and in vivo, and vasoocclusion in vivo," (2014) PloS One 9(10): e110306. doi:10.1371/journal.pone.0110306.

(56) References Cited

OTHER PUBLICATIONS

Zhao, Y. et al., "MEK1/2 inhibitors reverse acute vascular occlusion in mouse models of sickle cell disease," (2016) FASEB J 30: 1171-1186.

Phosphorylated Residue Distribution

- Phos Ser
- Phos Thr
- Phos Tyr

Phosphorylated residues per Peptide

- 1 Phos/Peptide
- 2 Phos/Peptide
- 3 Phos/Peptide
- >3 Phos/Peptide

SEQUENCE LISTING

```
<160> NUMBER OF SEQ ID NOS: 43

<210> SEQ ID NO 1
<211> LENGTH: 19
<212> TYPE: PRT
<213> ORGANISM: Homo sapiens
<220> FEATURE:
<221> NAME/KEY: misc_feature
<223> OTHER INFORMATION: Mitogen-Activated Protein Kinase-1
<220> FEATURE:
<221> NAME/KEY: MOD_RES
<222> LOCATION: (15)..(15)
<223> OTHER INFORMATION: PHOSPHORYLATION

<400> SEQUENCE: 1

Val Ala Asp Pro Asp His Asp His Thr Gly Phe Leu Thr Glu Tyr Val
1               5                   10                  15

Ala Thr Arg

<210> SEQ ID NO 2
```

```
<211> LENGTH: 15
<212> TYPE: PRT
<213> ORGANISM: Artificial Sequence
<220> FEATURE:
<223> OTHER INFORMATION: Synthetic: alpha-adducin
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION

<400> SEQUENCE: 2

Ser Pro Gly Ser Pro Val Gly Glu Gly Thr Gly Ser Pro Pro Lys
1               5                   10                  15

<210> SEQ ID NO 3
<211> LENGTH: 53
<212> TYPE: PRT
<213> ORGANISM: Artificial Sequence
<220> FEATURE:
<223> OTHER INFORMATION: Synthetic: alpha-adducin
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (47)..(47)
<223> OTHER INFORMATION: PHOSPHORYLATION

<400> SEQUENCE: 3

Glu Glu Glu Ala His Arg Pro Pro Ser Pro Thr Glu Ala Pro Thr Glu
1               5                   10                  15

Ala Ser Pro Glu Pro Ala Pro Asp Pro Ala Pro Val Ala Glu Glu Ala
            20                  25                  30

Ala Pro Ser Ala Val Glu Glu Gly Ala Ala Ala Asp Pro Gly Ser Asp
        35                  40                  45

Gly Ser Pro Gly Lys
    50

<210> SEQ ID NO 4
<211> LENGTH: 24
<212> TYPE: PRT
<213> ORGANISM: Artificial Sequence
<220> FEATURE:
<223> OTHER INFORMATION: Synthetic: beta-adducin
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 4

Glu Thr Ala Pro Glu Glu Pro Gly Ser Pro Ala Lys Ser Ala Pro Ala
1               5                   10                  15

Ser Pro Val Gln Ser Pro Ala Lys
            20

<210> SEQ ID NO 5
```

```
<211> LENGTH: 24
<212> TYPE: PRT
<213> ORGANISM: Artificial Sequence
<220> FEATURE:
<223> OTHER INFORMATION: Synthetic: beta-adducin
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 5

Glu Thr Ala Pro Glu Glu Pro Gly Ser Pro Ala Lys Ser Ala Pro Ala
1               5                   10                  15

Ser Pro Val Gln Ser Pro Ala Lys
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic: beta-adducin
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 6

Glu Thr Ala Pro Glu Glu Pro Gly Ser Pro Ala Lys Ser Ala Pro Ala
1               5                   10                  15

Ser Pro Val Gln Ser Pro Ala Lys
            20

<210> SEQ ID NO 7
<211> LENGTH: 15
<212> TYPE: PRT
<213> ORGANISM: Artificial Sequence
<220> FEATURE:
<223> OTHER INFORMATION: Synthetic: Dematin
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 7

Ser Thr Ser Pro Pro Ser Pro Glu Val Trp Ala Asp Ser Arg
1               5                   10                  15

<210> SEQ ID NO 8
<211> LENGTH: 21
<212> TYPE: PRT
<213> ORGANISM: Artificial Sequence
<220> FEATURE:
<223> OTHER INFORMATION: Synthetic: Leucine-zipper-like
      transcriptional regulator 1
<220> FEATURE:
<221> NAME/KEY: MOD_RES
<222> LOCATION: (7)..(7)
<223> OTHER INFORMATION: PHOSPHORYLATION
```

```
<400> SEQUENCE: 8

Met Ala Gly Pro Gly Ser Thr Gly Gly Gln Ile Gly Ala Ala Ala Leu
1               5                   10                  15

Ala Gly Gly Ala Arg
            20

<210> SEQ ID NO 9
<211> LENGTH: 18
<212> TYPE: PRT
<213> ORGANISM: Artificial Sequence
<220> FEATURE:
<223> OTHER INFORMATION: Synthetic: Adenylyl cyclase-associated protein
      1
<220> FEATURE:
<221> NAME/KEY: MOD_RES
<222> LOCATION: (14)..(14)
<223> OTHER INFORMATION: PHOSPHORYLATION

<400> SEQUENCE: 9

Ser Gly Pro Lys Pro Phe Ser Ala Pro Lys Pro Gln Thr Ser Pro Ser
1               5                   10                  15

Pro Lys

<210> SEQ ID NO 10
<211> LENGTH: 13
<212> TYPE: PRT
<213> ORGANISM: Artificial Sequence
<220> FEATURE:
<223> OTHER INFORMATION: Synthetic: Dematin
<220> FEATURE:
<221> NAME/KEY: MOD_RES
<222> LOCATION: (10)..(10)
<223> OTHER INFORMATION: PHOSPHORYLATION

<400> SEQUENCE: 10

Gln Pro Leu Thr Ser Pro Gly Ser Val Ser Pro Ser Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic: Alpha-adducin
<220> FEATURE:
<221> NAME/KEY: MOD_RES
<222> LOCATION: (4)..(4)
<223> OTHER INFORMATION: PHOSPHORYLATION

<400> SEQUENCE: 11

Gln Lys Gly Ser Glu Glu Asn Leu Asp Glu Ala Arg
1               5                   10

<210> SEQ ID NO 12
<211> LENGTH: 36
<212> TYPE: PRT
<213> ORGANISM: Artificial Sequence
<220> FEATURE:
<223> OTHER INFORMATION: Synthetic: Protein MICAL-2
<220> FEATURE:
<221> NAME/KEY: MOD_RES
<222> LOCATION: (2)..(3)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION
<220> FEATURE:
```

```
<221> NAME/KEY: MOD_RES
<222> LOCATION: (27)..(27)
<223> OTHER INFORMATION: PHOSPHORYLATION

<400> SEQUENCE: 12

Val Ser Ser Gly Ile Gly Ala Ala Ala Glu Val Leu Val Asn Leu Tyr
1               5                   10                  15

Met Asn Asp His Arg Pro Lys Ala Gln Ala Thr Ser Pro Asp Leu Glu
            20                  25                  30

Ser Met Arg Lys
        35

<210> SEQ ID NO 13
<211> LENGTH: 24
<212> TYPE: PRT
<213> ORGANISM: Artificial Sequence
<220> FEATURE:
<223> OTHER INFORMATION: Synthetic: facilitated glucose transporter
      member 1
<220> FEATURE:
<221> NAME/KEY: MOD_RES
<222> LOCATION: (5)..(5)
<223> OTHER INFORMATION: PHOSPHORYLATION

<400> SEQUENCE: 13

Gln Gly Gly Ala Ser Gln Ser Asp Lys Thr Pro Glu Glu Leu Phe His
1               5                   10                  15

Pro Leu Gly Ala Asp Ser Gln Val
            20

<210> SEQ ID NO 14
<211> LENGTH: 37
<212> TYPE: PRT
<213> ORGANISM: Artificial Sequence
<220> FEATURE:
<223> OTHER INFORMATION: Synthetic: U3 small nucleolar RNA-associated
      protein 15
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (33)..(33)
<223> OTHER INFORMATION: PHOSPHORYLATION

<400> SEQUENCE: 14

Val Val His Ser Phe Asp Tyr Ala Ala Ser Ile Leu Ser Leu Ala Leu
1               5                   10                  15

Ala His Glu Asp Glu Thr Ile Val Val Gly Met Thr Asn Gly Ile Leu
            20                  25                  30

Ser Val Lys His Arg
        35

<210> SEQ ID NO 15
<211> LENGTH: 33
<212> TYPE: PRT
<213> ORGANISM: Artificial Sequence
<220> FEATURE:
<223> OTHER INFORMATION: Synthetic: Leucine-rich repeats and
      immunoglobulin-like domains protein 2
<220> FEATURE:
<221> NAME/KEY: MOD_RES
<222> LOCATION: (1)..(1)
```

```
<223> OTHER INFORMATION: PHOSPHORYLATION
<220> FEATURE:
<221> NAME/KEY: MOD_RES
<222> LOCATION: (30)..(30)
<223> OTHER INFORMATION: PHOSPHORYLATION

<400> SEQUENCE: 15

Thr His Pro Glu Thr Ile Ile Ala Leu Arg Gly Met Asn Val Thr Leu
1               5                   10                  15

Thr Cys Thr Ala Val Ser Ser Ser Asp Ser Pro Met Ser Thr Val Trp
            20                  25                  30

Arg

<210> SEQ ID NO 16
<211> LENGTH: 42
<212> TYPE: PRT
<213> ORGANISM: Artificial Sequence
<220> FEATURE:
<223> OTHER INFORMATION: Synthetic: Transmembrane protein 151B
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 16

Ser Pro Pro Gly Ser Ala Ala Gly Glu Ser Ala Ala Gly Gly Gly Gly
1               5                   10                  15

Gly Gly Gly Gly Pro Gly Val Ser Glu Glu Leu Thr Ala Ala Ala Ala
            20                  25                  30

Ala Ala Ala Ala Asp Glu Gly Pro Ala Arg
            35                  40

<210> SEQ ID NO 17
<211> LENGTH: 17
<212> TYPE: PRT
<213> ORGANISM: Artificial Sequence
<220> FEATURE:
<223> OTHER INFORMATION: Synthetic: Eukaryotic translation initiation
      factor 4B
<220> FEATURE:
<221> NAME/KEY: MOD_RES
<222> LOCATION: (3)..(3)
<223> OTHER INFORMATION: PHOSPHORYLATION

<400> SEQUENCE: 17

Ser Gln Ser Ser Asp Thr Glu Gln Gln Ser Pro Thr Ser Gly Gly Gly
1               5                   10                  15

Lys

<210> SEQ ID NO 18
<211> LENGTH: 33
<212> TYPE: PRT
<213> ORGANISM: Artificial Sequence
<220> FEATURE:
<223> OTHER INFORMATION: Synthetic: Spectrin beta chain, erythrocyte
<220> FEATURE:
<221> NAME/KEY: MOD_RES
<222> LOCATION: (26)..(26)
<223> OTHER INFORMATION: PHOSPHORYLATION

<400> SEQUENCE: 18

Gln Ile Ala Glu Arg Pro Ala Glu Glu Thr Gly Pro Gln Glu Glu Glu
1               5                   10                  15
```

Gly Glu Thr Ala Gly Glu Ala Pro Val Ser His His Ala Ala Thr Glu
            20                  25                  30

Arg

<210> SEQ ID NO 19
<211> LENGTH: 31
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 19

Lys Ser Pro Ser Asp Val Lys Pro Leu Pro Ser Pro Asp Thr Asp Val
1               5                   10                  15

Pro Leu Ser Ser Val Glu Ile Glu Asn Pro Glu Thr Ser Asp Gln
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (18)..(19)
<223> OTHER INFORMATION: PHOSPHORYLATION

<400> SEQUENCE: 20

Ser Pro Ser Asp Val Lys Pro Leu Pro Ser Pro Asp Thr Asp Val Pro
1               5                   10                  15

Leu Ser Ser Val Glu Ile Glu Asn Pro Glu Thr Ser Asp Gln Val
            20                  25                  30

<210> SEQ ID NO 21
<211> LENGTH: 17
<212> TYPE: PRT
<213> ORGANISM: Artificial Sequence
<220> FEATURE:
<223> OTHER INFORMATION: Synthetic: 60S acidic ribosomal protein P2
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 21

Lys Glu Glu Ser Glu Glu Ser Asp Asp Asp Met Gly Phe Gly Leu Phe
1               5                   10                  15

Asp

<210> SEQ ID NO 22

```
<211> LENGTH: 30
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (13)..(13)
<223> OTHER INFORMATION: PHOSPHORYLATION

<400> SEQUENCE: 22

Ser Pro Ser Asp Val Lys Pro Leu Pro Ser Pro Asp Thr Asp Val Pro
1               5                   10                  15

Leu Ser Ser Val Glu Ile Glu Asn Pro Glu Thr Ser Asp Gln
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (28)..(28)
<223> OTHER INFORMATION: PHOSPHORYLATION

<400> SEQUENCE: 23

Ser Pro Ser Asp Val Lys Pro Leu Pro Ser Pro Asp Thr Asp Val Pro
1               5                   10                  15

Leu Ser Ser Val Glu Ile Glu Asn Pro Glu Thr Ser Asp Gln
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (3)..(3)
<223> OTHER INFORMATION: PHOSPHORYLATION

<400> SEQUENCE: 24

Ser Pro Ser Asp Val Lys Pro Leu Pro Ser Pro Asp Thr Asp Val Pro
1               5                   10                  15

Leu Ser Ser Val Glu Ile Glu Asn Pro Glu Thr Ser Asp Gln
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
```

```
<222> LOCATION: (10)..(10)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 25

Ser Pro Ser Asp Val Lys Pro Leu Pro Ser Pro Asp Thr Asp Val Pro
1               5                   10                  15

Leu Ser Ser Val Glu Ile Glu Asn Pro Glu Thr Ser Asp Gln
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Synthetic: Protein Wnt-16
<220> FEATURE:
<221> NAME/KEY: MOD_RES
<222> LOCATION: (28)..(28)
<223> OTHER INFORMATION: PHOSPHORYLATION

<400> SEQUENCE: 26

His Glu Arg Trp Asn Cys Met Ile Thr Ala Ala Ala Thr Thr Ala Pro
1               5                   10                  15

Met Gly Ala Ser Pro Leu Phe Gly Tyr Glu Leu Ser Ser Gly Thr Lys
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic: UV excision repair protein RAD23
      homolog A
<220> FEATURE:
<221> NAME/KEY: MOD_RES
<222> LOCATION: (4)..(4)
<223> OTHER INFORMATION: PHOSPHORYLATION

<400> SEQUENCE: 27

Glu Asp Lys Ser Pro Ser Glu Glu Ser Ala Pro Thr Thr Ser Pro Glu
1               5                   10                  15

Ser Val Ser Gly Ser Val Pro Ser Ser Gly Ser Gly Arg
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (27)..(27)
<223> OTHER INFORMATION: PHOSPHORYLATION

<400> SEQUENCE: 28

Ser Pro Ser Asp Val Lys Pro Leu Pro Ser Pro Asp Thr Asp Val Pro
1               5                   10                  15

Leu Ser Ser Val Glu Ile Glu Asn Pro Glu Thr Ser Asp Gln
            20                  25                  30

<210> SEQ ID NO 29
<211> LENGTH: 29
```

```
<212> TYPE: PRT
<213> ORGANISM: Artificial Sequence
<220> FEATURE:
<223> OTHER INFORMATION: Synthetic: Metabotropic glutamate receptor 7
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MOD_RES
<222> LOCATION: (25)..(25)
<223> OTHER INFORMATION: PHOSPHORYLATION

<400> SEQUENCE: 29

Leu Ser His Lys Pro Ser Asp Arg Pro Asn Gly Glu Ala Lys Thr Glu
1               5                   10                  15

Leu Cys Glu Asn Val Asp Pro Asn Ser Pro Ala Ala Lys
            20                  25

<210> SEQ ID NO 30
<211> LENGTH: 24
<212> TYPE: PRT
<213> ORGANISM: Artificial Sequence
<220> FEATURE:
<223> OTHER INFORMATION: Synthetic: Beta-adducin
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 30

Glu Thr Ala Pro Glu Glu Pro Gly Ser Pro Ala Lys Ser Ala Pro Ala
1               5                   10                  15

Ser Pro Val Gln Ser Pro Ala Lys
            20

<210> SEQ ID NO 31
<211> LENGTH: 31
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION

<400> SEQUENCE: 31

Lys Ser Pro Ser Asp Val Lys Pro Leu Pro Ser Pro Asp Thr Asp Val
1               5                   10                  15

Pro Leu Ser Ser Val Glu Ile Glu Asn Pro Glu Thr Ser Asp Gln
            20                  25                  30

<210> SEQ ID NO 32
<211> LENGTH: 21
<212> TYPE: PRT
<213> ORGANISM: Artificial Sequence
<220> FEATURE:
```

```
<223> OTHER INFORMATION: Synthetic: Beta-adducin
<220> FEATURE:
<221> NAME/KEY: MOD_RES
<222> LOCATION: (18)..(18)
<223> OTHER INFORMATION: PHOSPHORYLATION

<400> SEQUENCE: 32

Thr Glu Ser Val Thr Ser Gly Pro Met Ser Pro Glu Gly Ser Pro Ser
1               5                   10                  15

Lys Ser Pro Ser Lys
            20

<210> SEQ ID NO 33
<211> LENGTH: 30
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (19)..(19)
<223> OTHER INFORMATION: PHOSPHORYLATION

<400> SEQUENCE: 33

Ser Pro Ser Asp Val Lys Pro Leu Pro Ser Pro Asp Thr Asp Val Pro
1               5                   10                  15

Leu Ser Ser Val Glu Ile Glu Asn Pro Glu Thr Ser Asp Gln
            20                  25                  30

<210> SEQ ID NO 34
<211> LENGTH: 29
<212> TYPE: PRT
<213> ORGANISM: Artificial Sequence
<220> FEATURE:
<223> OTHER INFORMATION: Synthetic: Lipin-2
<220> FEATURE:
<221> NAME/KEY: MOD_RES
<222> LOCATION: (1)..(1)
<223> OTHER INFORMATION: PHOSPHORYLATION

<400> SEQUENCE: 34

Ser Gly Gly Asp Glu Thr Pro Ser Gln Ser Ser Asp Ile Ser His Val
1               5                   10                  15

Leu Glu Thr Glu Thr Ile Phe Thr Pro Ser Ser Val Lys
            20                  25

<210> SEQ ID NO 35
<211> LENGTH: 14
<212> TYPE: PRT
<213> ORGANISM: Artificial Sequence
<220> FEATURE:
<223> OTHER INFORMATION: Synthetic: Proteasome subunit alpha type-3
<220> FEATURE:
<221> NAME/KEY: MOD_RES
<222> LOCATION: (9)..(9)
<223> OTHER INFORMATION: PHOSPHORYLATION

<400> SEQUENCE: 35

Glu Ser Leu Lys Glu Glu Asp Glu Ser Asp Asp Asp Asn Met
1               5                   10

<210> SEQ ID NO 36
<211> LENGTH: 24
<212> TYPE: PRT
<213> ORGANISM: Artificial Sequence
<220> FEATURE:
<223> OTHER INFORMATION: Synthetic: Beta-adducin
<220> FEATURE:
```

```
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 36

Glu Thr Ala Pro Glu Glu Pro Gly Ser Pro Ala Lys Ser Ala Pro Ala
1               5                   10                  15

Ser Pro Val Gln Ser Pro Ala Lys
            20

<210> SEQ ID NO 37
<211> LENGTH: 31
<212> TYPE: PRT
<213> ORGANISM: Artificial Sequence
<220> FEATURE:
<223> OTHER INFORMATION: Synthetic: E3 ubiquitin-protein ligase UBR4
<220> FEATURE:
<221> NAME/KEY: MOD_RES
<222> LOCATION: (1)..(1)
<223> OTHER INFORMATION: PHOSPHORYLATION

<400> SEQUENCE: 37

Thr Ser Pro Ala Asp His Gly Gly Ser Val Gly Ser Glu Ser Gly Gly
1               5                   10                  15

Ser Ala Val Asp Ser Val Ala Gly Glu His Ser Val Ser Gly Arg
            20                  25                  30

<210> SEQ ID NO 38
<211> LENGTH: 16
<212> TYPE: PRT
<213> ORGANISM: Artificial Sequence
<220> FEATURE:
<223> OTHER INFORMATION: Synthetic: Spectrin beta chain, erythrocyte
<220> FEATURE:
<221> NAME/KEY: MOD_RES
<222> LOCATION: (2)..(3)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 38

Leu Ser Ser Ser Trp Glu Ser Leu Gln Pro Glu Pro Ser His Pro Tyr
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic: Uncharacterized protein LOC388588
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 39

Asp Gly Val Ser Leu Gly Ala Val Ser Ser Thr Glu Glu Ala Ser Arg
1               5                   10                  15
```

```
<210> SEQ ID NO 40
<211> LENGTH: 30
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (28)..(28)
<223> OTHER INFORMATION: PHOSPHORYLATION

<400> SEQUENCE: 40

Ser Pro Ser Asp Val Lys Pro Leu Pro Ser Pro Asp Thr Asp Val Pro
1               5                   10                  15

Leu Ser Ser Val Glu Ile Glu Asn Pro Glu Thr Ser Asp Gln
            20                  25                  30

<210> SEQ ID NO 41
<211> LENGTH: 16
<212> TYPE: PRT
<213> ORGANISM: Artificial Sequence
<220> FEATURE:
<223> OTHER INFORMATION: Synthetic: Spectrin beta chain, erythrocyte
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION

<400> SEQUENCE: 41

Leu Ser Ser Ser Trp Glu Ser Leu Gln Pro Glu Pro Ser His Pro Tyr
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic: Uncharacterized protein LOC388588
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 42

Asp Gly Val Ser Leu Gly Ala Val Ser Ser Thr Glu Glu Ala Ser Arg
1               5                   10                  15

<210> SEQ ID NO 43
<211> LENGTH: 30
<212> TYPE: PRT
<213> ORGANISM: Artificial Sequence
<220> FEATURE:
<223> OTHER INFORMATION: Synthetic: Glycophorin-A
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 43
```

-continued

```
Ser Pro Ser Asp Val Lys Pro Leu Pro Ser Pro Asp Thr Asp Val Pro
1               5                   10                  15

Leu Ser Ser Val Glu Ile Glu Asn Pro Glu Thr Ser Asp Gln
            20                  25                  30
```

METHODS OF TREATING HEMOGLOBINOPATHIES

CROSS-REFERENCE TO RELATED APPLICATIONS

This patent application is a divisional application of U.S. patent application Ser. No. 14/114,456, filed Oct. 28, 2013, which is a national stage filing under 35 U.S.C. § 371 of International Application No. PCT/US2012/035837, filed Apr. 30, 2012, which claims the benefit of priority of U.S. Provisional Patent Application No. 61/480,157, filed Apr. 28, 2011, which are incorporated herein by reference in their entireties.

REFERENCE TO SEQUENCE LISTING SUBMITTED VIA EFS-WEB

This application is being filed electronically via EFS-Web and includes an electronically submitted Sequence Listing in .txt format. The .txt file contains a sequence listing entitled "2012-05-29_5667-00087 Sequence_Listing.txt" created on May 21, 2012 and is 19.8 kilobytes in size. The Sequence Listing contained in this .txt file is part of the specification and is hereby incorporated by reference herein in its entirety.

STATEMENT REGARDING FEDERALLY SPONSORED RESEARCH

This invention was made with government support under K01-DK065040 awarded by the National Institutes of Health: National Institute of Diabetes and Digestive and Kidney Diseases. The government has certain rights in the invention.

BACKGROUND

Vaso-occlusive phenomena and hemolytic anemia are the clinical hallmarks of sickle cell disease (SCD). Sickle (homozygous hemoglobin S, SS) red blood cell (RBC)-based adhesion and vaso-occlusive events likely initiate and/or exacerbate the profound vasculopathy present in SCD.[1,2] SS RBCs possess unusually active signaling pathways that contribute to a panoply of abnormalities, including RBC adhesion to the endothelium and vaso-occlusion.[2-4] Vaso-occlusion results in recurrent painful episodes and a variety of serious organ system complications that can lead to life-long disabilities and even death.

Cell adhesion is a multistep cellular process that is regulated by complex extracellular and intracellular signals, which may differ from one cell type to another. We have previously shown that abnormal SS RBC interaction with the endothelium and with leukocytes can be induced via stimulation of $\beta_2$ adrenergic receptors (ARs) by the stress hormone epinephrine.[4-6] Such stimulation activates the intracellular cyclic adenosine monophosphate (cAMP)/protein kinase A (PKA) pathway.[4] βARs are prototypic G protein-coupled receptors (GPCRs), whose signaling properties are largely mediated by activation of stimulatory GTP-binding proteins (Gs proteins), which in turn activate adenylate cyclase (AC), leading to generation of cAMP, and the subsequent activation of PKA. The cAMP/PKA pathway can modulate the mitogen-activated protein kinase (MAPK)/extracellular signal-regulated kinase (ERKs) cascade.[7] PKA has been reported to stimulate B-Raf, while inhibiting c-Raf. Therefore, the activity of downstream signaling proteins, such as MEKs and ERKs, could be either enhanced or inhibited depending on the balance of c-Raf and B-Raf activation.[8,9] The cellular functions mediated by βARs can also be independent of adenylyl cyclase activation and involve other mediators instead.[10,11]

The functions attributed to ERK1/2 at both cellular and physiological levels are diverse, including modulation of proliferation, differentiation, apoptosis, migration, and cell adhesion.[12-15] Physiologically, ERK1/2 is required for immune system development, homeostasis and antigen activation, memory formation, heart development, and responses to many hormones, growth factors and insulin. Most of these previous studies have involved only nucleated cells, including erythroid cells, in which erythropoietin (EPO) is the primary regulatory cytokine of this pathway.[16] However, aberrations in ERK1/2 signaling are known to occur in a wide range of pathologies, including cancer, diabetes, viral infection, and cardiovascular disease.

SUMMARY

In some embodiments, methods of alleviating at least one symptom of a hemoglobinopathy in a patient is provided. In some embodiments, a hemoglobinopathy is selected from sickle cell disease, β-thalassemia, and hemoglobin H disease. In some embodiments, a hemoglobinopathy is sickle cell disease. In some embodiments, at least one symptom is selected from vaso-occlusion, acute painful episodes, chronic hemolysis (aplastic crises), avascular necrosis, infection, end-organ damage, and erythroid hyperplasia.

In some embodiments, methods of inhibiting adhesion of sickle red blood cells to endothelial cells in a patient are provided. In some embodiments, methods of inhibiting adhesion of sickle red blood cells to leukocytes in a patient are provided. In some embodiments, methods of inhibiting formation of multicellular aggregates in a patient with sickle cell disease are provided. In some embodiments, methods of inhibiting adhesion of leukocytes to endothelial cells in a patient with sickle cell disease are provided.

In some embodiments, a method comprises administering at least one inhibitor selected from a MEK inhibitor, an ERK inhibitor, and a Raf inhibitor.

In some embodiments, the inhibitor is a MEK inhibitor. In some embodiments, the MEK inhibitor is selected from U0126, RDEA119, GSK1120212, PD98059, PD-334581, GDC-0973, CIP-137401, ARRY-162, ARRY-300, PD318088, PD0325901, CI-1040, BMS 777607, AZD8330, AZD6244, AS703026. In some embodiments, the inhibitor is an ERK inhibitor. In some embodiments, the ERK inhibitor is AEZS-131. In some embodiments, the inhibitor is a Raf inhibitor. In some embodiments, the Raf inhibitor is selected from sorafenib tosylate, GDC-0879, PLX-4720, regorafenib, PLX-4032, SB-590885-R, RAF265, GW5074, XL281, and GSK2118436.

In some embodiments, a method of inhibiting adhesion of sickle red blood cells to endothelial cells is provided. In some embodiments, a method of inhibiting adhesion of sickle red blood cells to leukocytes is provided. In some embodiments, a method of inhibiting formation of multicellular aggregates in the presence of sickle red blood cells is provided. In some embodiments, a method of inhibiting adhesion of leukocytes to endothelial cells in the presence of sickle red blood cells is provided.

In some embodiments, a method comprises contacting sickle red blood cells with an inhibitor selected from a MEK inhibitor, an ERK inhibitor, and a Raf inhibitor.

In some embodiments, the inhibitor is a MEK inhibitor. In some embodiments, the MEK inhibitor is selected from U0126, RDEA119, GSK1120212, PD98059, PD-334581, GDC-0973, CIP-137401, ARRY-162, ARRY-300, PD318088, PD0325901, CI-1040, BMS 777607, AZD8330, AZD6244, AS703026. In some embodiments, the inhibitor is an ERK inhibitor. In some embodiments, the ERK inhibitor is AEZS-131. In some embodiments, the inhibitor is a Raf inhibitor. In some embodiments, the Raf inhibitor is selected from sorafenib tosylate, GDC-0879, PLX-4720, regorafenib, PLX-4032, SB-590885-R, RAF265, GW5074, XL281, and GSK2118436.

DESCRIPTION OF THE FIGURES

In FIG. 1A and FIG. 1B fifty μg of membrane protein ghosts (SS RBC ghosts, n=4, lanes: SS1, SS2, SS3 and SS4; and normal RBC ghosts, n=4, lanes: AA1, AA2, AA3 and AA4) were used per lane. Western blots of protein ghosts were stained with antibodies against ERK1/2, glycophorin C as a loading control, and MEK1/2 (n=3 for SS RBC ghosts, lanes: SS1, SS2 and SS3; and n=2 for normal RBC ghosts, lanes: AA1 and AA2). FIG. 1A. ERK1/2 and MEK1/2 are highly expressed in both SS and normal RBCs and are bound to the RBC plasma membrane. FIG. 1B. Quantitative analysis of the data (normalized according to glycophorin C expression) presented as relative ERK1/2 expression compared to normal RBCs ($p<0.05$ for SS vs normal RBCs, n=4 for each). In FIG. 1C and FIG. 1D normal RBCs (n=3, lanes: 1, 2, 3 and 4) and SS RBCs (n=3, lanes: 5, 6, 7 and 8) were sham-treated (lanes 1 and 5), incubated for 1 min with 20 nM epinephrine (epi) (lanes 2 and 6), pre-treated with the MEKI, U0126, followed by epi treatment (lanes 4 and 8), or treated with U0126 alone (lanes 3 and 7). Mouse 3T3/A31 fibroblast lysate was used as a positive control (lane 9). One hundred μg of SS and normal RBC ghost proteins were used per lane. Western blots were stained with antibodies against ERK and phosphoERK. FIG. 1C shows that ERK1/2 is phosphorylated at baseline in SS RBCs, and undergoes increased phosphorylation by epi stimulation. ERK in normal RBCs is not phosphorylated and completely failed to undergo increased phosphorylation after epi stimulation. FIG. 1D shows quantitative analysis of the data is presented as fold change in ERK phosphorylation. *$p<0.01$ compared to untreated cells. **$p<0.001$ compared to epi-treated SS RBCs. In FIG. 1E and FIG. 1F ERK was immunoprecipitated from sham-treated (lanes: 1, 2, 5, and 6) and epi-treated (lanes: 3, 4, 7, 8, 11, 12, 13 and 14) SS RBCs was incubated without MBP (lanes: 1, 3, 5, 7, 11 and 13) or with MBP (lanes: 2, 4, 6, 8, 12 and 14) as a substrate for ERK, with equal protein amounts per assay condition. Commercial active recombinant human ERK2 was incubated without MBP (lanes: 9 and 16) or with MBP (lanes: 10 and 15) as negative and positive controls, respectively. FIG. 1E shows immunoblots indicating that the activity of ERK is conserved and functional in SS RBCs and epi can intensify its activity. SS RBCs obtained from four different patients were tested. FIG. 1F shows quantitative analysis of the data is presented as fold change in ERK phosphorylation (n=4). $p=0.0286$ compared to non-treated cells.

FIG. 2A and FIG. 2B shows that ERK undergoes phosphorylation via the cAMP/PKA pathway. FIG. 2A shows that ERK undergoes increased phosphorylation after RBC incubation with forskolin, which is inhibited by U0126 (n=3). *$p<0.05$ compared to untreated cells. **$p<0.01$ compared to forskolin-treated SS RBCs. FIG. 2B shows phosphorylation of ERK is increased by epi, and this increase was abrogated by either 14-22 amide or U0126 (n=3). *$p<0.01$ compared to untreated cells. **$p<0.01$ compared to epi-treated SS RBCs. FIG. 2C shows ERK phosphorylation in SS RBCs is enhanced by inactivation of the Gα$_i$ protein. PTx at either 1 or 2 μg/ml increased basal ERK phosphorylation (n=9). *: $p<0.001$ compared to non-treated cells; t: $p<0.05$ compared to epi-treated SS RBCs. FIG. 2D shows that the tyrosine kinase p72$^{syk}$ is implicated in ERK phosphorylation. PTx at 2 μg/ml upregulated ERK phosphorylation, an effect that was blocked by piceatannol. Conversely, damnacanthal failed to block ERK phosphorylation induced by PTx (n=3). *$p<0.01$ compared to untreated cells. $p<0.01$ compared to PTx-treated SS RBCs. FIG. 2E shows ERK1/2 is phosphorylated at baseline in both reticulocyte-enriched and reticulocyte-depleted (mature) SS RBCs (n=2).

FIG. 3A and FIG. 3B shows activation of ERK signaling up-regulates SS RBC adhesion to the endothelium. SS RBCs were sham-treated, stimulated with epi for 1 min or forskolin, pre-incubated with U0126 followed by epi or forskolin, or treated with U0126 alone. Adhesion of SS RBCs to HUVECs was tested in intermittent flow condition assays. Results are presented as % adherent SS RBCs at a shear stress of 2 dynes/cm$^2$. Error bars show SEM of four different experiments. In FIG. 3A *: $p<0.001$ compared to sham-treated; **: $p<0.001$ compared to epi-treated. In FIG. 3B *: $p<0.001$ compared to sham-treated; **: $p<0.001$ compared to forskolin-treated. FIG. 3C and FIG. 3D show that the MEK/ERK signaling cascade is involved in ICAM-4 (LW) serine phosphorylation. FIG. 3C shows inorganic $^{32}$P radiolabeled intact SS RBCs were incubated in the absence (lane 1) or presence (lanes 2, 3, 4, 5 and 6) of serine/threonine protein phosphatase inhibitors (SPI), followed or not (lanes 1 and 2) by treatment with epi (lanes 3, 4, 5 and 6). In lanes 4, 5 and 6, SS RBCs were preincubated with PKAI, MEKI or PKAI+MEKI with SPI followed by epi treatment, respectively. The cpm are representative of three different experiments, calculated by subtraction of cpm present in a lane (not shown) containing immunoprecipitates using immunoglobulin P3 from cpm obtained using anti-LW (ICAM-4) mAb for immunoprecipitation under each set of conditions indicated. *: $p<0.05$ and $p<0.001$ for SPI-treated and SPI+epi-treated vs. sham-treated, respectively; **: $p<0.001$ compared to SPI+epi-treated SS RBCs. Total LW loaded in each lane was detected using nitrocellulose membranes of phosphorylated LW blotted with anti-LW mAb. FIG. 3D shows SS RBCs were incubated without (lanes 1 and 3) or with epi (lanes 2 and 4). Lanes 1 and 2 were immunoprecipitated with P3. Lanes 3 and 4 were immunoprecipitated with anti-LW mAb; all lanes for panel D were immunostained with anti-LW mAb.

FIG. 4A and FIG. 4B show adhesion of SS RBCs to endothelial cells is related to the duration of cell stimulation with epinephrine. Adhesion of RBCs to HUVECs was tested in both intermittent flow and flowing condition assays, and results are presented as % adherent RBCs at a shear stress of 2 dynes/cm$^2$ and number of adherent RBCs/mm$^2$, respectively. Normal and SS RBCs were sham-treated, or stimulated with epi for 1 min or 30 min. *: $p<0.001$ compared to sham-treated SS RBCs; **: $p<0.001$ compared to epi-treated SS RBCs. Error bars show SEM of four different experiments. FIG. 4C shows cAMP production in SS RBCs is associated with the time of cell stimulation with epinehprine. RBCs were treated with IBMX (for basal cAMP levels), followed or not with epi (for 1 min or 30 min) or forskolin. The specific effect of epi and forskolin on cAMP accumulation was obtained by subtracting basal cAMP levels from the total cAMP levels. The basal cAMP production and specific amounts of cAMP due to epi or forskolin stimulation were normalized as fmol cAMP/$10^8$ RBCs. FIG. 4D and FIG. 4E show ERK phosphorylation is dependent on the time of SS RBC exposure to epinephrine. SS RBCs were sham-treated or treated with epi for 1 or 30 min, U0126, or U0126 followed by epi for 1 or 30 min. Immunoblots of RBC proteins with antibodies against ERK and phosphoERK (FIG. 4D) and quantitative analysis of the data presented as fold change in ERK phosphorylation (FIG. 4E) are shown. ERK underwent increased phosphorylation after 1 min exposure to epi, while phosphorylation decreased with longer (30 min) cell exposure to epi (n=4). *: $p<0.01$ compared to non-treated cells; **: $p<0.01$ and $p<0.001$ for epi-treated for 30 min and U0126+epi-treated for 1 min vs cells treated with epi for 1 min, respectively (FIG. 4E). FIG. 4F shows inorganic $^{32}$P radiolabeled intact SS RBCs were incubated in the presence (lanes 1, 2 and 3) or absence (lane 4) of SPI, followed (lanes 2 and 3) or not (lane 1) by treatment with epi for 1 min (lane 2) or 30 min (lane 3). The cpm are representative of three different experiments, calculated by subtraction of cpm present in a lane (not shown) containing immunoprecipitates using immunoglobulin P3 from cpm obtained using anti-LW (ICAM-4) mAb for immunoprecipitation under each set of conditions indicated. *: $p<0.01$ compared to sham-treated; †: $p<0.05$ compared to SPI+epi (30 min)-treated SS RBCs. FIG. 4G shows prolonged cell exposure to epinephrine negatively affects phosphorylation of adenylate cyclase-associated protein 1. RBC ghosts isolated from SS and normal RBCs treated with epi for 1 and 30 min were enriched in phosphopeptides, then subjected to a label-free quantitative phosphoproteomics analysis. Phosphorylation of both serine and threonine on CAP1 in SS RBCs decreased with increased time (1 min vs 30 min) of cell exposure to epi, while an increase in the abandance of these phosphopeptides was observed in normal (AA) RBCs after 30 min exposure to epi. Each data point is an average of three analytical replicate measurements with error bars indicating standard deviations.

FIG. 8A shows SS RBCs were sham-treated, or treated with 10 µM U0126 MEK inhibitor. U0126 significantly inhibited SS RBC adherence to activated endothelial cells to levels below baseline adhesion of SS RBCs to non-activated HUVECs. *: $p<0.001$ compared to sham-treated SS RBCs adherent to non-activated HUVECs; **: $p<0.001$ compared to sham-treated SS RBCs adherent to TNF-$\alpha$-activated HUVECs. Error bars show SEM of 4 different experiments. FIG. 8B shows SS RBCs were sham-treated, or treated with 1 µM RDEA119, 10 µM RDEA119, 10 µM AZD6244 or 10 µM GSK1120212. All MEK inhibitors blocked SS RBC adhesion to activated HUVECs compared to sham-treated SS RBC adhesion to activated or non-activated HUVECs. *: $p<0.0001$ compared to sham-treated SS RBC adherent to non-activated or TNF-$\alpha$-activated HUVECs. Error bars show SEM of 3 different experiments.

In FIG. 9A mice (n=5) were injected with 0.02 mg/kg TNF-α intraperitoneally 4 hours before infusion into the tail vein of fluorescently-labeled human sickle RBCs. Human sickle RBCs showed striking adhesion to postcapillary venules, with permanent vaso-occlusion at junctions, although it was also observed in straight non-junctional venular segments as indicated by arrows. In FIG. 9B mice (n=5) were injected with 0.02 mg/kg TNF-α intraperitoneally 3 hours and 30 min before infusion into the tail vein of placebo (vehicle, 0.4% dimethyl sulfoxide (DMSO) in normal saline). Thirty minutes later, placebo-treated mice were infused into the tail vein with fluorescently-labeled human sickle RBCs. Infusion of human sickle RBCs resulted in marked RBC adhesion to postcapillary endothelium, with intermittent occlusion of vessels and permanent blockage of some vessel segments, especially at junctions. These data indicate that intravenous administration of placebo did not prevent human sickle red blood cell adhesion and vasoocclusion. In FIG. 9C and FIG. 9D mice were injected with 0.02 mg/kg TNF-α intraperitoneally 3 hours and 30 min before infusion into the tail vein of U0126 (2 mg/kg in 0.4% DMSO in normal saline, n=5) (FIG. 9C), or U0126 (0.2 mg/kg in 0.04% DMSO in normal saline, n=1) (FIG. 9D). Thirty minutes later, U0126-treated mice were infused with fluorescently-labeled human sickle RBCs. Human sickle RBCs showed little adhesion, which was observed only in few venular segments without promotion of frank vaso-occlusion as indicated by arrows. Scale bar=150 μm. FIG. 9E shows the effect of U0126 on % venular length occupied by SS RBCs. Video frames showing>30 vessel segments were used to quantify the length of venules occupied by SS RBCs in animals treated as described in FIGS. 9B, 9C and 9D. The values were averaged among groups of animals to represent the mean % venular length occupied by SS RBCs. Error bars show SEM. *: $p<0.001$ vs placebo for vessel diameter≤25 μm; **: $p<0.05$ vs placebo for vessel diameter>25 μm.

FIG. 10A shows infusion of sham-treated SS RBCs (n=5) resulted in marked RBC adherence in inflamed venules and vaso-occlusion as shown by arrows. FIG. 10B shows U0126-treated SS RBCs (n=5) show rare adhesion in inflamed vessels as indicated by arrows, but no apparent vaso-occlusion. FIG. 10C shows treatment of human SSRBCs with RDEA119 (n=5) dramatically decreased human SS RBC adhesion as indicated by arrows and prevented vessel obstruction. Scale bar=150 μm. FIG. 10D shows the effect of RDEA119 treatment of SS RBCs on % venular length occupied by treated SS RBCs. Video frames showing>30 vessel segments were used to quantify the length of venules occupied by SS RBCs in animals treated as described above. The values were averaged among groups of animals to represent the mean % venular length occupied by SS RBCs. Error bars show SEM of 5 different experiments for each treatment. *: $p<0.001$ vs sham for vessel diameter≤25 μm; **: $p<0.05$ vs sham for vessel diameter>25 μm.

(FIG. 15A) RBC membrane fractions from healthy (AA) and sickle-cell (SS) patients pre-treated with or without the MEK inhibitor, U0126, and subsequently with or without activated ERK2. (FIG. 15B) Analysis performed only on SS or AA RBC treatment groups.

DETAILED DESCRIPTION

Figure 1A:
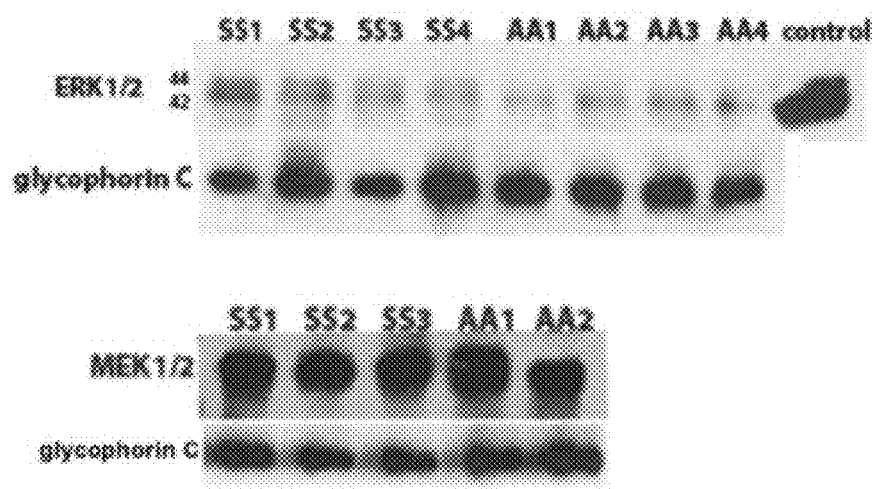
FIG. 1A-1F show that ERK undergoes activation in sickle (SS) but not normal red blood cells (RBCs).

Preliminary studies have suggested that the mitogen-activated protein kinase (MAPK)/the extracellular signal-regulated kinase (ERK1/2) is present at higher abundance in sickle red blood cells (SS RBCs) than in normal RBCs and is bound to the cytoplasmic membrane. The present inventors have shown that RK1/2 is active in enucleated SS RBCs, and that triggering this kinase promotes activation of signaling pathways and consequent RBC adhesion to the endothelium. Stimulation of $\beta_2$ adrenergic receptors ($\beta_2$ARs) on SS RBCs by epinephrine for a brief period of time increases activation of the ERK1/2 signaling cascade, which is involved in phosphorylation of the RBC adhesion receptor ICAM-4 and protein 4.1. The present inventors also found that the ERK consensus motifs on dematin and $\alpha$- and $\beta$-adducins undergo increased serine phosphorylation, indicating that these cytoskeletal proteins are substrates for ERK.

ERK has been implicated in erythropoietin-induced erythroid cell proliferation and survival,[29] and the present inventors have now demonstrated that the activity of this kinase and its upstream signal are conserved in mature SS RBCs. In some instances, ERK1/2 is hyperactive without stimulation of SS RBCs, and increased activation of this kinase can increase within 1 minute of SS RBC exposure to epinephrine. In contrast, in normal RBCs, despite the abundance of ERK1/2, ERK is not active at baseline and fails to become phosphorylated/activated with epinephrine or forskolin stimulation. The inability of ERK1/2 to undergo activation in normal RBCs suggests that the activity of ERK itself and/or at least one of the upstream effectors required for ERK activation is lost. Indeed, investigators have previously described that RBCs undergo maturation-related loss of multiple protein kinase activities, including PKA, PKC, and casein kinases.[30] In contrast, although SS RBCs are also fully differentiated, the present inventors have found that preservation of ERK activity and its downstream signaling molecules appears to be involved at least in the abnormal activation of RBC adhesive function.

Our data further implicate involvement of the protein $G_s$ and cAMP/PKA as upstream mediators in activation of ERK and its downstream signal transduction pathway. Our findings are consistent with studies by Schmitt and Stork[7] demonstrating that isoproterenol stimulation of endogenous $\beta_2$ARs activated ERK in HEK293 cells via a cAMP-dependent PKA pathway, and this ERK pathway was insensitive to the effect of PTx, which inactivates the protein $G\alpha_i$. In addition to PKA, we have also identified a role for the tyrosine kinase p72$^{Syk}$ in activation of ERK in SS RBCs, while excluding involvement of p56$^{lck}$-related Src family tyrosine kinases. Thus, in SS RBCs, PKA and the tyrosine kinase p72$^{Syk}$ are implicated in ERK activation, acting most likely in concert to regulate the MEK/ERK signaling pathway.

The engagement of epinephrine-stimulated ERK in regulation of SS RBC adhesion to the endothelium suggests that the MEK/ERK signal can promote an adhesive, vaso-occlusive pathology. It is also apparent from the data herein that epinephrine-induced adhesion of SS RBCs to non-activated endothelial cells requires ICAM-4 phosphorylation, which occurs via the cAMP/PKA/ERK signaling pathway. Furthermore, the adhesive function of SS RBCs appeared to be related to the extent of ERK and ICAM-4 phosphorylation/activation, since all three similarly increased or decreased depending on the time of cell exposure to epinephrine. Additionally, basal cAMP levels, the upstream effector of MEK/ERK, were much higher in SS RBCs than in normal cells, suggesting that the increased level of cAMP in SS RBCs reflects at least in part the persistence of the abnormal ERK activation and RBC adhesive phenotype. However, although epinephrine increased cAMP levels in only 50% of the SCD patient samples tested, cAMP production, which seems to be needed to activate ERK signaling in these sickle cells, was also influenced by the duration of cell exposure to epinephrine. This may be explained at least in part by the dramatic decrease in the abundance of phosphopeptides within CAP1 in SS RBCs due to continued cell exposure to epinephrine stimulation. PKA might also exert a negative feedback loop through activation of phosphodiesterases, resulting in cAMP hydrolysis switching off downstream signaling because of the extended cell exposure to epinephrine (Rochais F, J Biol Chem. 2004). CAPs are not only involved in adenylate cyclase (AC) association, but in actin binding, SH3 binding, and cell morphology maintenance as well (Hubberstey A V, FASEB, 2002; and Bertling E, Mol. Biol. Cell, 2004). Previous observations of increased normal RBC membrane filterability after epinephrine treatment for 20 min (Tuvia S, J. Physiol., 1999), explain the enhanced phosphorylated CAP1 in normal RBCs after 30 min epinephrine exposure. Furthermore, Shain et al.[31] suggested that maintenance of altered cell morphology required persistent increased cAMP levels due to continuous $\beta$AR stimulation. In contrast, our data suggest that when an increase in ERK activation occurs within 1 min of cell exposure to epinephrine, persistent $\beta_2$AR stimulation has a negative effect on ERK activation and consequently the RBC adhesive function. Based on this analysis, it is expected that inhibition of b-Raf or c-Raf will result in similar effects in SS RBCs as these are additional upstream activators in this pathway.

Figure 6:
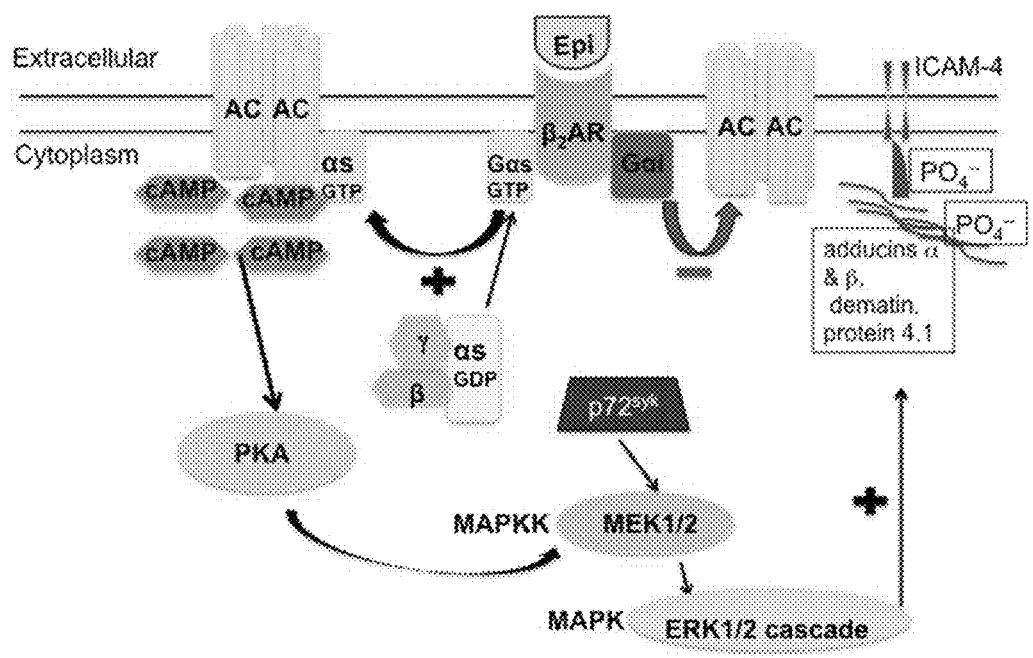
FIG. 6. Schematic depiction of proposed increased activation of ERK signaling pathway in SS RBCs. Epinephrine stimulates $\beta_2$ adrenergic receptors ($\beta_2$ARs) on SS RBCs. $\beta_2$ARs are prototypic $G_s$-coupled receptors (GPCRs), whose signaling is largely mediated by activation of stimulatory GTP-binding proteins ($G_s$ proteins), and inhibited by activation of $G\alpha_i$ protein. Activation of $G_s$ proteins in turn activates adenylate cyclase (AC), leading to generation of cAMP, and the subsequent activation of PKA. The activity of downstream signaling proteins, such as MEKs and ERKs is enhanced by PKA activation. The tyrosine kinase p72$^{Syk}$ acts synergistically with PKA to activate MEK/ERK cascade. Activation of ERK results in phosphorylation of the ERK consensus motif on the cytoskeletal proteins $\alpha$- and $\beta$-adducins, and dematin; and protein 4.1 albeit not at the ERK consensus motif. Phosphorylation of cytoskeletal proteins may result in cytoplasmic membrane protein conformational changes, which could render ICAM-4 accessible to phosphorylation.

The data herein also define the putative downstream targets of ERK in RBCs. Label-free quantitative phosphoproteomics analysis implicates ERK2 in phosphorylation of protein 4.1 and shows that the ERK consensus motifs on dematin and adducins $\alpha$ and $\beta$ undergo increased phosphorylation in the presence of this kinase. Dematin is also a substrate for PKC and PKA, and PKA-induced dematin phosphorylation completely abolishes its actin bundling capability.[32, 33] Alternatively, rapid phosphorylation of $\alpha$- and $\beta$-adducins by PKC at Ser-726 and Ser-713, respectively (Manno S, J Biol Chem, 2005) leads to decreased F-actin capping and dissociation of spectrin from actin, implicating adducin phosphorylation in cytoskeletal remodeling.[34] Furthermore, studies have previously shown that protein 4.1 phosphorylation, induced by cAMP-dependent kinase at Ser-331 and protein kinase C at Ser-312 documented after 20 min of cell stimulation (Manno S, J Biol Chem, 2005), results in a significant reduction in both the ability of protein 4.1 to promote spectrin binding to F-actin and in spectrin-protein 4.1 binding.[35] Thus, phosphorylation of cytoskeletal proteins and proteins of the junctional complexes by ERK in SS RBCs may also lead to cytoskeletal deorganization, which in turn, could potentially render ICAM-4 accessible to undergo phosphorylation, and to then mediate adhesion to the endothelium, or to affect its adhesivity with an as yet undetermined kinase. In fact, other investigators have shown that cell adhesion can be regulated by an intricate network of signaling molecules, which are responsible for guiding their interaction with substrate mainly via cytoskeleton rearrangement.[36] A schematic overview of the proposed $\beta_2$-AR signaling pathway in SS RBCs is shown in FIG. 6.

Finally, while aberrant ERK activation may arise in other pathologies, the present inventors are the first to describe atypical ERK activation in SS RBCs and its involvement in the abnormal RBC adhesion to the endothelium. Abnormal activation of ERK in SS RBCs may therefore be associated with the pathophysiology of sickle cell disease, making the MEK/ERK pathway a therapeutic target for preventing and treating vaso-occlusion. Various MEK and ERK inhibitors are currently being investigated in phase II clinical trials as therapeutic agents in cancer. The present invention provides methods of alleviating the symptoms of hemoglobinopathies, such as sickle cell disease and $\beta$-thalassemia, comprising administering MEK and/or ERK inhibitors.

The phospho-proteomic analysis presented in the Examples suggests that aberrant ERK activation may also be involved in additional symptoms and RBC defects associated with sickle cell disease. SS RBCs are characterized by a panoply of abnormalities, including polymerization of deoxygenated HbS, persistent oxidative membrane damage associated with HbS cyclic polymerization, abnormal activation of membrane cation transports, cell dehydration, and cytoskeletal dysfunction. In particular, the Examples demonstrate that ERK alters the phosphorylation state of proteins that may be involved in maintaining mechanical stability of RBC and may lead to a reduction in shear resistance as well as effect RBC shape, flexibility, anion transport and protein trafficking. Thus, MEK/ERK inhibition may result not only in amelioration of vaso-occlusion, but also other symptoms of sickle cell disease.

Definitions

The subject matter disclosed herein is described using several definitions, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising."

As used herein, the terms "patient" and "subject" may be used interchangeably and refer to one who receives medical care, attention or treatment. As used herein, the term is meant to encompass a person diagnosed with a disease such as a hemoglobinopathy or at risk for developing a hemoglobinopathy (e.g., a person who may be genetically homozygous or heterozygous for a sickle cell-causing mutation, but is not symptomatic). A "patient in need thereof" may include a patient having, suspected of having, or at risk for developing a hemoglobinopathy or symptoms thereof.

As used herein, the term "treatment," "treating," or "treat" refers to care by procedures or application that are intended to alleviate symptoms of a disease (including reducing the occurrence of symptoms of the disease). Although it is preferred that treating a condition or disease such as a hemoglobinopathy will result in an improvement of the condition, the term treating as used herein does not indicate, imply, or require that the procedures or applications are at all successful in alleviating symptoms associated with any particular condition. Treating a patient may result in adverse side effects or even a worsening of the condition which the treatment was intended to improve. Treating may include treating a patient having, suspected of having, or at risk for developing a hemoglobinopathy or symptoms thereof.

As used herein the term "effective amount" refers to the amount or dose of the agent, upon single or multiple dose administration to the subject, which provides the desired effect in the subject under diagnosis or treatment. The disclosed methods may include administering an effective amount of the disclosed agents (e.g., as present in a pharmaceutical composition) for treating a hemoglobinopathy in the patient, whereby the effective amount alleviates symptoms of the hemoglobinopathy (including reducing the occurrence of symptoms of the hemoglobinopathy).

An effective amount can be readily determined by the attending diagnostician, as one skilled in the art, by the use of known techniques and by observing results obtained under analogous circumstances. In determining the effective amount or dose of agent administered, a number of factors can be considered by the attending diagnostician, such as: the species of the patient; its size, age, and general health; the particular symptoms or the severity of the hemoglobinopathy; the response of the individual patient; the particular agent administered; the mode of administration; the bioavailability characteristics of the preparation administered; the dose regimen selected; the use of concomitant medication; and other relevant circumstances.

The phrase "alleviates at least one symptom," as used herein, means that a particular treatment results in a lessening of at least one symptom of a disease. Such lessening of a symptom may be a qualitative or quantitative reduction in the severity of the symptom, or may be a reduction in the number of occurrences of the symptom; even though each occurrence may be as severe as it was before the treatment (one or more occurrences may also be less severe). Non-limiting exemplary symptoms of sickle cells disease include vaso-occlusion, acute painful episodes, chronic hemolysis (aplastic crises), avascular necrosis, infection, end-organ damage, acute chest syndrome, leg ulceration, priapism, and decreased life expectancy. Nonlimiting exemplary symptoms of thalassemia include hemolysis, erythroid hyperplasia, biliary tract disease, infection, leg ulcers, extramedullary hematopoiesis, increased risk for developing thromboembolic phenomena, liver and heart damage, and decreased life expectancy.

The term "hemoglobinopathy," as used herein, refers to a condition that is caused by a genetic mutation in a globin gene that results in a mutated hemoglobin α chain or β chain protein, or a condition that is caused by a genetic mutation that results in an abnormal ratio of hemoglobin α chain to β chain or crossover fusion products of 2 globin genes. Non-limiting exemplary hemoglobinopathies include sickle cell disease (including, but not limited to, homozygous for hemoglobin S and a variety of sickle cell syndromes that result from inheritance of the sickle cell gene in compound heterozygosity with other mutant beta globin genes, including, but not limited to, hemoglobin SC disease (HbSC), sickle beta(+) thalassemia, sickle beta(0) thalassemia, sickle alpha thalassemia, sickle delta beta(0) thalassemia, sickle Hb Lepore, sickle HbD, sickle HbO Arab, and sickle HbE), β-thalassemia (including, but not limited to, β-thalassemia major (also known as Cooley's anemia) and β-thalassemia intermedia, and hemoglobin H disease (α-thalassemia with $\alpha^+$-$\alpha^0$ phenotype)). Nonlimiting exemplary genetic mutations that cause sickle cell disease include Hb SS, which is hemoglobin with an E6V mutation in each of the two hemoglobin β chains; Hb SC, which is hemoglobin with one β chain with an E6V mutation and one β chain with an E6K mutation; Hb SD, which is hemoglobin with one (3 chain with an E6V mutation and one β chain with a β121 Glu→Gln mutation; sickle-HbO Arab, which is hemoglobin with one β chain with an E6V mutation and one β chain with a β121(GH4)gGlu→Lys mutation; and Hb SE, which is hemoglobin with one β chain with an E6V mutation and one β chain with an E26K mutation. Nonlimiting exemplary genetic mutations that cause β-thalassemia include various R-mutations, such as IVS II-I, CD 36/37, CD41/42, CD 39; IVS1-6; IVS1-110, CD71/72, IVS1-5, IVS1-1, CD26, IVS2-654, CAP+1, CD19, -28, -29, IVS1-2, InCD (T-G) and CD17; and rare β-mutations, i.e. InCD (A-C), CD8/9, CD43, -86, CD15, Poly A, Poly TIC, IVS2-1, CD1, CD35/36, CD27/28, CD16, CD37, and 619bpDEL. Nonlimiting exemplary genetic mutations that cause Hb H disease include $\alpha^+$-$\alpha^0$ phenotypes such as α2 Poly A (AATAAA→AATA-), α2 Poly A (AATAAA→AATGAA), and α2 Poly A (AATAAA→AATAAG); $\alpha^+$ phenotypes such as α2 CD 142 (TAA→CAA), α2 CD 142 (TAA→AAA), and α2 CD 142 (TAA→TAT); and $\alpha^0$ phenotypes such as—$\alpha^{3.7}$ Init CD (ATG→GTG), $-^{SEA}$, $-^{THAI}$, $-^{MED\ II}$, $-^{BRIT}$, $-^{MED\ I}$, $-^{SA}$, $-(\alpha)^{20.5}$, and $-^{FIL}$.

The term "MEK inhibitor," as used herein, refers to an inhibitor of MEK kinase activity. A MEK inhibitor may be any type of molecule, including, but not limited to, small molecules and expression modulators (such as antisense molecules, microRNAs, siRNAs, etc.), and may act directly on the MEK protein, may interfere with expression of the MEK protein (e.g., transcription, splicing, translation, and/or post-translational processing), and/or may prevent proper intracellular localization of the MEK protein. Exemplary MEK inhibitors include, but are not limited to, U0126, PD98059, PD-334581, GDC-0973, CIP-137401, ARRY-162, ARRY-300, PD318088, PD0325901, CI-1040, BMS 777607, AZD8330, AZD6244, RDEA119, GSK1120212 and AS703026.

The term "ERK inhibitor," as used herein, refers to an inhibitor of ERK kinase activity. An ERK inhibitor may be any type of molecule, including, but not limited to, small molecules and expression modulators (such as antisense molecules, microRNAs, siRNAs, etc.), and may act directly on the ERK protein, may interfere with expression of the ERK protein (e.g., transcription, splicing, translation, and/or post-translational processing), and/or may prevent proper intracellular localization of the ERK protein. A nonlimiting exemplary ERK inhibitor is AEZS-131.

The term "Raf inhibitor," as used herein, refers to an inhibitor of b-Raf kinase activity and/or c-Raf kinase activity. A Raf inhibitor may be any type of molecule, including, but not limited to, small molecules and expression modulators (such as antisense molecules, microRNAs, siRNAs, etc.), and may act directly on the Raf protein, may interfere with expression of the Raf protein (e.g., transcription, splicing, translation, and/or post-translational processing), and/or may prevent proper intracellular localization of the Raf protein. Nonlimiting exemplary Raf inhibitors include sorafenib tosylate, GDC-0879, PLX-4720, regorafenib, PLX-4032, SB-590885-R, RAF265, GW5074, XL281, and GSK2118436.

A table providing additional information on some of the exemplified MEK, ERK, and B-Raf inhibitors is provided below as Table 4.

TABLE 4

Non-limiting exemplary inhibitors of MEK, ERK, and/or B-Raf

| Inhibitor | Alternate name(s) | Structure or source |
|---|---|---|
| U0126 | U0126-EtOH | 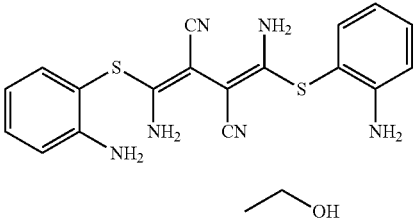 |
| PD98059 | | 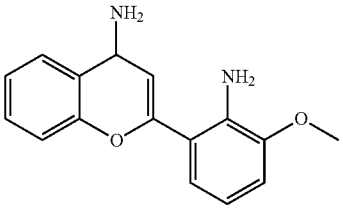 [SMILES: COc1cccc(C2=CC(N)c3ccccc3O2)c1N] |

TABLE 4-continued
Non-limiting exemplary inhibitors of MEK, ERK, and/or B-Raf
| Inhibitor | Alternate name(s) | Structure or source |
|---|---|---|
| PD-334581 | | 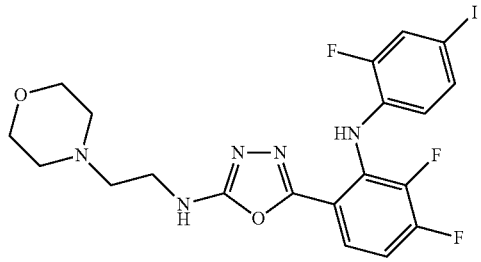 [SMILES: Fc1cc(I)ccc1Nc1c(-c2nnc(NCCN3CCOCC3)o2)ccc(F)c1F]<br>Chemical Formula: $C_{20}H_{19}F_3IN_5O_2$<br>Molecular Weight: 545.30 |
| GDC-0973 | XL518 | Genentech |
| CIP-137401 | CIP-1374 | Allostem Therapeutics |
| ARRY-162 | | Array BioPharma/Novartis |
| ARRY-300 | | Array BioPharma/Novartis |
| PD318088 | | 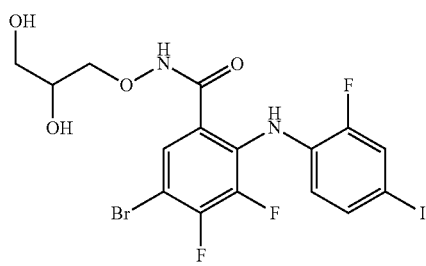 [SMILES: O=C(NOCC(O)CO)c1cc(Br)c(F)c(F)c1Nc1ccc(I)cc1F] |
| PD0325901 | | 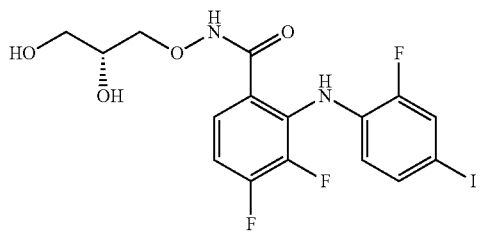 [SMILES: O=C(NOC[C@H](O)CO)c1ccc(F)c(F)c1Nc1ccc(I)cc1F] |
| CI-1040 | PD184352 | 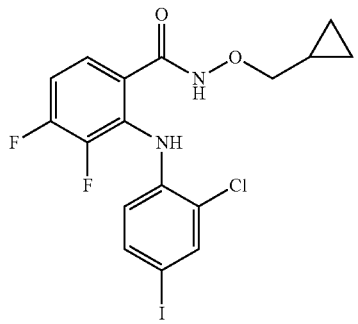 [SMILES: O=C(NOCC1CC1)c1ccc(F)c(F)c1Nc1ccc(I)cc1Cl] |

TABLE 4-continued

Non-limiting exemplary inhibitors of MEK, ERK, and/or B-Raf

| Inhibitor | Alternate name(s) | Structure or source |
|---|---|---|
| BMS 777607 | | |
| AZD8330 | ARRY-424704 ARRY-704 | |
| AZD6244 | Selumetinib | |
| AS703026 | MSC1936369B | |
| AEZS-131 | | Aeterna Zentaris Inc. |
| sorafenib tosylate | BAY 43-9006 AZ 628 | $C_7H_8O_3S$ |
| GDC-0879 | | |

TABLE 4-continued
Non-limiting exemplary inhibitors of MEK, ERK, and/or B-Raf
| Inhibitor | Alternate name(s) | Structure or source |
|---|---|---|
| PLX-4720 | | 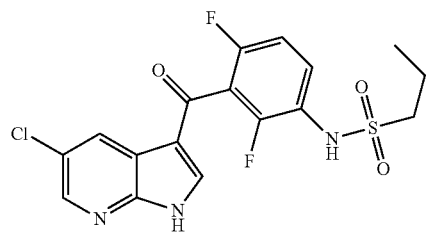 [SMILES: CCCS(=O)(=O)Nc1ccc(F)c(C(=O)c2c[nH]c3ncc(Cl)cc23)c1F] |
| regorafenib | BAY 73-4506 | 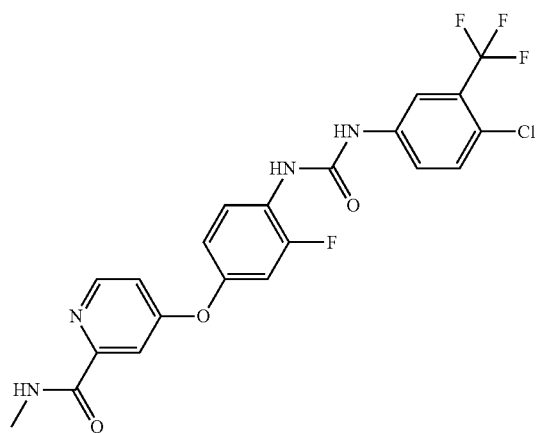 [SMILES: CNC(=O)c1cc(Oc2ccc(NC(=O)Nc3ccc(Cl)c(C(F)(F)F)c3)c(F)c2)ccn1] |
| PLX-4032 | RG7204 | 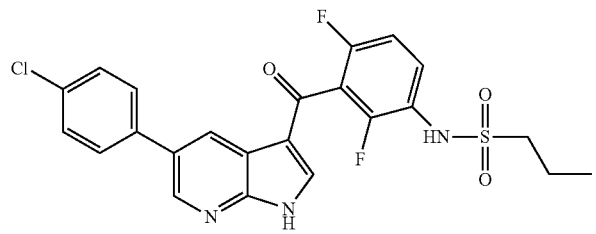 [SMILES: CCCS(=O)(=O)Nc1ccc(F)c(C(=O)c2c[nH]c3ncc(-c4ccc(Cl)cc4)cc23)c1F] |
| SB-590885 | | 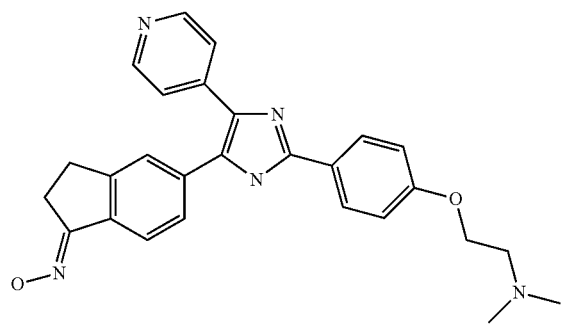 [SMILES: CN(C)CCOc1ccc(-c2nc(-c3ccncc3)c(-c3ccc4c(c3)CC/C4=N\O)[nH]2)cc1] |
| RAF265 | CHIR-265 | 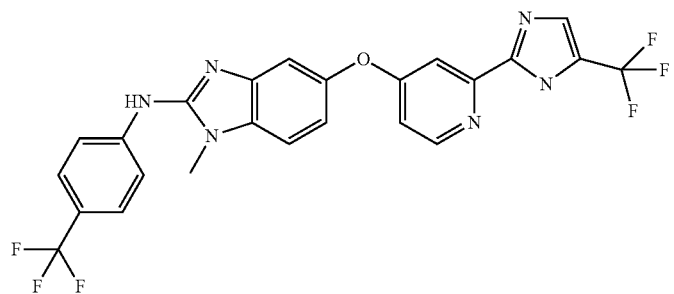 |

TABLE 4-continued

Non-limiting exemplary inhibitors of MEK, ERK, and/or B-Raf

| Inhibitor | Alternate name(s) | Structure or source |
|---|---|---|
| GW5074 | | (structure shown) |
| XL281 | BMS-908662 | Exelixis |
| GSK2118436 | | GlaxoSmithKline |

In some embodiments, methods of alleviating at least one symptom of a hemoglobinopathy in a patient are provided. Such methods comprise, in some embodiments, administering to the patient an inhibitor selected from a MEK inhibitor, an ERK inhibitor, and a Raf inhibitor. Nonlimiting exemplary hemoglobinopathies include β-thalassemia, sickle cell disease and Hemoglobin H.

For the treatment of sickle cell disease or other hemoglobinopathies, in some embodiments, at least one symptom that may be alleviated by administering the inhibitors described herein is selected from vaso-occlusion, acute painful episodes, chronic hemolysis (aplastic crises), avascular necrosis, infection, end-organ damage, and erythroid hyperplasia. In some embodiments, alleviating a symptom of sickle cell disease means reducing the amount, frequency, duration or severity of the symptom. For example, for vaso-occlusion, in some embodiments, alleviating the symptom includes reducing the average size of the vaso-occlusions and/or reducing the number of vaso-occlusions. Further, alleviating a symptom may or may not result in a reduction in the discomfort experienced by the patient as a result of the symptom. That is, in some embodiments, while the number and/or average size of vaso-occlusions may be reduced following a treatment described herein, the patient may or may not experience a similar reduction in acute pain caused by vaso-occlusion.

In some embodiments, when vaso-occlusion is alleviated by administration of an inhibitor described herein, acute painful episodes are also alleviated (i.e., the number and/or severity is reduced). In some embodiments, when vaso-occlusion is alleviated by administration of an inhibitor described herein, hemolysis is also alleviated. In some embodiments, vascular endothelial injury is alleviated by administration of an inhibitor described herein. In some embodiments, when hemolysis is alleviated by administration of an inhibitor described herein, the incidence of infections is reduced. In some embodiments, when hemolysis is alleviated by administration of an inhibitor described herein, erythroid hyperplasia is also alleviated. In some embodiments, when vaso-occlusion and/or hemolysis are alleviated by administration of an inhibitor described herein, end-organ damage is also alleviated.

In some embodiments, methods of inhibiting adhesion of sickle red blood cells to endothelial cells are provided. In some embodiments, methods of inhibiting adhesion of sickle red blood cells to leukocytes are provided. Such methods comprise, in some embodiments, contacting the sickle red blood cells with an inhibitor selected from a MEK inhibitor, an ERK inhibitor, and a Raf inhibitor.

In some embodiments, methods of inhibiting adhesion of sickle red blood cells to endothelial cells in a patient are provided. In some embodiments, methods of inhibiting adhesion of sickle red blood cells to leukocytes in a patient are provided. Such methods comprise, in some embodiments, administering to the patient an inhibitor selected from a MEK inhibitor, an ERK inhibitor, and a Raf inhibitor.

In some embodiments, a method comprises administering to the patient, or contacting a sickle red blood cell with, a MEK inhibitor. Nonlimiting exemplary MEK inhibitors include U0126, PD98059, PD-334581, GDC-0973, CIP-137401, ARRY-162, ARRY-300, PD318088, PD0325901, CI-1040, BMS 777607, AZD8330, AZD6244, RDEA119, GSK1120212 and AS703026. In some embodiments, a method comprises administering to the patient, or contacting a sickle red blood cell with, an ERK inhibitor. A nonlimiting exemplary ERK inhibitor is AEZS-131. In some embodiments, a method comprises administering to the patient, or contacting a sickle red blood cell with, a Raf inhibitor. In some embodiments, the Raf inhibitor inhibits b-RAF. In some embodiments, the Raf inhibitor inhibits c-Raf. In some embodiments, the Raf inhibitor inhibits both b-Raf and c-Raf. Nonlimiting exemplary Raf inhibitors include sorafenib tosylate, GDC-0879, PLX-4720, regorafenib, PLX-4032, SB-590885-R, RAF265, GW5074, XL281, and GSK2118436.

In some embodiments, a method comprises administering to the patient, or contacting a sickle red blood cell with a combination of two or more inhibitors selected from a MEK inhibitor, an ERK inhibitor, and a Raf inhibitor. The two or more inhibitors may be co-administered. Co-administration indicates the inhibitors may be administered in any order, at the same time or as part of a unitary composition. The two inhibitors may be administered such that one inhibitor is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

Administration to a subject may include formulating the therapeutic agents, such as a MEK inhibitor, an ERK inhibitor, and/or a B-Raf inhibitor, with pharmaceutically acceptable carriers and/or excipients, etc., to form pharmaceutical compositions. Suitable formulations for therapeutic compounds are available to those skilled in the art. Administration may be carried out by any suitable method, including intraperitoneal, intravenous, intramuscular, intrathecal, subcutaneous, transcutaneous, oral, nasopharyngeal, or transmucosal absorption among others. The dosage for a particular subject may be determined based on, for example, the subject's weight, height, and/or age; the severity of the subject's disease or symptoms; the length of treatment and/or number of doses anticipated in a particular regiment; the route of administration; etc.

The following examples are illustrative and are not intended to limit the disclosed subject matter. All references cited herein are incorporated herein by reference in their entireties.

EXAMPLES

Example 1: Materials and Methods

Endothelial Cells.

Primary human umbilical vein endothelial cells (HUVECs) were grown as monolayers in EBM2 medium (Lonza Walkersville, Inc., Walkersville, Md.) supplemented with EGM2 (Lonza Walkersville) as described previously.[4] EC passage was accomplished with trypsinization, as required. Cells were used until they reached the 5th passage. For flow chamber experiments, HUVECs were cultured until they reached confluence on clear glass slides precoated with 2% gelatin.

Antibodies.

Antibodies used included the following monoclonal and polyclonal antibodies (Abs, as purified immunoglobulin [Ig] unless otherwise noted): BS46 (mouse anti-ICAM-4, generously provided by Dr. Jean-Pierre Cartron, INSERM Unite 665, Paris, France);[17] and mouse anti-phospho-myelin basic protein (Millipore, Temecula, Calif.); mouse anti-human transferrin receptor (BD Biosciences, San Jose, Calif.); and mouse anti-human glycophorin C produced in our laboratory. Rabbit anti-human ERK1/2 was from Upstate, Charlottesville, Va.; rabbit anti-human phospho-ERK1/2 was from Cell Signaling Technology, Danvers, Mass.; and rabbit anti-human MAPK kinase (MEK1/2) was from Sigma-Aldrich, St. Louis, Mo. The murine myeloma protein P3×63/Ag8 (P3 ascitic fluid, diluted 1:500) was used as a non-reactive control murine Ig for mAbs.[18] In all studies, Abs were used at saturating dilutions unless otherwise indicated.

Collection, Preparation and Treatment of RBCs.

Sickle cell patient donors had not been transfused for at least three months, had not experienced vaso-occlusion for three weeks, and were not on hydroxyurea. Fresh blood samples from patients homozygous for hemoglobin S and from healthy donors were collected into citrate tubes. Blood was used within less than 24 h of collection. Packed RBCs were separated as previously described in detail.[5] RBCs were separated from the buffy coat containing leukocytes and platelet-rich plasma by gravity at 4° C. for at least 2 h. Plasma and buffy coat were removed by aspiration, and RBCs were washed four or five times in sterile PBS with 1.26 mM $Ca^{2+}$, 0.9 mM $Mg^{2+}$ (pH 7.4). Packed RBCs were analyzed for leukocyte and platelet contamination using an Automated Hematology Analyzer Sysmex K-1000 (Sysmex, Co., Cobe, Japan).

Aliquots of packed RBCs were treated with various reagents to affect cAMP signaling or protein phosphorylation. Sham-treated RBCs were incubated with the same buffer and vehicle, but without the active agent. Unless otherwise indicated, RBCs were treated at 37° C. with one or more of the following reagents: 20 nM epinephrine (Sigma-Aldrich, St. Louis, Mo.) for 1 or 30 min; 2 mM phosphodiesterase inhibitor 3-isobutyl-1-methylxanthine (IBMX, Sigma) for 2 h; 80 μM forskolin (Sigma) for 30 min; 1 or 2 μg/ml Pertussis toxin (PTx, Calbiochem, La Jolla, Calif.); 5 μM MEK1/2 inhibitor (MEKI, U0126, Calbiochem); 30 nM protein kinase A inhibitor (PKAI) 14-22 amide (Calbiochem); 10 μM damnacanthal (Enzo Life Sciences International, Inc., Plymouth Meeting, Pa.); or 10 μM piceatannol (Enzo Life Sciences International, Inc.) for 1 h. Treated RBCs were then washed 5 times with 4 ml PBS with $Ca^{2+}$ and $Mg^{2+}$. Normal RBCs were used as controls. Prior to adhesion assays, treated RBCs were labeled with PKH 26 red fluorescent cell linker kit (Sigma), following the manufacturer's instructions.

For in vitro adhesion assays, human SS RBCs were sham-treated with buffer and vehicle alone or treated at 37° C. with the MEK inhibitor, U0126 (Calbiochem, La Jolla, Calif.) at 10 μM for 1 h, followed or not by treatment with 20 nM epinephrine for 1 min or 80 μM forskolin for 30 min. Cells were then washed three times with 5 ml PBS with $Ca^{2+}$ and $Mg^{2+}$. Prior to adhesion assays, washed treated SS RBCs were labeled with PKH 26 red fluorescent cell linker kit (Sigma-Aldrich, St. Louis, Mo.), following the manufacturer's instructions.

For some in vivo adhesion studies, packed SS RBCs were fluorescently labeled with the dye DiI (Molecular Probes Inc., Eugene, Oreg.), following the manufacturer's instructions. DiI was used in our previous in vivo studies and by other investigators, and this dye have no effect on RBC suspension viscosity and RBC survival in circulation (Unthank J L et al. Microvasc. Res. 1993; 45:193-210; Zennadi et al., Blood 2007). Cell morphology was checked by microscopy.

Western Blot.

Treated packed RBCs were lysed with hypotonic buffer (5 mM $Na_2HPO_4$+1 mM EDTA+0.1% $NaN_3$, pH 8) containing 2 mM phenylmethylsulphonylfluoride (PMSF, Sigma), phosphatase inhibitor cocktail (Sigma) and protease inhibitor cocktail (Sigma). Protein separation by polyacrylamide gel electrophoresis using equal amounts of total RBC membrane ghost proteins per lane, after correcting total protein measurements for residual hemoglobin content, and Western blot[19] using the appropriate Ab were then performed. Mouse 3T3/A31 fibroblast lysate was used as a ERK1/2 positive control for immunoblots. For total ERK1/2, membranes blotted with anti-phosphoERK Ab were stripped and reexposed to Western blotting using anti-ERK1/2 Ab. Bands were analyzed densitometrically using ImageJ software downloaded from the NIH website. PhosphoERK1/2 data were normalized according to total ERK1/2 and are presented as fold change in ERK phosphorylation.

MAP Kinase Activity Assay.

Treated packed SS RBCs were lysed for 20 min at 4° C. with lysis buffer (10 mM EDTA, 20 mM Tris, 110 mM NaCl, pH 7.5) containing 2 mM PMSF, 1% Triton X-100, phosphatase inhibitor cocktail (Sigma) and protease inhibitor cocktail (Sigma). ERK1/2 was immunoprecipitated with anti-ERK1/2 antibody at 4° C., and immune complexes were obtained using protein A-agarose (Amersham Biosciences Corp., Piscataway, N.J.). ERK1/2 immunocomplex was examined for ERK1/2 activity using myelin basic protein (MBP) at 2 mg/ml (Millipore) as a substrate and ATP as a phosphate donor with equal protein amounts per assay condition. For the negative control, an equal volume of water was substituted for ERK1/2 substrate. Commercial active recombinant human ERK2 was used (Sigma) as a positive control. The reaction mixture was incubated for 20 min at 30° C., followed by protein separation and immunoblotting using anti-phosphoMBP mAb (Millipore).

Non-radiolabeled RBC ghosts isolated from packed RBCs sham-treated, or treated with U0126 or epinephrine for 1 or 30 min were separated by mass spectrometry, and then subjected to Label-Free quantitative phosphoproteomic analysis after phosphopeptide enrichment (see below).

Reticulocyte Enrichment.

Reticulocytes were separated from mature SS RBCs using anti-transferrin receptor mAb and goat anti-mouse IgG-coated micro-bead affinity columns (MACS, Miltenyi Biotec, Inc, Auburn, Calif.), following the manufacturer's instructions.

Flow Chamber Assays.

Graduated height flow chambers were used to quantify adhesion of RBCs to HUVECs substantially as previously described in detail.[4, 20] In some adhesion studies, slides coated with HUVECs were treated with human recombinant TNF-α at 10 ng/ml for 4 hours. Slides coated with HUVECs treated or not with TNF-α were then washed three times with 20 ml HBSS with 1.26 mM $Ca^{2+}$, 0.9 mM $Mg^{2+}$ (Gibco, Grand Island, N.Y.) warmed previously to 37° C. and then fit into a variable height flow chamber. The flow chamber was mounted on the stage of an inverted phase contrast microscope (Diaphot, Nikon Inc., Melville, N.Y.) connected to a thermoplate (Tokai Hit Co., Ltd., Japan) set at 37° C. Cells were observed using a video camera (RS photometrics,) attached to the microscope and connected to a Macintosh G4 computer. RBC (3 ml) suspended at 0.2% (vol/vol) in HBSS with $Ca^{2+}$, $Mg^{2+}$ were infused into the flow chamber and allowed to adhere to the slide for 10 min without flow. Before exposure to flow, a minimum of three fields at each of seven different locations along a line oriented normal to future flow were examined for the total number of fluorescent cells. Fluid flow (HBSS with $Ca^{2+}$, $Mg^{2+}$) was then started using a calibrated syringe pump. After exposure to flow, the fields were again examined and the number of adherent cells counted. The fraction of adherent cells was presented as (number of cells attached after exposure to flow)/(cells present per field before flow). The wall shear stress was calculated as:

$$\tau_w = \frac{6 \mu Q}{wH(x)^2}$$

$\tau_w$=wall shear stress (dyne/$cm^2$); Q=volumetric flow rate ($cm^3$/s); μ is media viscosity, w is the width of the flow channel, and H(x) is the height of the flow chamber as a function of position along the microscope slide. Several investigators have shown that blood flow in small vessels may be continuous, with shear stresses of 1-2 dynes/$cm^2$, or flow may be intermittent. Our data were obtained using both intermittent and continuous flow conditions.

$^{32}$P Erythrocyte Labeling, Anti-ICAM-4 Immunoprecipitation and Detection of Phosphorylation.

Packed RBCs depleted of endogenous ATP stores and $^{32}$P-labeled as previously described,[21] were incubated with phosphatase inhibitor cocktail (Sigma) in the presence or absence of MEKI U0126, PKAI, or a combination of both U0126 and PKAI, prior to 1 or 30 min treatment with epinephrine. Cells were then washed 4 times. ICAM-4 protein immunoprecipitation, and total and phospho-ICAM-4 detection were performed as previously described in detail.[4] To further confirm that the immunoprecipitates were specific for ICAM-4, anti-ICAM-4 mAb and the negative control immunoglobulin P3 were used to immunoprecipitate ICAM-4 from non-radiolabeled SS RBCs incubated in the presence or absence of epinephrine. Blots were then immunostained with anti-ICAM-4 mAb.

Whole Cell cAMP Accumulation:

Whole cell cAMP accumulation was assayed to assess the functional capacity of the RBC $\beta_2$-ARs to stimulate the production of cAMP. Washed packed RBCs were pre-treated with IBMX to define basal cAMP accumulation, followed by treatment with epinephrine for 1 min or 30 min, or forskolin. Samples were placed on ice, stimulation was halted, and cells fixed by the addition of 12.5 mM EDTA. Cell samples were boiled, clarified by centrifugation and assayed for cAMP content by radioimmunoassay as described previously.[22] Basal cAMP production was subtracted from the total cAMP produced by the cells. The amounts of cAMP were then normalized as fmol cAMP/$10^8$ RBCs.

Statistical Analysis.

Data were compared using parametric analyses (Graph-Pad Prism 4 Software, San Diego, Calif.), including repeated and non-repeated measures of analysis of variance (ANOVA). One-way ANOVA analyses were followed by Bonferroni corrections for multiple comparisons (multiplying the p value by the number of comparisons). A p value<0.05 was considered significant.

RBC Ghost Membrane Sample Preparation and Phosphopeptide Enrichment.

Ghosted RBCs were spun at 14,000 rpm for 15 min at 4° C. to pellet membranes. Membrane pellets were washed with 1 mL 50 mM ammonium bicarbonate (pH 8.0) with vortexing and were then spun at 14,000 rpm for 30 min at 4° C. The supernatant was then removed and 500 μL of 50 mM ammonium bicarbonate with μL 0.2% acid-labile surfactant (ALS-1) in 50 mM ammonium bicarbonate (pH 8.0) was added. Samples were subjected to probe sonication three-times for 5 sec with cooling on ice between and insoluble material was cleared by centrifugation at 14,000 rpm for 30 mins at 4° C. Samples were normalized to approximately 2 μg/μl following a micro-Bradford assay (Pierce Bioscience), and were reduced with a final concentration of 10 mM dithiothreitol at 80° C. for 20 min. Samples were then alkylated with a final concentration of 20 mM iodoacetamide at room temperature for 45 min and trypsin was added to a final ratio of 1-to-50 (w/w) enzyme-to-protein and allowed to digest at 37° C. for 18 hr. To remove ALS-1, samples were acidified to pH 2.0 with neat TFA, incubated at 60° C. for 2 hrs and spun at 14,000 rpm to remove hydrolyzed ALS-1. Samples were either subjected directly to LC-MS analysis or subjected to a $TiO_2$ based phosphopeptide enriched protocol.

To enrich for phosphorylated peptides prior to LC-MS analysis, either 1,125 μg and 970 μg of total digested protein from RBC ghosts co-incubated with recombinant active ERK2 experiments and experiments using epinephrine-treated cells, respectively, were brought to near dryness using vacuum centrifugation and then resuspended in 200 μL of 80% acetonitrile, 1% TFA, 50 mg/ml MassPrep Enhancer (pH 2.5) (Waters Corp. Milford, Mass.). Samples were loaded onto an in-house packed $TiO_2$ spin column (Protea Biosciences) with a 562 μg or 485 μg binding capacity for active ERK2 treated or epinephrine treated experiments, respectively. Samples were washed twice with 200 μL 80% acetonitrile, 1% TFA, 50 mg/ml MassPrep Enhancer (pH 2.5) followed by two washes with 200 μL 80% acetonitrile, 1% TFA (pH 2.5). Retained peptides were eluted twice with 100 μL 20% acetonitrile, 5% aqueous ammonia (pH 10.0), acidified to pH 3 with neat formic acid and then brought to dryness using vacuum centrifugation. Prior to LC-MS analysis, each sample was resuspended in 20 μL 2% acetonitrile, 0.1% TFA, 25 mM citric acid (pH 2.5).

Label-Free Quantitative Phosphoproteomic Analysis of RBC Ghost.

Chromatographic separation of phosphopeptide enriched or non-enriched samples was performed on a Waters NanoAquity UPLC equipped with a 1.7 μm BEH130 $C_{18}$ 75 μm I.D.×250 mm reversed-phase column. The mobile phase consisted of (A) 0.1% formic acid in water and (B) 0.1% formic acid in acetonitrile. Five μL injections of each sample were trapped for 5 min on a 5 μm Symmetry $C_{18}$ 180 μm I.D.×20 mm column at 20 μl/min in 99.9% A. The analytical column was then switched in-line and the mobile phase was held for 5 min at 5% B before applying a linear elution gradient of 5% B to 40% B or 5% B to 30% B over 90 min at 300 nL/min for ERK2 treated experiments or epinephrine treated experiments, respectively. The analytical column was connected to fused silica PicoTip emitter (New Objective, Cambridge, Mass.) with a 10 μm tip orifice and coupled to the mass spectrometer through an electrospray interface.

MS data from each phosphopeptide enriched sample was acquired on a Thermo LTQ-Orbitrap XL mass spectrometer operating in positive-ion mode with an electrospray voltage of 2.0 kV with real-time lockmass correction on ambient polycyclodimethylsiloxane (m/z 445.120025) enabled. The instrument was set to acquire a precursor MS scan from m/z 400-2000 with r=60,000 at m/z 400 and a target AGC setting of 1e6 ions. Each sample was analyzed four-times, one of which was used for additional qualitative identifications only and was not included in the quantitative analysis, with product ions above a threshold of 500 counts were acquired for the top 5 most intense ions in the linear ion trap. Maximum fill times were set to 1000 ms for full MS scans acquired in the OT and 250 ms for MS/MS acquired in the linear ion trap, with a CID energy setting of 35% and a dynamic exclusion of 60 s for previously fragmented precursor ions. Multistage activation (MSA) for neutral losses of 98.0, 49.0, and 32.33 Da was enabled to enhance fragmentation of phosphorylated peptides. MS data for non-phosphopeptide enriched samples was acquired on a Waters Synapt HDMS operating in positive-ion mode with an electrospray voltage of 3.0 kV. Each sample was analyzed three times in a data-independent ($MS^E$) mode of acquisition with 0.9 sec cycle times alternating between low collision energy (6 V) and high collision energy ramp (15 to 40 V). One additional data-dependent (DDA) analysis using a 0.9 sec MS scan followed by MS/MS acquisition on the top 3 ions with charge greater than 1 was acquired to increase the number of qualitative identifications. MS/MS scans for each ion used an isolation window of approximately 3 Da, a maximum of 4 seconds per precursor, and dynamic exclusion for 120 seconds within 1.2 Da.

Label-free quantitation and integration of qualitative peptide identifications was performed using Rosetta Elucidator (v 3.3, Rosetta Inpharmatics, Seattle, Wash.). All raw LC-MS/MS data within an experiment were imported and subjected to chromatographic retention time alignment using the PeakTeller® algorithm with a minimum peak time width set to 6 s, alignment search distance set to 4 min and the refine alignment option enabled. Quantitation of all measurable signals in the precursor MS spectra (excluding LC-MS analysis intended only for additional qualitative identifications), was performed by Elucidator by calculating either peak volume (area under curve) for Synapt HDMS data files or peak height for LTQ-Orbitrap data files.

Qualitative peptide identifications from all phosphopeptide enriched samples and DDA analysis of non-phosphopeptide enriched samples were made by generating DTA files for all precursor ions, which had associated MS/MS spectra. DTA files were submitted to Mascot (Matrix Science, Boston, Mass.) and searched against a *Homo sapien* protein database downloaded from SwissProt concatenated with the sequence-reversed version of each entry. $MS^E$ data were independently processed within ProteinLynx Global Server 2.4 (Waters Corp) and searchable files were then submitted to the IdentityE search engine (Waters Corp). Search tolerances of 20 ppm precursor and 0.8 Da product ions were applied for LTQ-Orbitrap data and 20 ppm precursor and 0.04 Da product ions were applied for Synapt HDMS data files with lock-mass correction on m/z 785.8426 (doubly-charged Glu-1-Fibrinopeptide ion) enabled. All data were searched using trypsin specificity with up to two missed cleavages with a static modification of Carbamidomethylation (+57.0214 Da on C) and dynamic modifications of oxidation (+15.9949 Da on M). Dynamic search modifications of phosphorylation (+79.9663 Da on STY) and of deamidation (+1.008 Da on NQ) were employed for phosphopeptide enriched sample and non-phosphopeptide enriched samples, respectively. Peptides FDR were determined by adjusting the Mascot peptide ion score threshold to allow a 1% occurrence of peptides from reverse protein entries for phosphopeptide enriched experiments, or by using PeptideProphet algorithim scores which corresponded to a 2% peptide false discovery rate for non-phosphopeptide enriched experiments.

Database search results and spectra have been uploaded in the form of Scaffold 3 files (.sf3, Proteome Software, Inc) to the Tranche database (https://proteomecommons.org/tranche/) under the group "RBC Ghost Membrane Phosphoproteome" with the following links (if a password is requested, it is rbcphos).

Mice:

All animal experiments were carried out in accordance with protocols approved by the Duke University Animal Care and Use Committee. Female athymic homozygous nude mice (nu-/nu-) were between 8-12 weeks of age (Charles River Laboratories, Wilmington, Mass.).

Window Chamber Surgery:

General anesthesia was achieved by intra-peritoneal injection of 100 mg/kg of ketamine (Abbott Laboratory, Chicago, Ill.) and 10 mg/kg of xylazine (Bayer, Shawnee Mission, Kans.). A double-sided titanium frame window chamber was surgically implanted into the dorsal skin fold under sterile conditions using a laminar flow hood. Surgery involved carefully removing the epidermal and dermal layers of one side of a dorsal skin fold, exposing the blood vessels of the subcutaneous tissue adjacent to the striated muscles of the opposing skin fold, and then securing the two sides of the chamber to the skin using stainless steel screws and sutures. A glass window was placed in the chamber to cover the exposed tissue and secured with a snap ring. Subsequently, animals were kept at 32-34° C. until in vivo studies were performed 3 days post-surgery.

RBC Infusions and Intravital Microscopy:

Murine recombinant TNF-α was dissolved in normal saline at a concentration of 0.1 mg/mL and mice bearing dorsal-skin window chamber implants were given a single intraperitoneal (IP) injection of 20 μg/kg TNF-α and control animals received same volume of normal saline. Three hours and 30 min following TNF-α administration, either placebo

[0.4% dimethyl sulfoxide (DMSO) in normal saline] or U0126 (Cell Signaling Technology) (2 and 0.2 mg/kg, in 0.4% and 0.04% DMSO, respectively) was injected intravenously via tail vein of anesthetized animals. Thirty minutes later, labeled human SS RBCs (300 μl hematocrit (Hct) 50% in PBS with $Ca^{2+}$ and $Mg^{2+}$) were then infused. In some experiments, animals administered with TNF-α were infused 4 hours later with washed SS RBCs sham-treated or treated with 10 μM U0126 or 10 μM RDEA119 for 1 hour. Animals were placed on the stage of an Axoplan microscope (Carl Zeiss, Thornwood, N.Y.); temperature was maintained at 37° C. using a thermostatically controlled heating pad. RBC adhesion and blood flow dynamics were observed in subdermal vessels for at least 30 minutes using 20× and 10× magnifications. Microcirculatory events and cell adhesion were simultaneously recorded using a Trinitron Color video monitor (PVM-1353 MD, Sony) and JVC videocassette recorder (BR-53784, VCR King, Durham, N.C.) connected to a digital video camera C2400 (Hamamatsu Photonics K.K., Japan). Arterioles were distinguished from venules based on: 1) observation of divergent flow as opposed to convergent flow; 2) birefringent appearance of vessel walls using transillumination, which is characteristic of arteriolar vascular smooth muscle; and 3) relatively straight vessel trajectory without evidence of tortuosity. Cell adherence was quantitated by considering cells attached to the vessel walls and immobile for 1 minute. The percentage of the length of vessels with diameters≤25 μm or >25 μm, occupied by SS RBCs was quantified as: % venular length occupied by SS RBCs=length of vessel wall with adherent cells/total length of the vessel segments analyzed×100.

Figure 1B:
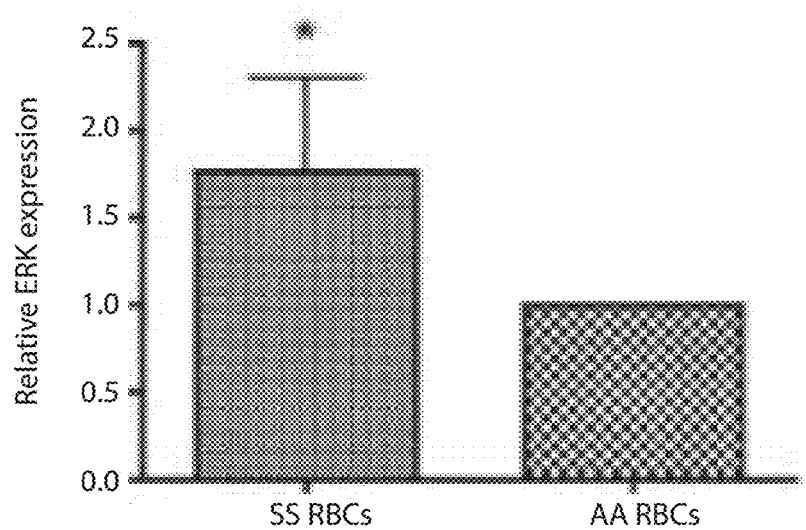

Example 2: ERK1/2 is Present in Mature RBCs and Undergoes Activation by Epinephrine in SS but not Normal RBCs Recently, our preliminary data showed that ERK1/2 can be found bound to the RBC plasma membrane. The cAMP/PKA pathway is known to both activate SS RBCs to adhere abnormally to endothelial cells (ECs)[4] and modulate the MAPK/ERK cascade. Given the importance of abnormal SS RBC adherence in SCD pathophysiology, we investigated the possibility that ERK activity is conserved in SS RBCs and inducible by epinephrine. RBC ghosts consisting of membrane fragments prepared from SS and normal (AA) RBCs were first analyzed to confirm the presence of ERK1/2 and MEK1/2, the upstream kinase of ERK1/2 activation. MEK1/2 was abundant in both SS and AA RBCs, while ERK1/2 was expressed at higher levels in SS vs AA RBCs (p<0.05, FIG. 1A and FIG. 1B). Since ERK1/2 is also well expressed by platelets and leukocytes, we examined our RBC suspensions for contamination by other blood cells. Our SS RBC preparations (0.13±0.01×10⁶/ml RBCs) showed no contamination by platelets, but a very low level of contamination by leukocytes (0.2±0.06×10³/ml) was sometimes detected. However, when similar numbers of isolated sickle cell patient leukocytes were examined for the presence of ERK1/2, no detectable signal was observed (data not shown), making it apparent that the observed ERK signal was in fact derived from SS RBCs.

Figure 1C:
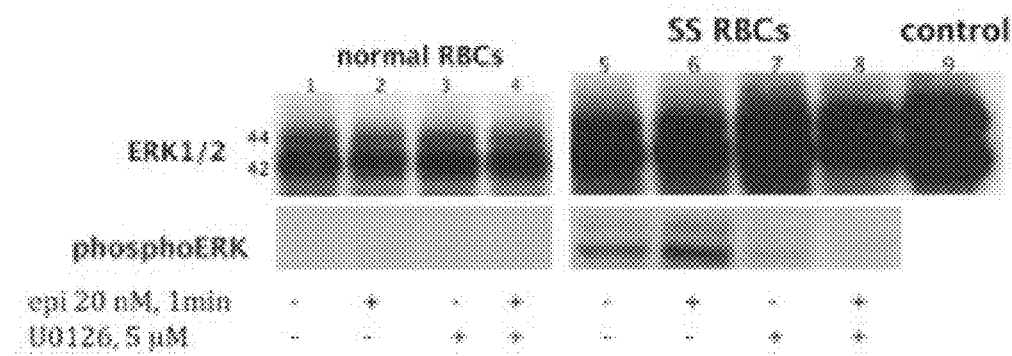
Figure 1D:
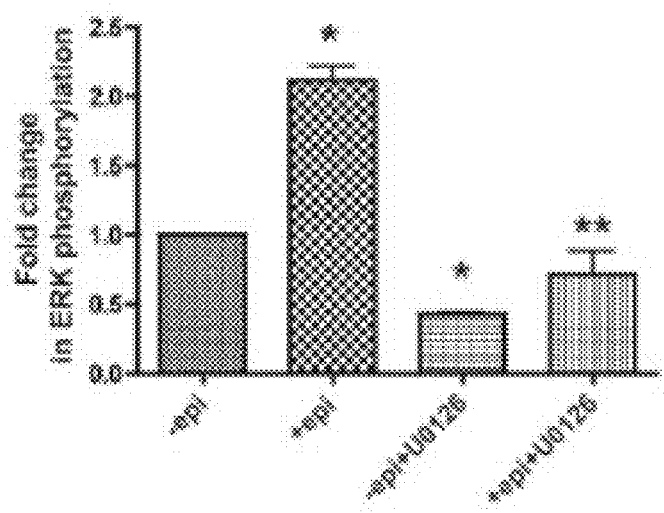

Our data also indicated that ERK1/2 is phosphorylated at baseline in SS RBCs, and epinephrine at a physiologic "stress" dose (20 nM)[29] promoted a 2.1±0.1-fold increase in ERK phosphorylation within 1 minute (n=3; p<0.001) (FIGS. 1C and 1D). Incubation of SS RBCs with the MEKI U0126, which specifically inhibits MEK1/2, prior to epinephrine treatment, significantly inhibited the effect of epinephrine on ERK1/2 phosphorylation (p<0.001) (FIGS. 1C and 1D). Because our previous data indicated that the degree of adhesive response to epinephrine stimulation varied from patient to patient,[4] the effect of epinephrine on ERK phosphorylation was measured in samples obtained from a larger group of patients (n=19). Although a statistically significant increase (2±0.17-fold) in ERK phosphorylation above basal levels was observed (P<0.05), SS RBCs from only 40% of patients exhibited more than 1.5-fold elevation in ERK phosphorylation by epinephrine. These patients were classified as responders. This data suggests that not all SCD patients are susceptible to epinephrine-stimulated increased ERK phosphorylation. In contrast, ERK1/2 was never found phosphorylated in AA RBCs and failed to undergo phosphorylation by epinephrine (FIG. 1C). In contrast, ERK1/2 was never found phosphorylated in normal (AA) RBCs at baseline and also failed to undergo phosphorylation after epinephrine stimulation (FIG. 1C).

Figure 1E:
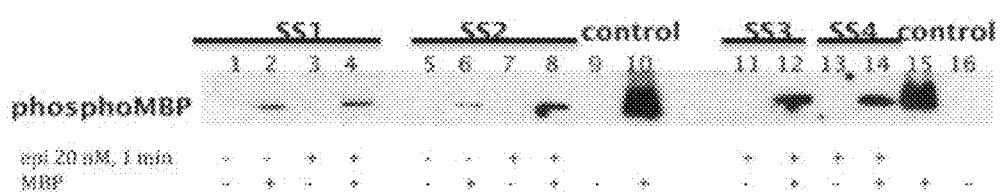
Figure 1F:
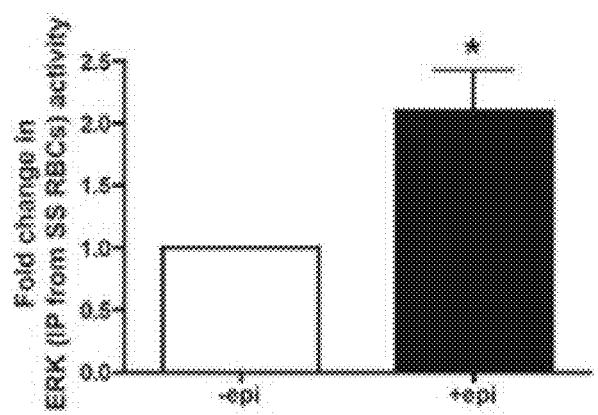

To further confirm that ERK1/2 preserved its activity in SS RBCs and that phosphorylation was indeed an indicator of ERK activation, we used the ERK specific substrate, myelin basic protein (MBP), to test the activity of ERK1/2 isolated from both sham-treated and epinephrine-treated SS RBCs, in the presence of inhibitors of PKA, PKC, $Ca^{2+}$/calmodulin-dependent kinase and p34$^{cdc2}$ kinase to prevent nonspecific phosphorylation of MBP by these enzymes.[24] ERK1/2 immunoprecipitated from sham-treated SS RBCs was capable of phosphorylating MBP to some extent, while MBP phosphorylation by ERK1/2 immunoprecipitated from epinephrine-treated SS RBCs increased 2.1±0.3-fold compared to MPB phosphorylation induced by ERK1/2 isolated from sham-treated cells (n=4; p=0.0286) (FIGS. 1E and 1F). These data indicate that ERK1/2 can be already somewhat activated in SS RBCs and that epinephrine can augment its activity.

Example 3: ERK1/2 in SS RBCs Acts Downstream of the cAMP/PKA Signaling Pathway

Figure 2A:
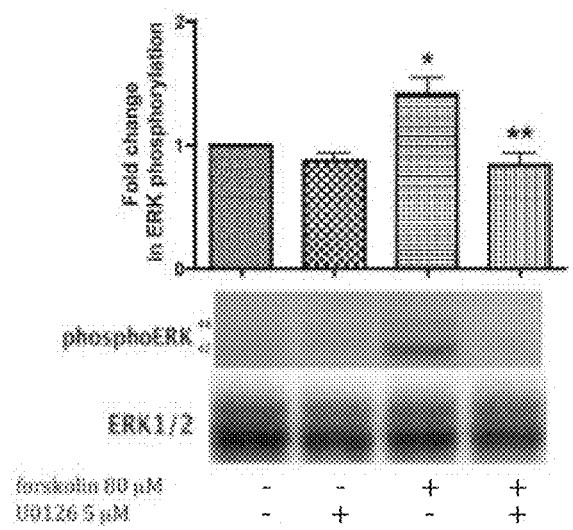
FIG. 2A to 2E shows that ERK activation in SS RBCs involves the cAMP/PKA pathway and the tyrosine kinase p72$^{syk}$ and is sensitive to the effect of Gα$_i$ protein. SS RBCs (FIG. 2A, FIG. 2B, FIG. 2C and FIG. 2D), and reticulocyte-enriched and -depleted (mature) SS RBCs (FIG. 2E) were sham-treated, treated with forskolin (FIG. 2A), epi (FIG. 2B and FIG. 2C), the protein kinase A inhibitor (PKAI), 14-22 amide, (FIG. 2B), or Pertussis toxin (PTx) (FIG. 2C and FIG. 2D) in the presence or absence of the MEK inhibitor (MEKI) U0126 (FIG. 2A, FIG. 2B and FIG. 2D), piceatannol (FIG. 2D) or damnacanthal (FIG. 2D). RBC proteins were blotted with antibodies against ERK and phosphoERK. Quantitative analysis of the blots is presented as fold change in ERK phosphorylation.

We found that treatment of SS RBCs with forskolin, which directly activates AC to produce cAMP, promoted increased ERK1/2 phosphorylation, which was in turn prevented by MEKI U0126, suggesting that cAMP is needed for ERK activation in SS RBCs (FIG. 2A).

Figure 2B:
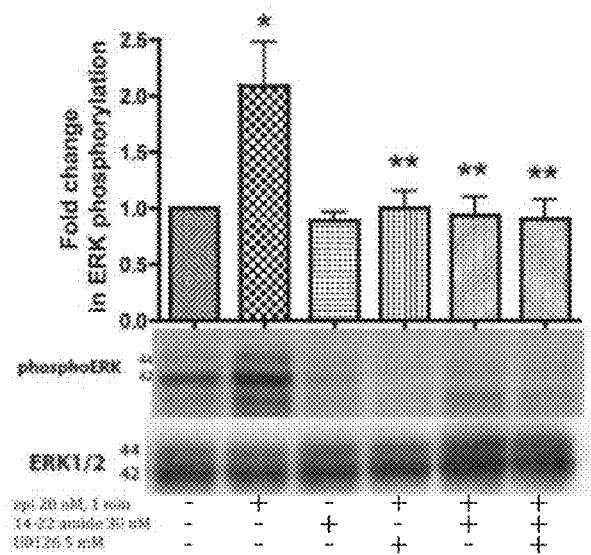

To determine the role of PKA in ERK phosphorylation, we used the PKA-specific inhibitor (PKAI), 14-22 amide. Treatment of SS RBCs with the PKAI, 30 nM 14-22 amide, at a concentration known to promote optimal inhibition of PKA in SS RBCs, did not significantly decrease basal ERK phosphorylation in these sickle cells (FIG. 2B). However, PKAI completely blocked the effect of epinephrine on ERK phosphorylation (p<0.01, n=3). Pre-treatment of SS RBCs with a combination of PKAI and MEKI U0126 also completely blocked ERK phosphorylation in response to epinephrine stimulation (p<0.01) (FIG. 2B). Together these data suggest that ERK1/2 activation in SS RBCs is dependent on the cAMP/PKA pathway.

Figure 2C:
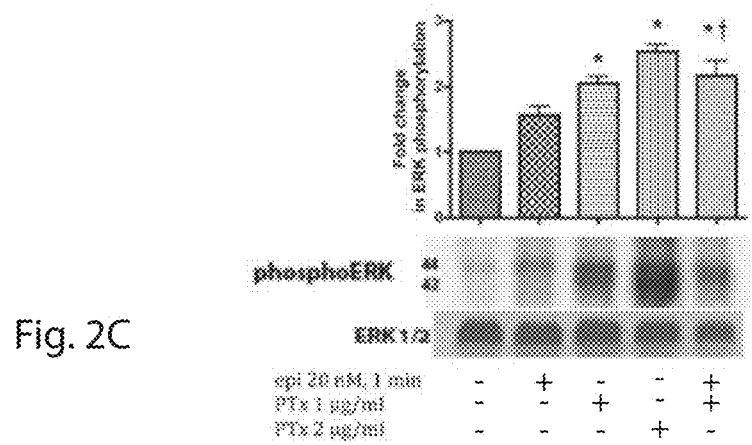

In some instances, $\beta_2AR$ activation employs a $G\alpha_i$ (or $G\alpha_o$) pathway to stimulate ERK activity.[7] We investigated whether epinephrine stimulated SS RBC $\beta_2ARs$ mediated ERK activation also involved the $G\alpha_i$, using Pertussis toxin (PTx), which inhibits $G\alpha_i$-signaling. Inhibition of $G\alpha_i$ with 1 or 2 μg/ml PTx alone significantly increased basal phosphorylation of ERK1/2 by 2.04±0.1- and 2.53±0.11-fold, respectively and combining PTx with epinephrine had no additional effect (FIG. 2C, p<0.001). These results suggest that increased ERK1/2 phosphorylation in SCD patient samples tested is negatively affected by $G\alpha_i$ activation, or due to the direct actions of PTx.

Figure 2D:
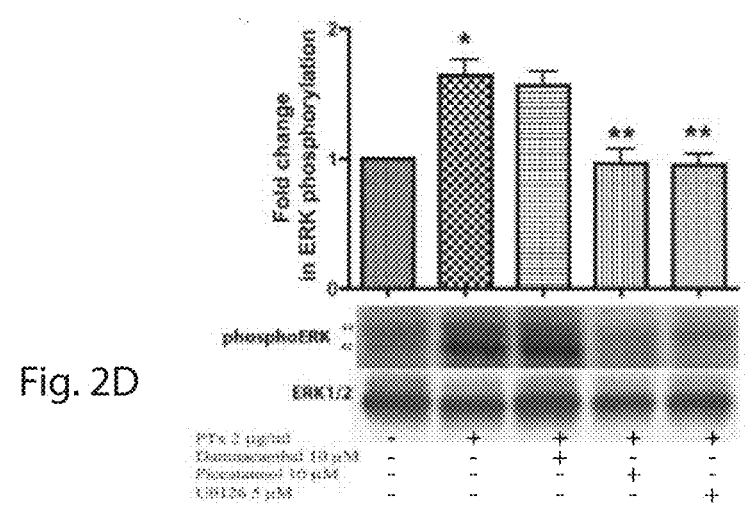

Because direct or indirect involvement of cytoplasmic tyrosine kinases in activation of MAP kinase cascades has also been demonstrated,[25, 26] we evaluated the contribution of tyrosine kinase-induced signaling to RBC ERK1/2 phosphorylation. ERK1/2 was phosphorylated at baseline in sham-treated SS RBCs (FIG. 2D). Treatment with 2 µg/ml PTx markedly increased ERK1/2 phosphorylation. Damnacanthal, a highly potent and selective inhibitor of the tyrosine kinase $p56^{lck}$,[27] did not abrogate ERK phosphorylation in response to PTx (FIG. 2D). However, piceatannol, which preferentially inhibits the tyrosine kinase $p72^{syk}$ vs $p56^{lyn}$, completely blocked the effect of PTx on ERK phosphorylation. Once more, U0126 blocked the effect of PTx on ERK1/2 phosphorylation. These data suggest that the piceatannol-sensitive tyrosine kinase $p72^{syk}$ also plays a role in SS RBC ERK1/2 activation.

Figure 2E:
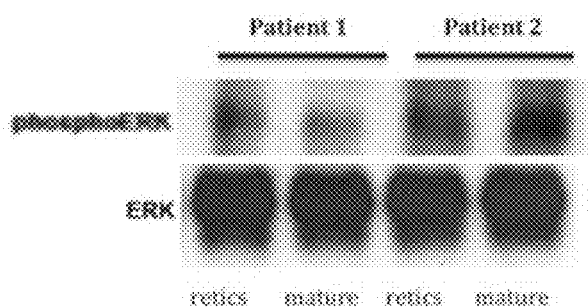

To determine if ERK1/2 is active only in the youngest cell population (reticulocytes), reticulocyte-enriched and -depleted (mature) SS RBCs were analyzed for kinase phosphorylation. Flow cytometric analysis showed that up to 15% of unseparated SS RBCs expressed the transferrin receptor, a reticulocyte marker. After separation, more than 95% of the reticulocyte-enriched cells expressed the transferrin receptor, while the reticulocyte-depleted population reacted with the anti-transferrin receptor antibody no more strongly than with the negative control immunoglobulin (data not shown). ERK1/2 was strongly phosphorylated in both reticulocyte-enriched and reticulocyte-depleted cells (n=2) (FIG. 2E), suggesting that ERK activity is preserved in both reticulocytes and mature SS RBCs.

Example 4: ERK1/2 is Involved in SS RBC Adhesion to Endothelial Cells

Figure 3A:
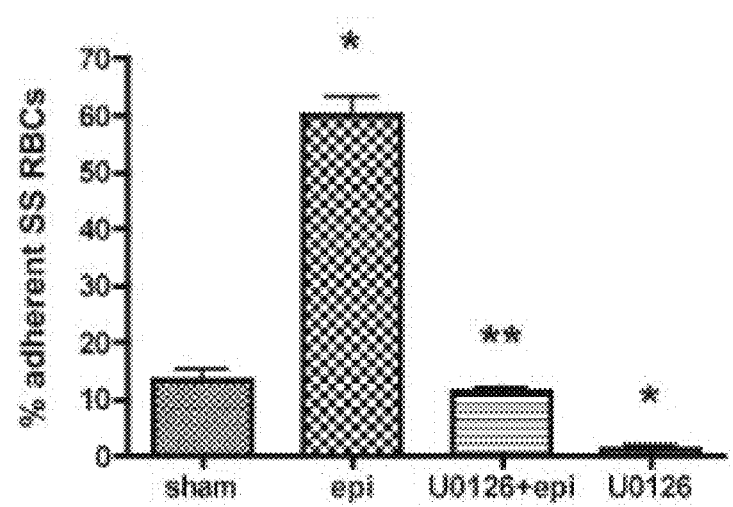
FIG. 3A-3D shows that ERK signaling modulates both SS RBC adhesion to endothelial cells and ICAM-4 phosphorylation.

Since the pharmacological agents epinephrine and forskolin modulate both SS RBC adhesion to ECs[4] and ERK activation, we determined the contribution of MEK/ERK signaling to RBC adhesion. Epinephrine significantly up-regulated SS RBC adhesion to HUVECs at a shear stress of 2 dynes/cm² in intermittent flow condition assays (p<0.001) (FIG. 3A). However, U0126 completely inhibited the effect of epinephrine on SS RBC adhesion (p<0.001). Treatment of SS RBCs with U0126 alone also blocked SS RBC adhesion to HUVECs (91±4.6% inhibition) when compared to adhesion of sham-treated SS RBCs (p<0.01).

Figure 3B:
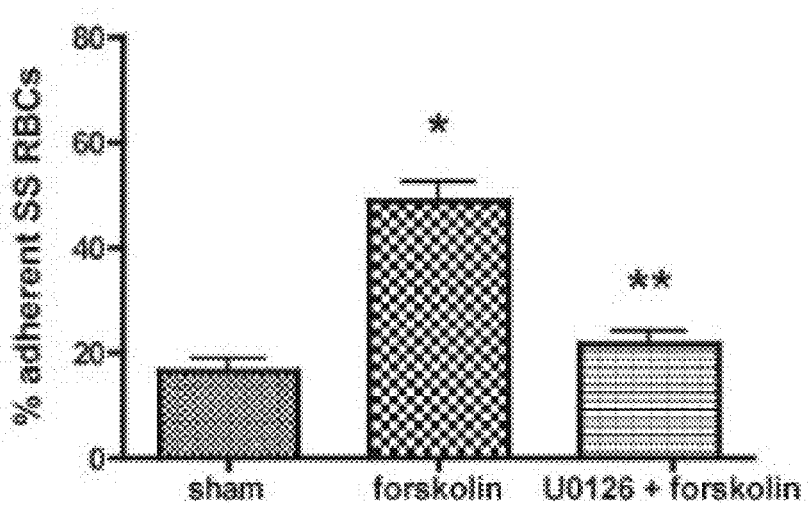

Forskolin also enhanced SS RBC adhesion to HUVECs at a shear stress of 2 dynes/cm² (p<0.001, n=3) (FIG. 3B), and this effect was blocked by U0126 (83±4% inhibition, compared to increased adhesion by forskolin alone; p<0.01). This suggests that the MEK/ERK pathway contributes to up-regulation of SS RBC adhesive function to ECs.

Example 5: ERK Signaling is Implicated in Phosphorylation of the RBC Adhesion Receptor ICAM-4 (Landsteiner-Wiener Blood Group Antigen, LW)

Figure 3C:
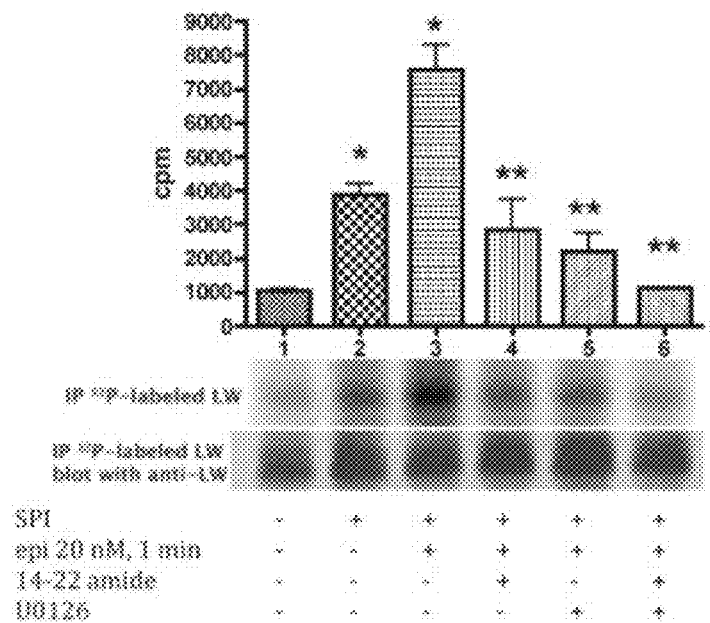

We further explored the possibility that the ERK signaling pathway is involved in ICAM-4 (LW) phosphorylation, which mediates adhesion via binding to endothelial $\alpha v\beta 3$ integrin.[4] The ICAM-4 protein possesses only one serine, one tyrosine and no threonine within the 12 amino acids of its cytoplasmic tail, and it does not contain a typical PKA target consensus motif. Nevertheless, up-regulation of SS RBC adhesion to non-activated ECs requires serine phosphorylation of the ICAM-4 receptor.[4] PhosphorImager analysis of immunoprecipitated ³²P-radiolabeled ICAM-4 and negative control immune complexes showed that ICAM-4 of non-stimulated SS RBCs (FIG. 3C, lane 1) is modestly phosphorylated as previously shown. Treatment of SS RBCs with serine phosphatase inhibitors (SPI) (lane 2) increased ICAM-4 phosphorylation by 3.7±0.46-fold (p<0.05, n=3), suggesting that increased ICAM-4 phosphorylation is a result of serine phosphorylation, as tyrosine phosphatase inhibitors were not present. These were similar to the effects of epinephrine, although SPI-stimulation induced a significant increase (2.62±0.6-fold) in ICAM-4 phosphorylation above baseline in a larger group of patients (n=8) (P<0.05), only half of all SS RBC samples exhibited≥2-fold elevation in ICAM-4 phosphorylation in response to SPI. Epinephrine in the presence of SPI had a stronger effect on ICAM-4 phosphorylation (7.4±1.07-fold increase over sham-treated SS RBCs; p<0.001) (lane 3). Treatment of SS RBCs with either the PKAI or U0126 (lanes 4 and 5, respectively) significantly decreased the combined effect of epinephrine and SPI on ICAM-4 phosphorylation compared to cells treated with epinephrine alone (p<0.001) (lane 3). Treatment of SS RBCs with both PKAI and MEKI completely blocked epinephrine and SPI from up-regulating phosphorylation of ICAM-4 (p<0.001) (FIG. 3C, lane 6).

Figure 3D:
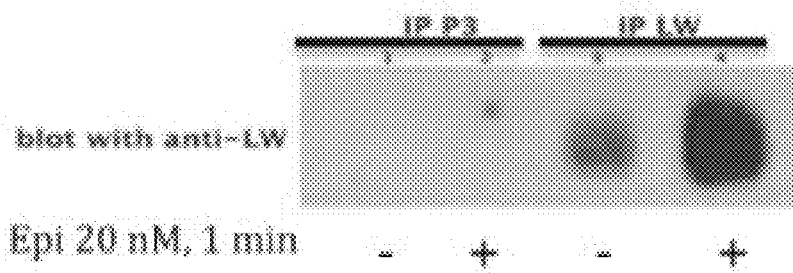

Immunoblots of ³²P-radiolabeled ICAM-4 immunoprecipitates from stimulated and non-stimulated SS RBCs (FIG. 3C) indicated that a similar amount of ICAM-4 was immunoprecipitated from these cells. Control immunoblots of immunoprecipitated ICAM-4 and the negative control complexes immunoprecipitated with P3 from stimulated and non-stimulated SS RBCs are shown in FIG. 3D.

To define whether ICAM-4 is a substrate for ERK, we used non-treated packed normal RBCs as a source of ICAM-4, since ERK is inactive in these cells (FIG. 1A-1F) and ICAM-4 is not phosphorylated at baseline.[4] Exposure of immunoprecipitated ICAM-4 to active recombinant ERK2 did not cause ICAM-4 phosphorylation, indicating that ICAM-4 is not a substrate for ERK (data not shown). Together, our data demonstrate that ICAM-4 in SS RBCs undergoes serine phosphorylation by a yet unknown kinase, and this process is PKA and MEK/ERK1/2 dependent.

Figure 4A:
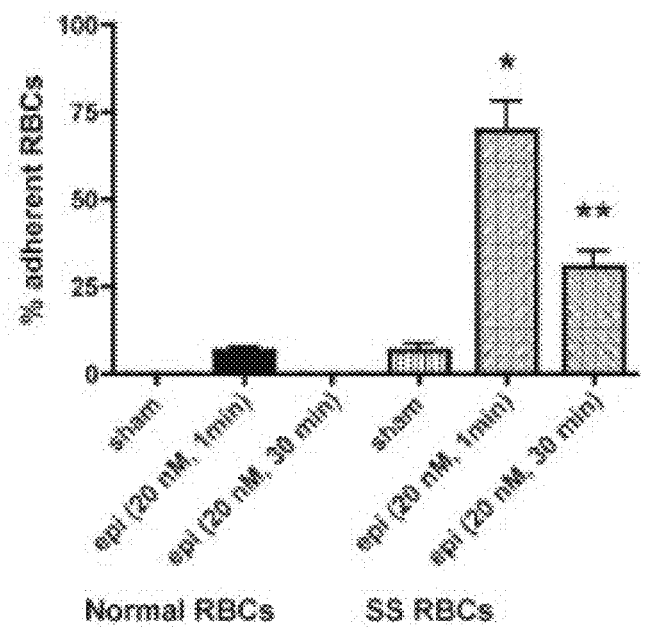
FIG. 4A-4G show SS RBC adhesion is associated with the extent of ERK activation.
Figure 4B:
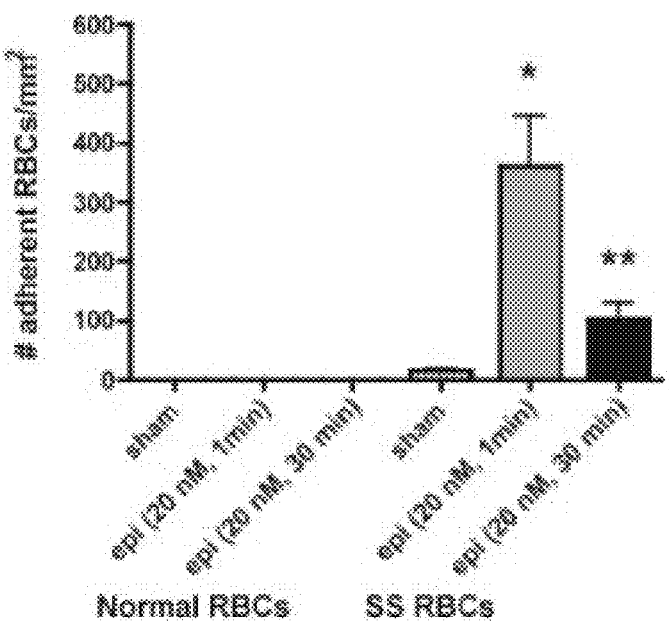

Example 6: SS RBC Adhesion is Strictly Related to the Inception of ERK Activation Epinephrine significantly increased SS RBC adhesion to HUVECs under both intermittent and constant flow conditions after 1 min exposure (p<0.001 for each), while adhesion decreased after 30 min cell exposure to epinephrine (mean decrease of all samples=56±1.5% and 73±4.7% for intermittent and constant flow conditions, respectively; p<0.001 for each) (FIGS. 4A and 4B). In contrast, epinephrine treatment for either 1 or 30 min had minimal effect on normal RBC adhesion to HUVECs under either intermittent or constant flow conditions (FIGS. 4A and 4B).

Figure 4C:
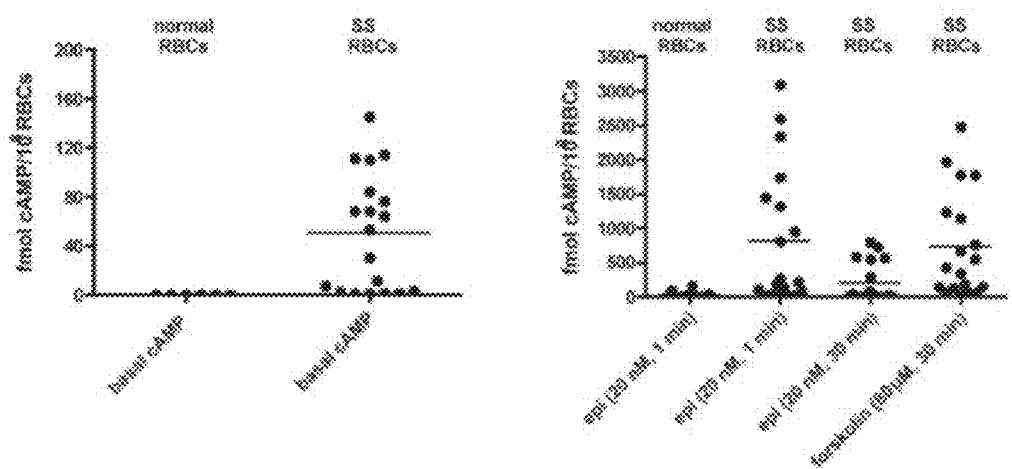

We also examined the effect of exposure time of SS RBCs to epinephrine on cAMP production, which appears to act upstream of ERK1/2. Basal cAMP in normal RBCs from healthy donors was significantly lower than basal cAMP in SS RBCs (p=0.0187) (FIG. 4C). In about 50% of the samples examined (n=19), incubation of SS RBCs with epinephrine for 1 min resulted in accumulation of high levels of intracellular cAMP comparable to the levels of cAMP induced by forskolin treatment for 30 min. Although the cAMP response to epinephrine (1 min exposure time) varied among patients, as previously described,[28] cAMP levels uniformly declined with 30 min exposure time of SS RBCs to epinephrine (p<0.05) (FIG. 4C). Epinephrine exposure for 1 min had lower effect on cAMP accumulation in normal RBCs (n=12) than in SS RBCs (FIG. 4C) as previously shown.

Figure 4D:
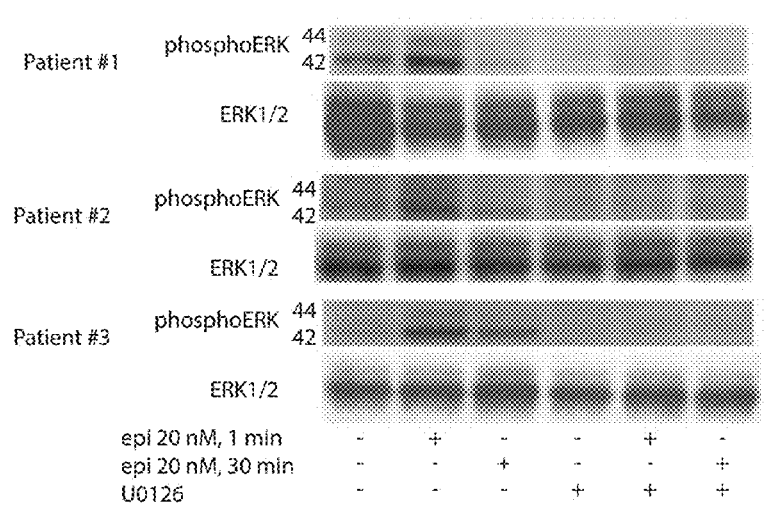
Figure 4E:
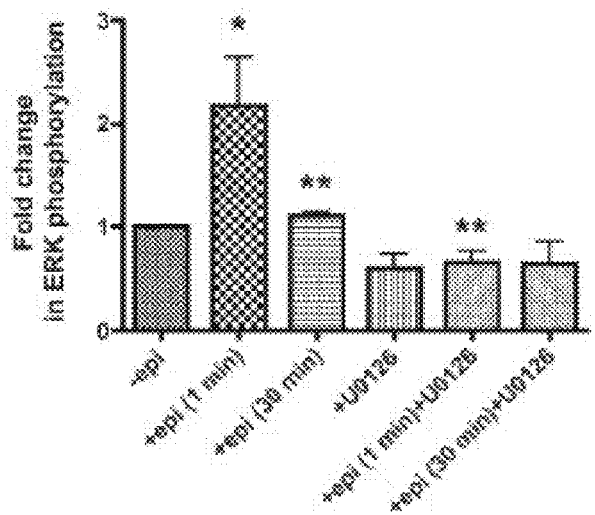

Additionally, while a 1 min exposure of SS RBCs to epinephrine markedly increased ERK phosphorylation (p<0.01 for epinephrine-treated for 1 min vs sham-treated), ERK phosphorylation decreased after a 30 min exposure (p<0.01 for epinephrine-treated for 1 min vs 30 min) to levels observed in sham-treated cells (p>0.05 for epinephrine-treated for 30 min vs sham-treated) (FIGS. 4D and 4E).

Figure 4F:
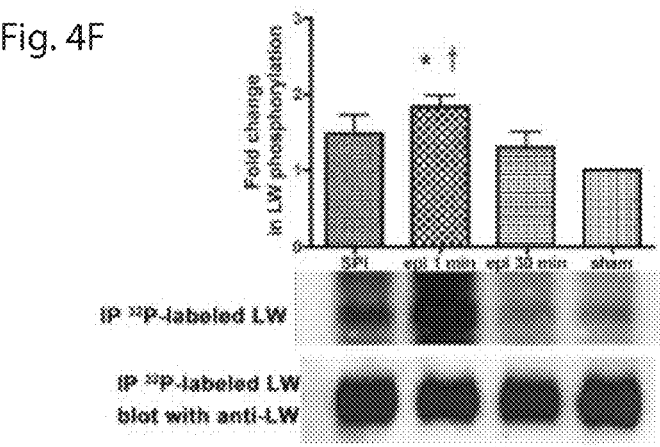

ICAM-4 phosphorylation also decreased with longer exposure time (30 min vs 1 min) of SS RBCs to epinephrine (FIG. 4F). PhosphorImager analysis of immunoprecipitated $^{32}$P-radiolabeled ICAM-4 and negative control immune complexes showed that treatment of SS RBCs with epinephrine for 1 min in the presence of SPI (lane 2) enhanced ICAM-4 phosphorylation by 1.84±0.15-fold over sham-treated cells (lane 4, p<0.01). Thirty minutes exposure of SS RBCs to epinephrine in the presence of SPI (lane 3) significantly diminished the effect of epinephrine and SPI on ICAM-4 phosphorylation compared to cells treated with epinephrine for 1 min (lane 2, p<0.05). Altogether, these data indicate that exposure time to epinephrine influences all these downstream effects—SS RBC adhesion, cAMP levels and phosphorylation of both ERK1/2 and ICAM-4—in a parallel fashion, suggesting that the time course of up-regulation of ICAM-4-mediated SS RBC adhesion is closely associated to the extent of ERK1/2 activation.

Figure 4G:
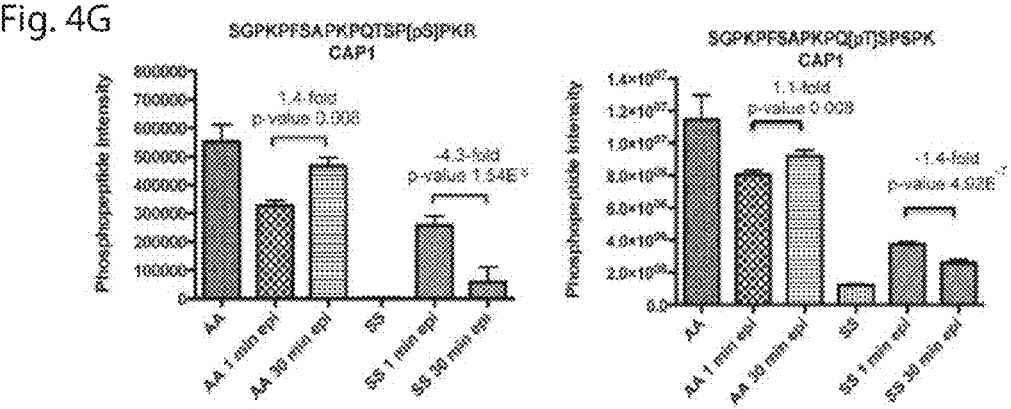

To identify potential proteins involved in regulation of the ERK pathway, a label-free quantitative phosphoproteomics analysis of RBC ghosts isolated from SS and normal RBCs treated with epinephrine for 1 and 30 min was undertaken. SS RBCs treated with epinephrine for 30 min showed a dramatic decrease in phosphorylation of serine 310 within adenylate cyclase-associated protein 1 (CAP1) compared to cells stimulated with epinephrine for 1 min (−4.3-fold, p=1.54×10$^{-5}$) (FIG. 4G). Conversely, AA RBCs exposed to epinephrine for 30 min showed an enhancement in phosphorylation of the CAP1serine vs 1 min epinephrine exposure (+1.4-fold, p=0.008). Threonine 307 within CAP1 also underwent a smaller yet statistically significant decrease in phosphorylation in SS RBCs exposed to epinephrine for 30 min vs 1 min epinephrine exposure (−1.4-fold, p=4.92×10$^{-7}$). Our data indicate that exposure to epinephrine for a prolonged period of time negatively affects phosphorylation of CAP1 in SS but not in AA RBCs. Adenylate cyclase-associated proteins (CAPs) are known to regulate AC activation to increase cAMP levels under specific environmental conditions. We therefore suggest that a decrease in CAP1 phosphorylation in SS RBCs might down-regulate AC activity in these cells, negatively affecting signaling downstream of ERK.

Example 7: ERK Signaling Pathway is Implicated in Phosphorylation of Protein 4.1

Figure 5:
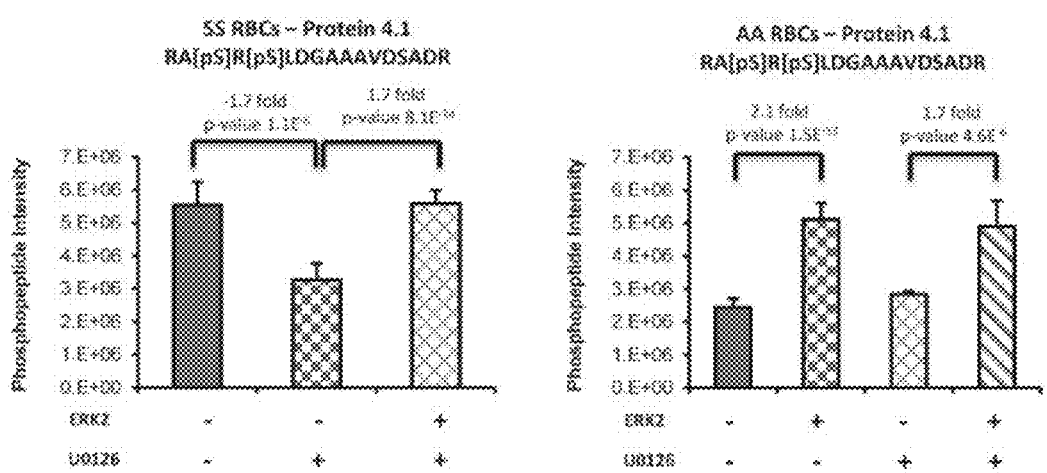
FIG. 5. Phosphorylation of protein 4.1 is induced via the ERK signaling pathway. Sham-treated or U0126-treated SS and normal (AA) RBCs ghosts co-incubated with or without recombinant active ERK2 (ERK2) were enriched in phosphopeptides, followed by a label-free quantitative phosphoproteomics analysis. Treatment of SS RBCs with U0126 caused a significant decrease in doubly phosphorylated peptide within protein 4.1. Addition of ERK2 to the U0126-treated SS RBC ghosts increased the abundance of this phosphopeptide back to levels observed in untreated SS RBCs. The complementary trend for this phosphorylated peptide was also observed upon the addition of ERK2 to AA RBCs sham-treated or U0126-treated.

A label-free quantitative phosphoproteomics analysis was also performed to identify additional putative downstream targets of ERK by adding recombinant active ERK2 to RBC ghosts isolated from SS and normal RBCs. Because endogenous ERK is active at baseline in SS but not normal RBCs (FIG. 1A-1F), SS RBCs were treated with U0126 prior to incubation of the ghosts with recombinant ERK2. We found that phosphorylation of protein 4.1 was induced in the presence of recombinant ERK2. Treatment of SS RBCs with U0126 resulted in a significant decrease (−1.7-fold, p=1.01×10$^{-6}$) of a Ser540/Ser542 doubly phosphorylated peptide within protein 4.1 (FIG. 5). Addition of recombinant ERK2 to the U0126-treated SS RBC ghosts increased the abundance of this phosphopeptide (+1.7-fold, p=8.06×10$^{-14}$) back to levels observed in untreated SS RBCs, indicating the specificity of ERK2 as the upstream kinase. As expected, treatment of AA RBCs with U0126 did not induce a decrease of this doubly phosphorylated peptide within protein 4.1, since endogenous ERK is inactive in these cells. However, the complementary trend for this phosphorylated peptide was observed upon the addition of recombinant ERK2 to untreated and U0126-treated AA RBC ghosts, for which an increase of 2.1-fold (p=1.5×10$^{-12}$ for untreated AA RBCs vs untreated AA RBCs+ERK2) and 1.7-fold (p=4.6×10$^{-6}$ for U0126-treated AA RBCs vs U0126-treated AA RBCs+ERK2) were measured, respectively.

Figure 7A:
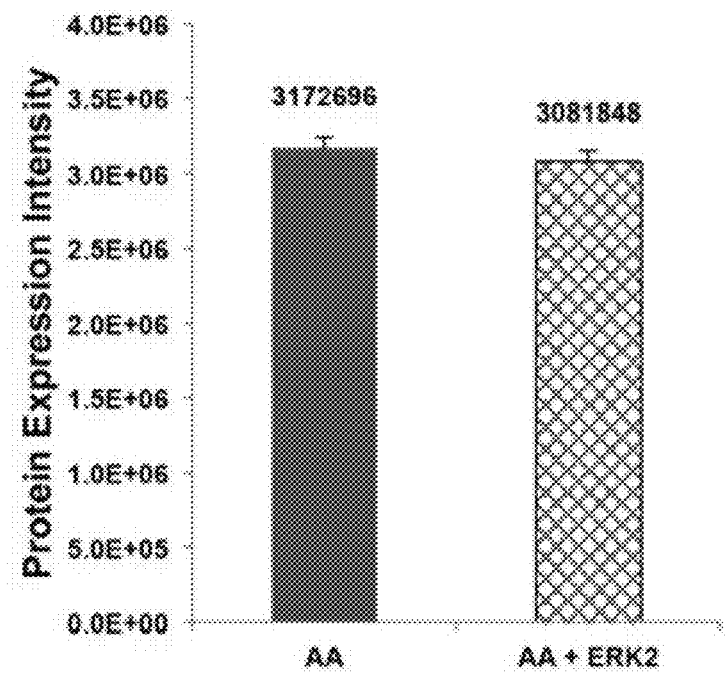
FIG. 7A-7B shows Protein 4.1 levels measured by unbiased label-free quantitative proteomics normalized to levels in (FIG. 7A) AA RBCs or (FIG. 7B) SS RBCs. AA and SS RBC ghosts, and AA and SS RBC ghosts co-incubated with active ERK2. Protein 4.1 levels remain constant in AA RBCs between the two conditions, and also in SS RBCs between the two conditions.
Figure 7B:
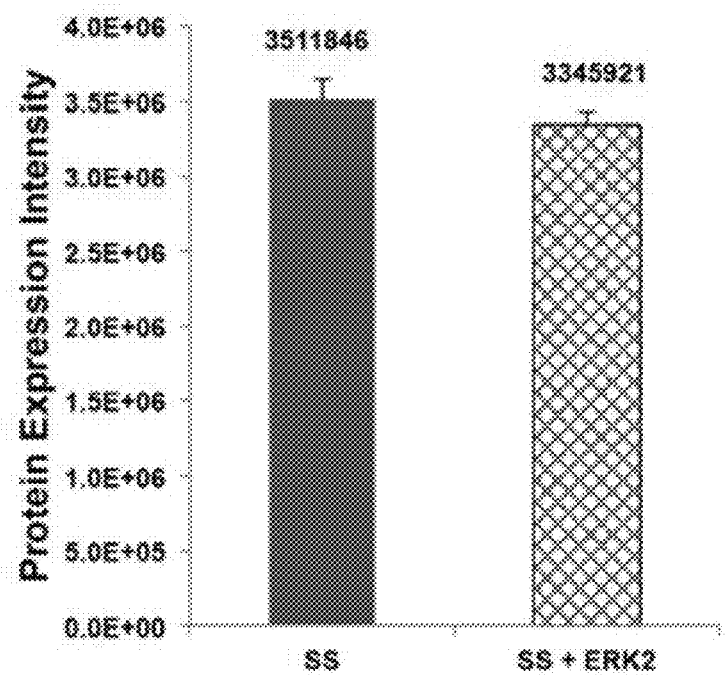

To confirm that the measured changes in phosphorylated peptide levels were not due to a difference in protein level between these treatment conditions, a non-phosphopeptide enriched proteomic analysis of AA RBC ghosts and AA RBC ghosts co-incubated with recombinant ERK2 was performed, and confirmed that protein 4.1 levels were similar between the two conditions (FIG. 7A). This indicates that the observed changes in phosphopeptide abundance results from upstream kinase activity. Similar results were obtained when SS RBC ghosts and SS RBC ghosts co-incubated with recombinant ERK2 were analyzed (FIG. 7B).

Collectively, these data further strengthen our findings that ERK is active in SS RBCs, and suggest that activation of the ERK cascade induces phosphorylation of the cytoskeletal protein 4.1.

Example 8: Recombinant Active ERK2 Phosphorylates the ERK Consensus Motif on Dematin and Adducins α and β

To identify ERK substrates in RBCs, all phosphopeptide sequences within the dataset identified when active recombinant ERK2 was added to RBC ghosts were searched for the known ERK consensus motif, [PV]x[pST]P. Adducin-α and -β, and dematin, contained nine, seven and one unique phosphorylated peptides, respectively, with phosphorylation of residues within the ERK consensus motif. Only the statistically significant phosphopeptides with fold-changes of >1.5 are listed in Table 1. These peptides underwent a significant increase in phosphorylation in AA RBCs when recombinant ERK2 was added to the ghosts, while a decrease in phosphorylation of these peptides was observed in U0126-pretreated SS RBCs (Table 1). This suggests that the cytoskeletal proteins adducins α and β and dematin are substrates for ERK in RBCs.

Table 1.

Motif Specific Phosphorylation by active recombinant ERK2. Fold changes in phosphorylation for peptides containing the ERK consensus motif [PV]x[pST]P were presented. Phopshorylation is up-regulated in normal RBCs (AA) with addition of active ERK2 and down-regulated in SS RBCs (SS) with addition of the MEK inhibitor U0126.

TABLE 1

Motif Specific Phosphorylation by Active Recombinant ERK2

| Protein Description | Modified Peptide Sequence (SEQ ID NO:) | AA + ERK2 vs. AA | P value | SS + U0126 vs. SS | P value |
|---|---|---|---|---|---|
| α-adducin | [pS]PG[pS]PVGEGTGSPPK (SEQ ID NO: 2) | −1.71 | 0.035 | 1.47 | 0.122 |
| α-adducin | EEEAHRPP[pS]PTEAPTEASPEPAPDPAPVAEEAAP SAVEEGAAADPG[pS]DGSPGK (SEQ ID NO: 3) | −1.69 | 0.025 | 1.60 | 0.074 |
| β-adducin | ETAPEEPG[pS]PAK[pS]APA[pS]PVQSPAK (SEQ ID NO: 4) | −2.36 | 4.21E−06 | 1.91 | 3.87E−09 |
| β-adducin | ETAPEEPGSPAK[pS]APA[pS]PVQSPAK (SEQ ID NO: 5) | −1.75 | 0.020 | 1.82 | 0.018 |
| β-adducin | ETAPEEPG[pS]PAK[pS]APASPVQSPAK (SEQ ID NO: 6) | −1.68 | 0.037 | 1.68 | 0.010 |
| Dematin | [pS]TSPPP[pS]PEVWADSR (SEQ ID NO: 7) | −1.76 | 9.46E−09 | 1.48 | 4.98E−04 |

Fold changes in phosphorylation for peptides containing the ERK consensus motif [PV]x[pST]P were presented. Phosphorylation is up-regulated in normal RBCs (AA) with addition of active ERK2 and down-regulated in SS RBCs (SS) with addition of the MEK inhibitor U0126.

Example 9: ERK1/2 is Involved in SS RBC Adhesion to Activated-Endothelial Cells

We have previously shown that both pharmacological agents epinephrine and forskolin upregulate SS RBC adhesion to non-activated endothelial cells via the MEK/ERK signaling pathway (Zennadi et al., Blood 2012). Treatment of SS RBCs with the MEK inhibitor U0126 alone also significantly blocked SS RBC adhesion to non-activated HUVECs (91±4.6% inhibition) when compared to adhesion of sham-treated SS RBCs (p<0.01). These data suggest that increased SS RBC adhesion to non-activated endothelial cells requires activation of RBC adhesion molecules via stimulation of the MEK/ERK pathway.

Figure 8A:
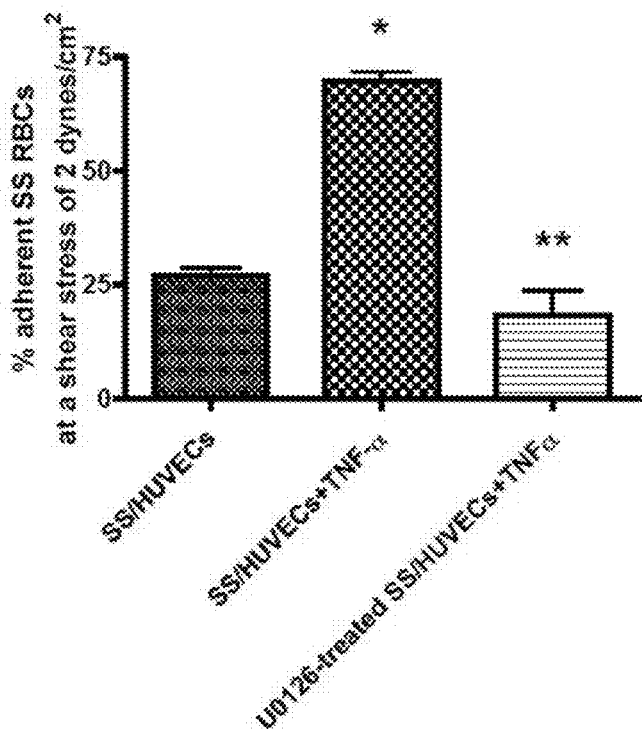
FIG. 8A-8B shows adhesion of SS RBC to activated-endothelial cells involves ERK. Adhesion of SS RBCs to non-activated and TNF-$\alpha$ activated-HUVECs was tested in intermittent flow condition assays. Results are presented as % cells adherent at a shear stress of 2 dynes/cm$^2$ (n=4). Confluent cultures of HUVECs were treated with 10 ng/ml TNF-$\alpha$ for 4 hours, washed, and then tested for their ability to support adhesion of sham-treated SS RBCs or SS RBCs treated with U0126 for 1 hour at 37° C.

Since inflammatory molecules are commonly augmented in sickle cell disease patients, and because Kaul et al. (Blood 2000; 95:368-374) has reported that human SS RBCs adhered to cytokine-stimulated postcapillary endothelium in the absence of plasma, we asked whether ERK in non-stimulated SS RBCs also contributes to SS RBC adhesion to TNF-α-activated HUVECs. Treatment of HUVECs with TNF-α resulted in a significant increase in SS RBC adhesion by 2.6-fold at a shear stress of 2 dynes/cm$^2$ in intermittent flow conditions when compared to adhesion of SS RBCs to non-activated HUVECs, where less than 30% of the cells were able to adhere (p<0.001) (FIG. 8A). However, pretreatment of SS RBCs with 10 μM U0126 significantly reduced adhesion of SS RBCs to TNF-α-activated HUVECs and only 18±5% of the cells adhered compared to adhesion of SS RBCs to non-activated HUVECs (p<0.001). These results suggest that ERK is active in SS RBCs without prior cell-stimulation and is also involved in adhesion to activated-endothelial cells.

Figure 8B:
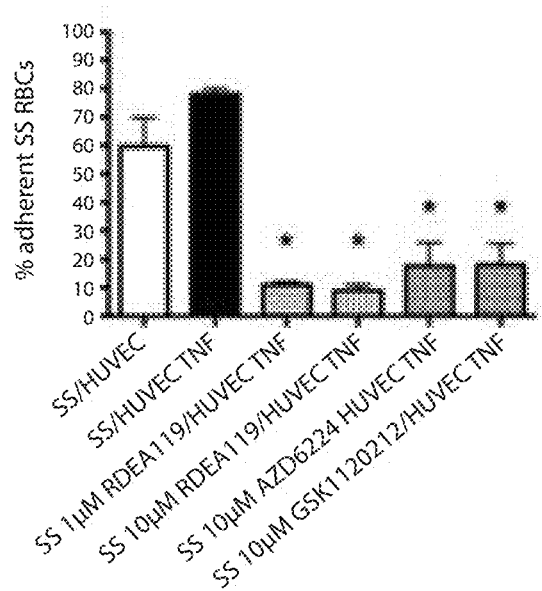

To confirm these initial data, we performed a similar experiment using three other inhibitors of MEK, RDEA119, AZD6244 and GSK1120212. These inhibitors were selected based on their good tolerability in long-term human therapeutic studies. Treatment of SS RBCs with RDEA119, AZD6244 and GSK1120212 (FIG. 8B) significantly abolished SS RBC adhesion to TNF-α-activated endothelial cells to levels below baseline adhesion of SS RBCs to non-activated HUVECs similar to the results shown for U0126 above. These data suggest that ERK signaling is involved in abnormal RBC adhesive interactions with activated-endothelium, and does NOT require activation of the RBCs to mediate RBC adhesion.

Example 10: ERK Contributes to SS RBC Adhesion to Vascular Endothelium and Vaso-Occlusion In Vivo The following experiment was designed to determine whether the MEK inhibitor U0126 can be used as a preventive agent of SS RBC adhesion to activated endothelium and vaso-occlusion. Human SS RBC preparations showed unmeasurable (0 cells/μl) leukocytes or platelets, making it unlikely that human leukocytes and platelets could participate in SS RBC adhesion and vaso-occlusion in our model.

Figure 9A:
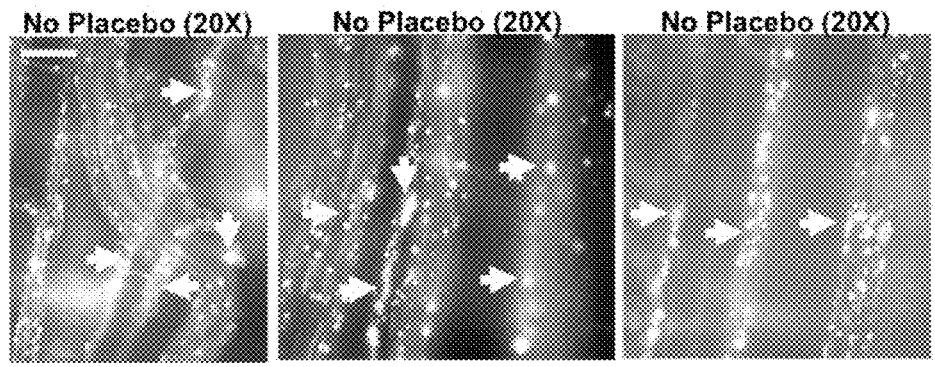
FIG. 9A-9E shows the effect of the MEK inhibitor U0126 on sickle red cell adhesion to the vascular endothelium and vaso-occlusion in nude mice. Microscopic observations of postcapillary venules were conducted through implanted dorsal skin-fold window chambers after infusion of human sickle RBCs into the tail vein of nude mice using 20× magnification. Vessels without adherent cells appear gray, due to the fluorescence of rapidly moving RBCs. TNF-$\alpha$ was injected prior to infusion of the MEK inhibitor U0126 or human sickle RBCs, to induce inflammation, since sickle red cell adhesion to activated endothelium in vitro is markedly up-regulated compared to sickle cell adhesion to non-activated endothelium.
Figure 9B:
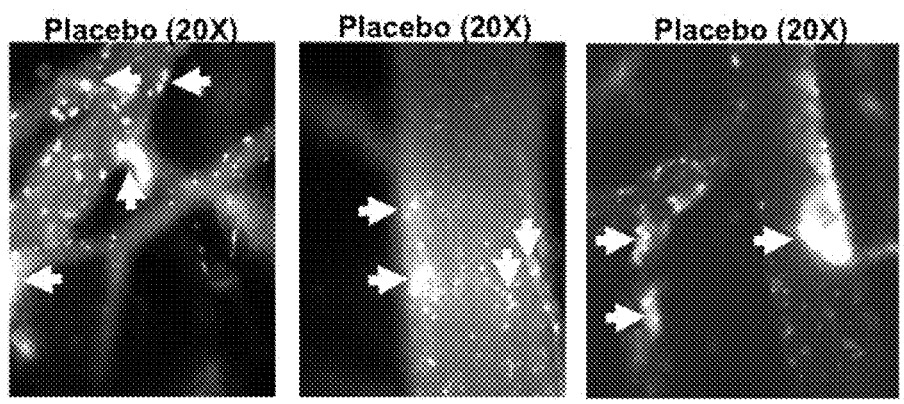
Figure 9C:
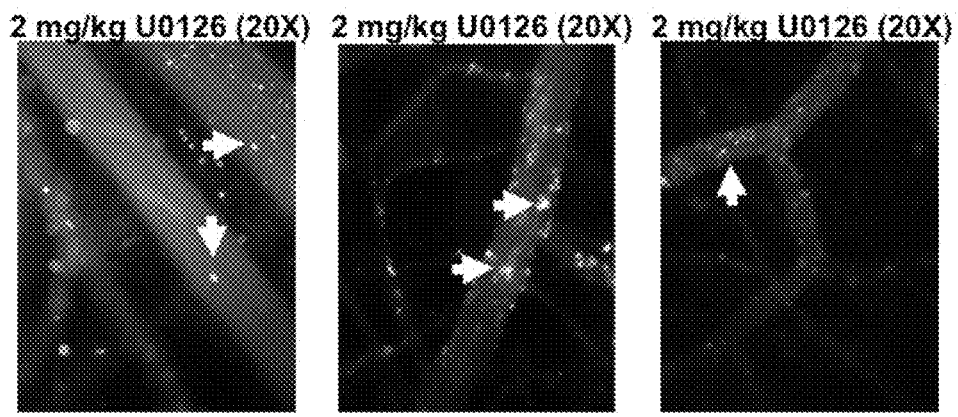

All human SS RBCs were fluorescently labeled, then washed prior to infusion into animals for observation within native intact vessels. Infusion of SS RBCs to mice injected with TNF-α resulted in marked SS RBC adhesion to vessels, predominantly in postcapillary venules, with intermittent occlusion of vessels and permanent blockage of some vessel segments (FIG. 9A). Vaso-occlusion occurred most frequently where vessels curved and at junctions, although it was also observed in straight non-junctional venular segments. SS RBC adhesion was even greater when mice were infused with vehicle (placebo, 0.4% DMSO in normal saline) 30 min prior to RBC infusion (FIG. 9B) than that observed without vehicle infusion (FIG. 9A). SS RBC adhesion to venular endothelium occurred in less than 5 min after RBC infusion, and led to the permanent obstruction of small diameter vessels (FIG. 9B). SS RBC adhesion was also observed in larger vessels. Vaso-occlusion also occurred most frequently where vessels curved and at junctions, although it was also observed in straight non-junctional venular segments. In contrast, SS RBCs showed very little adhesion to vascular endothelium and adhered only occasionally to small postcapillary venules when animals were infused with 2 mg/kg U0126 in 0.4% DMSO 30 min prior to RBC infusion with no apparent vaso-occlusion (FIG. 9C).

Figure 9D:
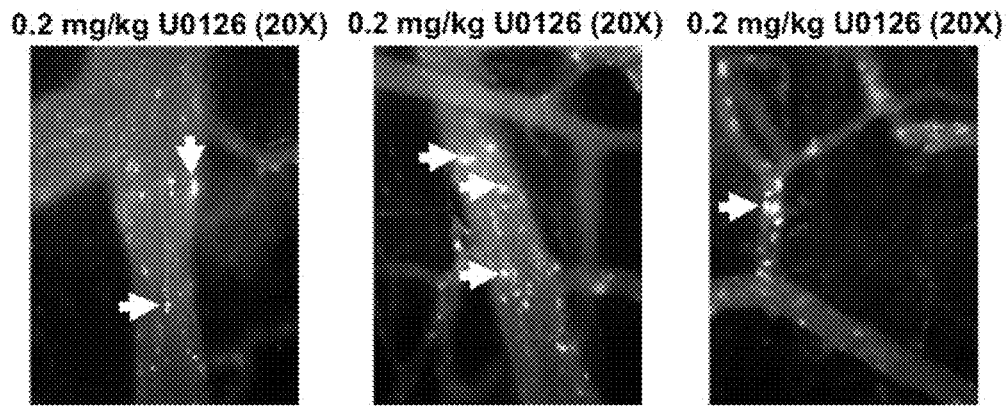
Figure 9E:
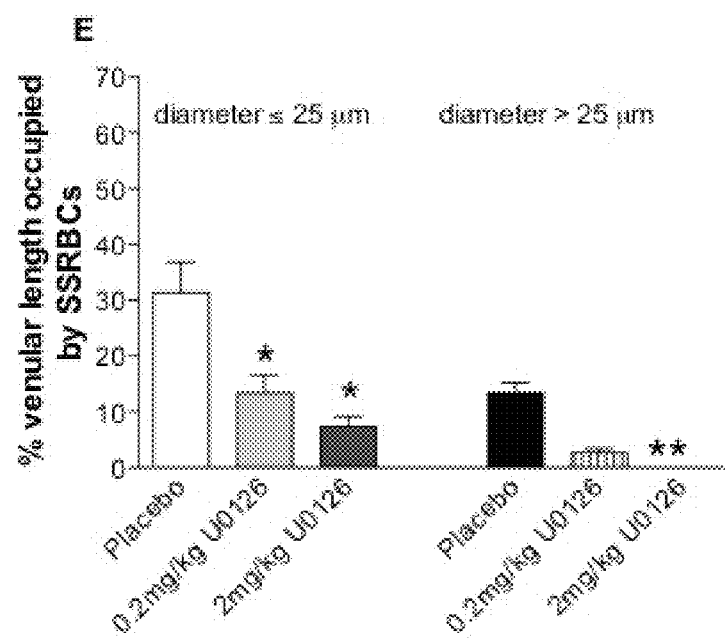

Similarly, when animals were infused with 0.2 mg/kg U0126 in 0.04% DMSO in saline 30 minutes prior to RBC infusion no apparent vaso-occulsion was observed (FIG. 9D). The effect of U0126 on % venular length occupied by SS RBCs was quantified. The MEK inhibitor U0126 at 0.2 and 2 mg/kg induced a significant decrease in percentage venular length occupied by SS RBCs for vessels 25 µm in diameter (p<0.001) (FIG. 9E). However, when vessel diameter was >25 µm, U0126 at 0.2 mg/kg did not significantly reduce the percentage venular length occupied by SSRBCs. These data strongly suggest that ERK is implicated in SS RBC adhesion to poscapillary venules promoting vaso-occlusion, and that the MEK inhibitor U0126 is able to down-regulate adhesion of subsequently infused SS RBCs and prevent precipitation of occlusion of enflamed vessels when provided in the circulation. These data also suggest that MEK inhibitors may be able to reduce inflammation.

Figure 10A:
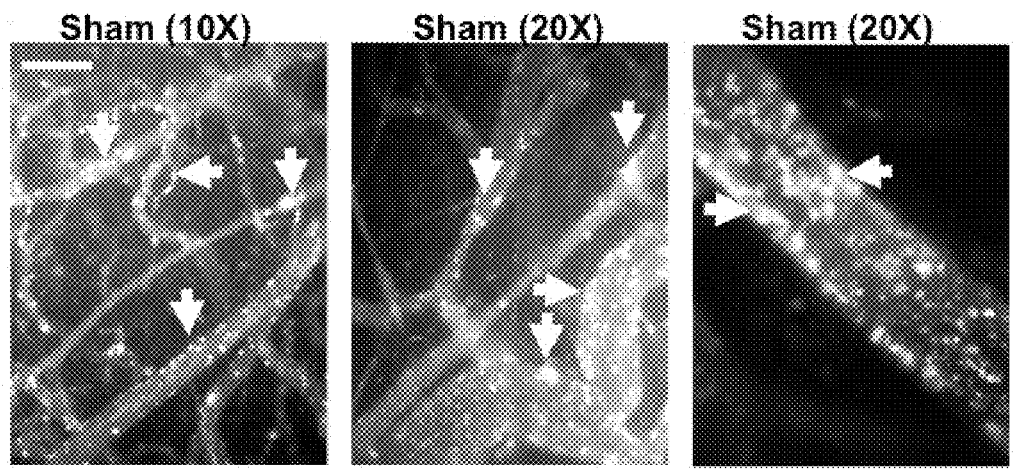
FIG. 10A-10D sows that MEK inhibitors prevent SSRBC adhesion in inflamed vessels and vaso-occlusion in vivo. Human sickle RBCs were sham-treated or treated with the MEK inhibitor RDEA119 or U0126 ex vivo, washed extensively, and then infused into the tail vein of nude mice pretreated with TNF-α. Microscopic observations of venules were conducted through a dorsal skin-fold window chamber using 10× and 20× magnifications, after infusion of fluorescently labeled human SS RBCs. Vessels without adherent cells appear gray, due to rapidly moving fluorescent RBCs.
Figure 10B:
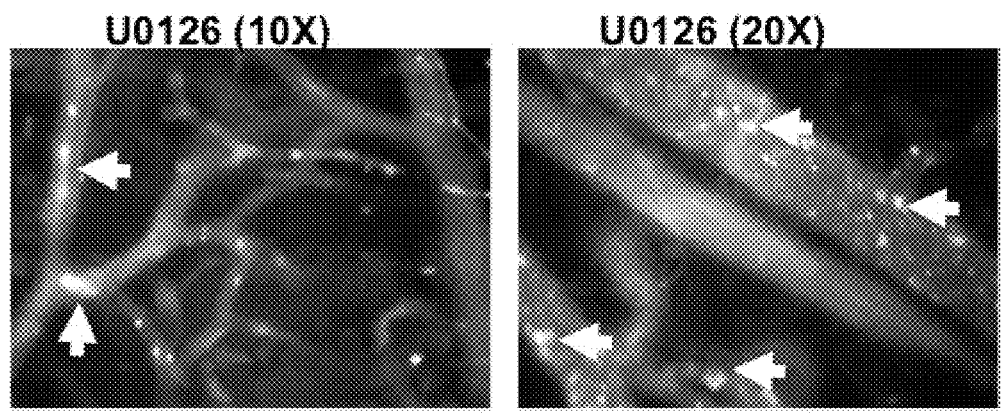
Figure 10C:
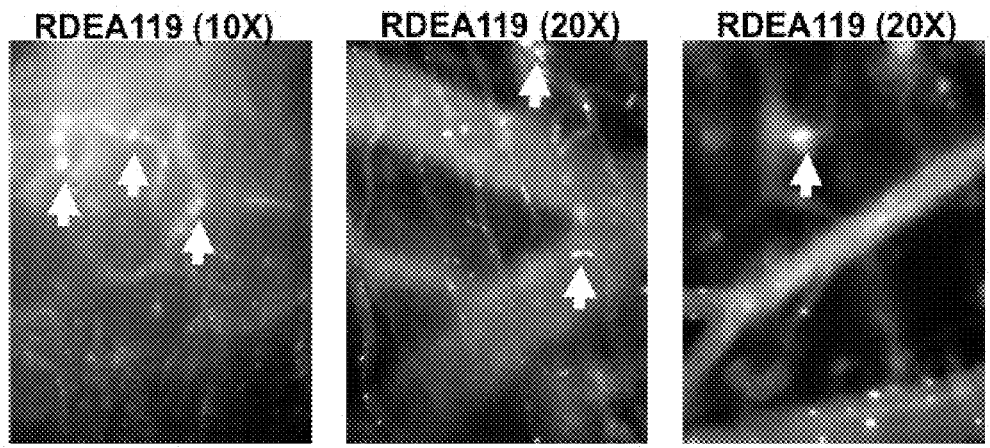
Figure 10D:
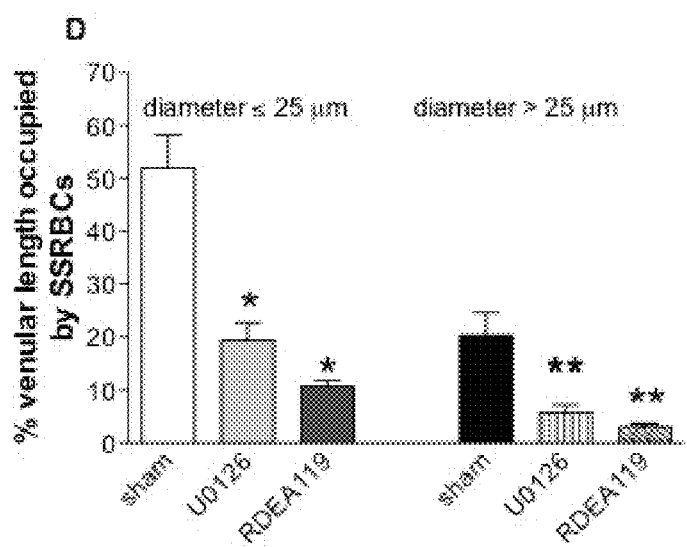

To further these studies, we tested whether the MEK inhibitor prevents SS RBC-induced vasoocclusion via at least its effect on SS RBCs. SS RBCs were treated with the MEK inhibitors U0126 and RDEA119 ex vivo prior to administration to the mice. Intravital microscopy studies showed that infusion of sham-treated human SS RBCs to nude mice treated with TNF-α (n=5), showed marked adhesion in inflammed venules and induced occlusion of small diameter (9-25 µm) vessels (n=5). SSRBC adhesion was also observed in much larger vessels (up to 100 µm in diameter), indicating that human SSRBC-induced vasoocclusion was not a result of trapping of human SSRBCs in vessels with diameters 8 µm, since the size of human RBC is 8 µm in diameter (FIG. 10A). However, inhibition of MEK/ERK in human SSRBCs with U0126 ex-vivo prior to RBC infusion to animals treated with TNF-α (n=5), dramatically decreased human SSRBC adhesion and prevented vessel obstruction (FIG. 10B). Similarly, treatment of human SS RBCs with RDEA119 (n=5) also dramatically decreased human SS RBC adhesion and prevented vessel obstruction (FIG. 10C). The Effect of U0126 and RDEA119 on % venular length occupied by SS RBCs, was quantified. The percentage of venular length occupied by both U0126-treated SS RBCs and RDEA119-treated SS RBCs significantly decreased for vessels 25 µm in diameter (p<0.001 compared to sham) and vessels with a diameter>25 µm (p<0.05 compared to sham) (FIG. 10D). These data suggest that MEK inhibition with U0126 and RDEA119 improved SS RBC circulatory behavior due to amelioration of SS RBC adhesive function. Thus, our data suggest that ERK and its mechanism of action could represent a novel target for the treatment of SCD pathophysiology.

Figure 11:
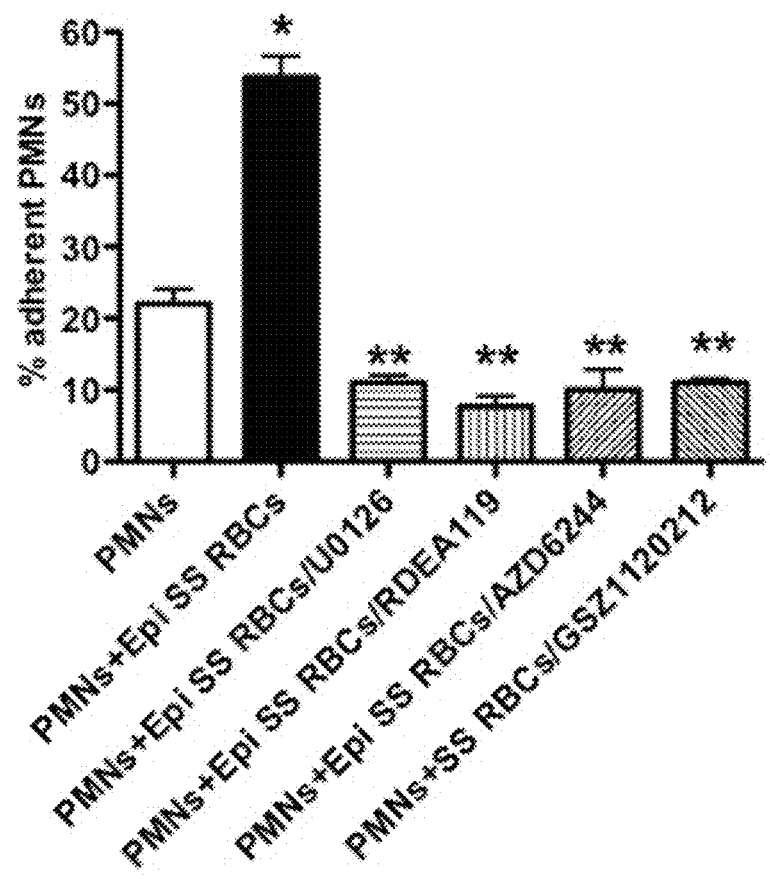
FIG. 11 shows MEK inhibitors inhibit epinephrine-stimulated SS RBC-mediating neutrophil adhesion to endothelial cells. SS RBCs were treated with epinephrine (Epi), or pre-incubated with U0126, RDEA119, AZD6244 or GSK1120212 followed by treatment with Epi, and then washed. Native neutrophils (PMNs) from healthy donors were then co-incubated with treated-SS RBCs, and assayed for their ability to adhere to HUVECs. Adhesion of PMNs was much higher when cells were co-incubated with Epi-treated SS RBCs compared to adhesion of naïve PMNs not co-incubated with SS RBCs. However, all MEK inhibitors tested were equally able to markedly reduce the effect of epinephrine-stimulated SS RBCs on PMN adhesion to HUVECs when compared to adhesion of epinephrine-activated SS RBC-mediated PMN adhesion. *:$p<0.0001$ compared to native PMNs; and **:$p<0.0001$ compared to PMN adhesion mediated by epinephrine-treated SS RBCs. Error bars show SEM of 4 different experiments.

Example 11: Incubation of Polymorphonuclear Cells with SSRBCs Results in Activation of the Polymorphonuclear Cells To further analyze the effect of ERK activation on SSRBCs, we treated SSRBCs with 20 nM epinephrine alone for 1 min or after pre-incubation with 10 mM U0126, RDEA119, AZD6244 or GSK1120212 for 1 hour, followed by treatment with 20 nM epinephrine for 1 min. The cells were then washed prior to admixture with fluorescently-labeled native polymorphonuclear cells (PMNs) obtained from healthy donors at a RBC:PMN ratio of 10:1. After co-incubation for 30 minutes at 37° C., cells mixtures were assayed for their ability to adhere to non-activated HUVECs. Since the only cell population visualized was red-fluorescence labeled normal PNMs, the quantitation of adherent PMNs did not include non-labeled SS RBCs or any remaining non-labeled leukocytes from SCD patients. Our data show that co-incubation of epinephrine-activated SS RBCs with naive PMNs, resulted in significant activation of PMN adhesion to non-activated endothelial cells compared to adhesion of native normal PMNs not co-incubated with SS RBCs (FIG. 11). However, blocking ERK activity in activated-SSRBCs with MEK inhibitors U0126, RDEA119, AZD6244 and GSK1120212 significantly decreased the ability of activated-SS RBCs to promote neutrophil adhesion (FIG. 11). These data suggest that ERK signaling is involved in activation of SS RBC adhesion receptors involved in interactions with the endothelium and leukocytes. Downregulation of RBC adhesion receptor activity by targeting ERK may not only decrease SS RBC adhesion to the endothelium but also reduce RBC-stimulated leukocyte activation.

Example 12: Phosphoproteomic Profiling of RBC Membranes

However, sickle cell adhesion and vaso-occlusion alone do not account for the pathophysiology of SCD. Subsequent changes in red cell membrane structure and function and disordered cell volume control may also play an important role. Therefore, we investigated the ERK1/2 mediated RBC protein phosphorylation in SS RBC plasma membrane as compared to AA RBC plasma membrane.

Collection, Preparation and Treatment of RBCs.

Human SCD patients homozygous for hemoglobin S were not transfused for at least three months, had not experienced vaso-occlusion for three weeks, and were not on hydroxyurea. Blood samples from SCD patients and healthy donors collected into citrate tubes, were used within less than 24 h of collection. Packed RBCs were separated as previously described in detail.[66] Packed RBCs were analyzed for leukocyte and platelet contamination using an Automated Hematology Analyzer K-1000 (Sysmex, Japan). For proteomics studies, aliquots of packed RBCs were treated at 37° C. with 10 µM MEK1/2 inhibitor U0126 (Calbiochem, La Jolla, Calif.) for 1 hour. Sham-treated RBCs were incubated with the same buffer and vehicle, but without the active agent. Normal RBCs were used as controls.

MAP Kinase Activity Assay.

Treated packed normal and SS RBCs were lysed at 4° C. with lysis buffer (10 mM EDTA, 20 mM Tris, 110 mM NaCl, pH 7.5) containing 2 mM PMSF, 1% Triton X-100, phosphatase inhibitor cocktail (Sigma) and protease inhibitor cocktail (Sigma-Aldrich, St. Louis, Mo.). RBC membrane ghosts were then incubated with or without recombinant active human ERK2 (sigma) at 8.2 µg/ml with a specific activity of 700 nmole/min/mg, in the presence of inhibitors of PKA, PKC, $Ca^{2+}$/calmodulin-dependent kinase and $p34^{cdc2}$ kinase to prevent nonspecific protein phosphorylation by these enzymes,[67] and with ATP as a phosphate donor with equal membrane ghost protein amounts per assay condition. For the negative control, an equal volume of water was substituted for ATP. The reaction mixture was incubated for 20 min at 30° C. To stop the enzymatic reaction samples were placed on ice.

RBC Membrane Ghost Preparation and Phosphopeptide Enrichment.

Non-radiolabeled RBC membrane ghosts isolated from packed RBCs sham-treated or treated with U0126 and incubated with or without recombinant ERK2, were spun at 14,000 rpm for 15 min at 4° C. to pellet membranes. Membrane pellets were washed with 1 mL 50 mM ammonium bicarbonate (pH 8.0) with vortexing and were then spun at 14,000 rpm for 30 min at 4° C. The supernatant was then removed and 500 μL of 50 mM ammonium bicarbonate with μL 0.2% acid-labile surfactant (ALS-1) in 50 mM ammonium bicarbonate (pH 8.0) was added. Samples were subjected to probe sonication three-times for 5 sec with cooling on ice between and insoluble material was cleared by centrifugation at 14,000 rpm for 30 min at 4° C. Samples were normalized to approximately 2 μg/μl following a micro-Bradford assay (Pierce Biotechnology, Inc), and were reduced with a final concentration of 10 mM dithiothreitol at 80° C. for 20 min. Samples were then alkylated with a final concentration of 20 mM iodoacetamide at room temperature for 45 min and trypsin was added to a final ratio of 1-to-50 (w/w) enzyme-to-protein and allowed to digest at 37° C. for 18 hr. To remove ALS-1, samples were acidified to pH 2.0 with neat TFA, incubated at 60° C. for 2 hrs and spun at 14,000 rpm to remove hydrolyzed ALS-1. Samples were either subjected to LC-MS analysis following a 10× dilution into mobile phase A or subjected to a $TiO_2$ based phosphopeptide enriched protocol.

To enrich for phosphorylated peptides prior to LC-MS analysis, 1,125 μg of total digested protein from RBC ghosts were brought to near dryness using vacuum centrifugation and then resuspended in 200 μL of 80% acetonitrile, 1% TFA, 50 mg/ml MassPrep Enhancer (pH 2.5) (Waters Corp., Milford, Mass.). Samples were loaded onto an in-house packed $TiO_2$ spin column (Protea Biosciences) with a 562 μg binding capacity pre-equilibrated with 80% acetonitrile, 1% TFA (pH 2.5). For all loading, washing, and elution steps, the centrifuge was set to achieve a flow rate of no faster than 100 μL/min. Samples were washed twice with 200 μL 80% acetonitrile, 1% TFA, 50 mg/ml MassPrep Enhancer (pH 2.5) followed by two washes with 200 μL 80% acetonitrile, 1% TFA (pH 2.5). Retained peptides were eluted twice with 100 μL 20% acetonitrile, 5% aqueous ammonia (pH 10.0), acidified to pH 3 with neat formic acid and then brought to dryness using vacuum centrifugation. Prior to LC-MS analysis, each sample was resuspended in 20 μL 2% acetonitrile, 0.1% TFA, 25 mM citric acid (pH 2.5).

Label-Free Quantitative Proteomic Analysis of RBC Membrane Ghosts.

Chromatographic separation of phosphopeptide enriched or non-enriched samples was performed on a Waters NanoAquity UPLC equipped with a 1.7 μm BEH130 $C_{18}$ 75 μm I.D.×250 mm reversed-phase column. The mobile phase consisted of (A) 0.1% formic acid in water and (B) 0.1% formic acid in acetonitrile. Five pi injections of each sample were trapped for 5 min on a 5 μm Symmetry $C_{18}$ 180 μm I.D.×20 mm column at 20 μl/min in 99.9% A. The analytical column was then switched in-line and the mobile phase was held for 5 min at 5% B before applying a linear elution gradient of 5% B to 40% B over 90 min at 300 nL/min. The analytical column was connected to fused silica PicoTip emitter (New Objective, Cambridge, Mass.) with a 10 μm tip orifice and coupled to the mass spectrometer through an electrospray interface.

MS data from each phosphopeptide enriched sample was acquired on a Thermo LTQ-Orbitrap XL mass spectrometer operating in positive-ion mode with an electrospray voltage of 2.0 kV with real-time lockmass correction on ambient polycyclodimethylsiloxane (m/z 445.120025) enabled. The instrument was set to acquire a precursor MS scan from m/z 400-2000 with r=60,000 at m/z 400 and a target AGC setting of 1e6 ions. Each sample was analyzed four-times, one of which acquired MS/MS spectra in the ion-trap for the top 10 most abundant precursor ions and was used for additional qualitative identifications only. All other quantitative analysis acquired MS/MS spectra in the ion-trap for the top 5 most abundant precursor ions above a threshold of 500 counts. Maximum fill times were set to 1000 ms for full MS scans acquired in the OT and 250 ms for MS/MS acquired in the linear ion trap, with a CID energy setting of 35% and a dynamic exclusion of 60 s for previously fragmented precursor ions. Multistage activation (MSA) for neutral losses of 98.0, 49.0, and 32.33 Da was enabled to enhance fragmentation of phosphorylated peptides.

Non-phosphopeptide enriched data were acquired on a Waters Synapt HDMS operating in positive-ion mode with an electrospray voltage of 3.0 kV. Each sample was analyzed three times in a data-independent ($MS^E$) mode of acquisition with 0.9 sec cycle times alternating between low collision energy (6 V) and high collision energy ramp (15 to 40 V). One additional data-dependent (DDA) analysis using a 0.9 sec MS scan followed by MS/MS acquisition on the top 3 ions with charge greater than 1 was acquired to increase the number of qualitative identifications. MS/MS scans for each ion used an isolation window of approximately 3 Da, a maximum of 4 seconds per precursor, and dynamic exclusion for 120 seconds within 1.2 Da.

Database Searching and Label-Free Quantitation.

Label-free quantitation and integration of qualitative peptide identifications was performed using Rosetta Elucidator (v 3.3, Rosetta Inpharmatics, Seattle, Wash.). All raw LC-MS/MS data within either the phosphopeptide enriched or non-enriched experiments were imported and subjected to chromatographic retention time alignment using the PeakTeller® algorithm with a minimum peak time width set to 6 s, alignment search distance set to 4 min and the refine alignment option enabled. Quantitation of all measurable signals in the precursor MS spectra (excluding LC-MS analysis intended only for additional qualitative identifications), was performed by Elucidator by calculating either peak volume (area under curve) for Synapt HDMS data files or peak height for LTQ-Orbitrap data files.

Qualitative peptide identifications from all phosphopeptide enriched samples and DDA analysis of non-phosphopeptide enriched samples, were made by generating DTA files for all precursor ions, which had associated MS/MS spectra. DTA files were submitted to Mascot (Matrix Science, Boston, Mass.) and searched against a *Homo sapien* protein database downloaded from SwissProt concatenated with the sequence-reversed version of each entry. $MS^E$ data were independently processed within ProteinLynx Global Server 2.4 (Waters Corp) and searchable files were then submitted to the IdentityE search engine (Waters Corp). Search tolerances of 10 ppm precursor and 0.8 Da product ions were initially applied to LTQ-Orbitrap data and then manually refined to 4 ppm around the apex of the ppm mass error distribution from the most confident forward entries. Tolerances of 20 ppm precursor and 0.04 Da product ions were applied for Synapt HDMS data files with lock-mass correction on m/z 785.8426 (doubly-charged Glu-1-Fibrinopeptide ion) enabled. All data were searched using trypsin specificity with up to two missed cleavages with a static modification of Carbamidomethylation (+57.0214 Da on C) and dynamic modifications of oxidation (+15.9949 Da on M). Dynamic search modifications of phosphorylation (+79.9663 Da on STY) and of deamidation (+1.008 Da on NQ) were employed for phosphopeptide enriched sample and non-phosphopeptide enriched samples, respectively. False-discovery rate were determined by adjusting the Mascot peptide ion score threshold to allow a 1% occurrence of peptide spectral matches from reverse protein entries for phosphopeptide enriched experiments, or by using PeptideProphet algorithim thresholds corresponded to a 2% peptide false discovery rate for non-phosphopeptide enriched experiments.

Database search results and spectra have been uploaded in the form of Scaffold 3 files (.sf3, Proteome Software, Inc) to the Tranche database (https://proteomecommons.org/tranche/) under the group "RBC Ghost Membrane Phosphoproteome" with the following links (if a password is requested, it is rbcphos).

Glycophorin A phosphorylation and immunoprecipitation. Packed RBCs $^{32}$P-labeled as previously described,[68] were sham-treated, or incubated with serine/threonine phosphatase inhibitor (SPI) cocktail (Sigma) for 30 min, SPI cocktail followed by 1 min treatment with 20 nM epinephrine, or pre-incubated with 10 µM U0126 for 1 h followed by SPI cocktail, then treated with 20 nM epinephrine for 1 min. Cells were then washed 4 times. Glycophorin A immunoprecipitation using anti-glycophorin A monoclonal antibody (mAb) (Abcam, Cambridge, Mass.) and the negative control immunoglobulin P3, and total and phospho-glycophorin A detection were performed as previously described in detail.[66] To confirm that the immunoprecipitates were specific for glycophorin A, anti-glycophorin A mAb and the negative control P3 were used to immunoprecipitate glycophorin A from non-radiolabeled treated SS RBCs. Blots were immunostained with anti-glycophorin A mAb.

Statistical Analysis.

Data were compared using parametric analyses (GraphPad Prism 5 Software, San Diego, Calif.), including repeated and non-repeated measures of analysis of variance (ANOVA). One-way and two-way ANOVA analyses were followed by Bonferroni corrections for multiple comparisons (multiplying the p value by the number of comparisons). A p value<0.05 was considered significant.

Label-Free Quantitative Phosphoproteomic Profiling of RBC Membranes.

Quantitation of global (non-targeted) phosphorylation events directly from human RBCs in disease-affected patients has been very limited in the literature. The most common analytical strategies have employed coupling two-dimensional gel electrophoresis of solubilized RBC proteins with either global $^{32}$P labeling or anti-phosphotyrosine detection antibodies, followed by LC-MS/MS identification of phosphoproteins from differentially expressed protein spots. In addition to the limited number of unique treatment groups, which could be directly compared within a single study, these previous approaches do not afford residue-specific quantitation of phosphorylation events as initial detection in changes in phosphorylation status measured at the protein level. This is particularly problematic for proteins containing multiple sites of phosphorylation, as each could be independently modulated by different kinases or phosphatases as a function of various stimuli. In addition, different phosphorylation sites could have different effect on protein function. Although strategies such as iTRAQ, which are commonly used for phosphoproteomic quantitation from non-cell culture based systems, address some of these limitations, the reagents are still limited to a maximum of eight unique treatment groups (or unique samples), and add significant cost when performing the labeling at the quantities of protein required for phosphoproteomic analysis.

Figure 12A:
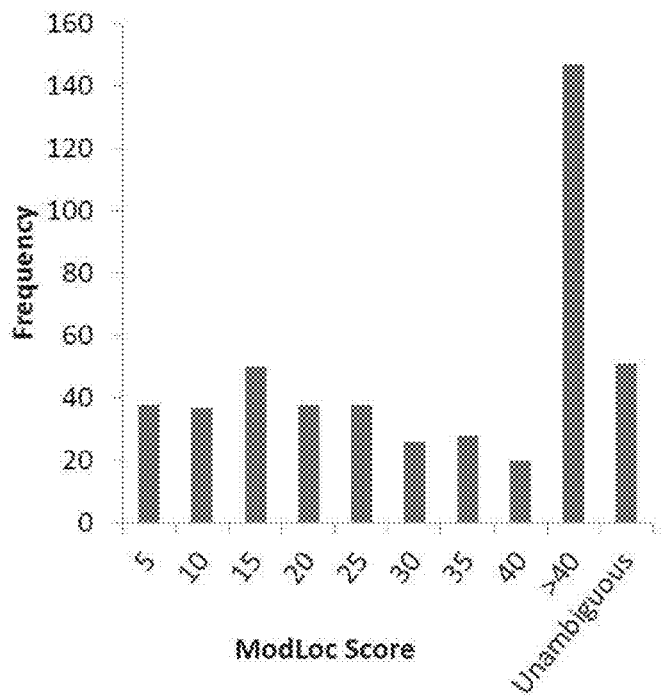
FIG. 12A shows AScore site localization scoring distributions across all 375 unique phosphorylated peptides from RBC ghost preparations.
Figure 12B:
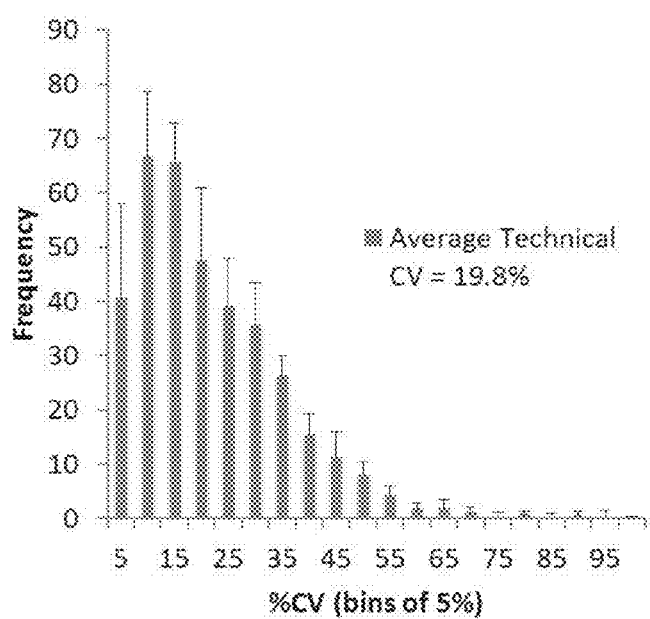
FIG. 12B shows the Coefficient of variation (% CV) distribution of measured phosphopeptide peak heights from triplicate LC-MS analysis of a treatment group following accurate-mass and retention time alignment. Error bars indicate standard deviation within each % CV bin across all eight treatment groups.
Figure 13A:
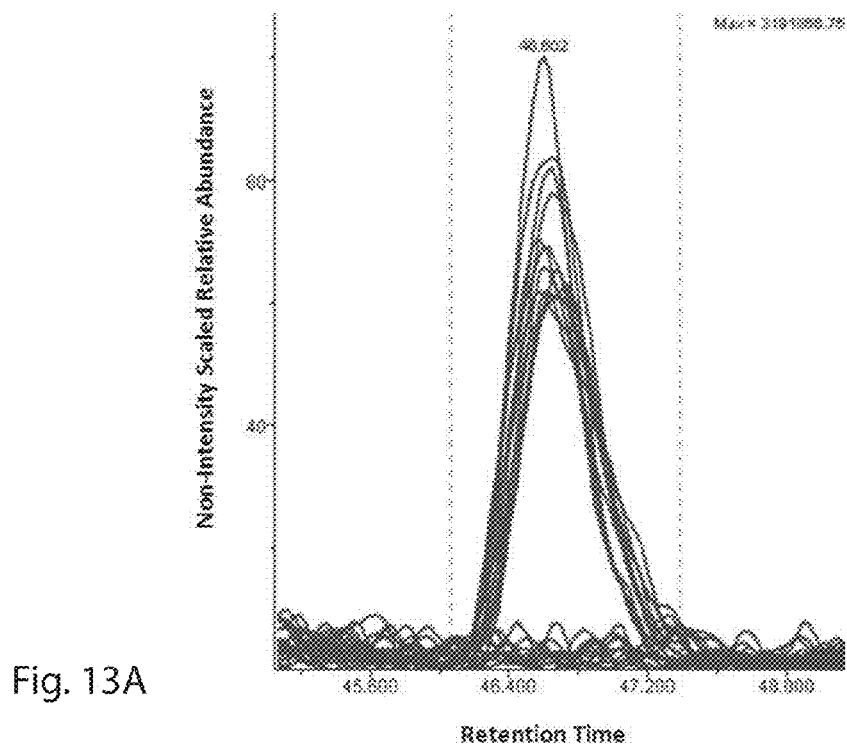
FIG. 13A-13B shows selected ion chromatogram (FIG. 13A) and AUC quantitation (FIG. 13B) of 173-VADPDH-DHTGFLTE[pY]VATR-191 ($[M+3H]^{3+}$ 741.999 m/z) (SEQ ID NO:1) the active form of Mitogen-Activated Protein Kinase-1 (GN=MAPK1, ERK2), across 24 LC-MS injections. This peptide was qualitatively identified with a maximum mascot ion score of 63.3 and a site localization Ascore of 41+/−12.
Figure 13B:
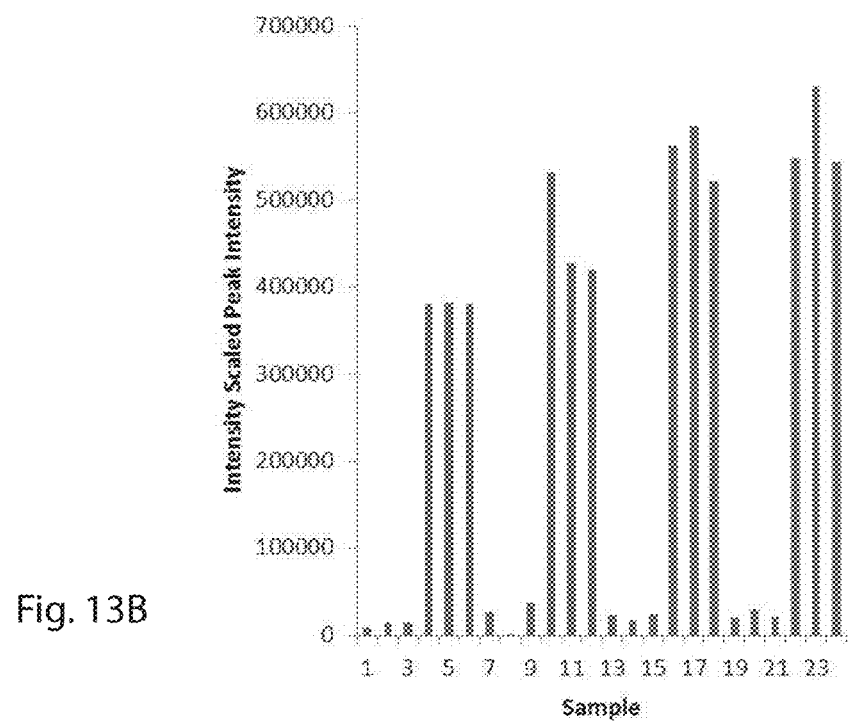

Across all our samples tested, 375 unique phosphopeptides (527 total phosphorylated residues) corresponding to 155 phosphoproteins were identified at a peptide spectral match false discovery rate of 1.0%. As localization of specific phosphorylated residues is critical for defining kinase specific events, all phosphopeptides were subjected to ModLoc, a probability-based localization tool implemented within Rosetta Elucidator based on the AScore algorithm (FIG. 12A). (Beausoleil et al., A probability-based approach for high-throughput protein phosphorylation analysis and site localization. *Nature biotechnology.* October 2006; 24(10):1285-1292). Approximately 74% (348) of phosphorylated residues had ModLoc scores above 15 (>90% probability of correct localization) and 66% (310) had ModLoc scores above 20 (>99% probability of correct localization). To assess the quantitative robustness of the label-free approach, the average technical coefficient of variation (% CV) of retention-time aligned phosphorylated peptide intensities within a treatment group were calculated. The average % CV across all 375 phosphopeptides was 19.8%, with 80% of the signals having a % CVs less than 27.1% (FIG. 12B). The intensity of the phosphorylated peptide V173-[pY187]-R191 within the activated site of ERK1/2 was used to assess inter-treatment group variation, including variation from TiO$_2$ phosphopeptide enrichment, as activated ERK2 was spiked in equal amounts to four of the eight samples. The average % CV of this phosphopeptide within any treatment group was 7.0% and across all ERK2 spiked samples was 18.1% (FIGS. 13A and 13B).

Figure 14A:
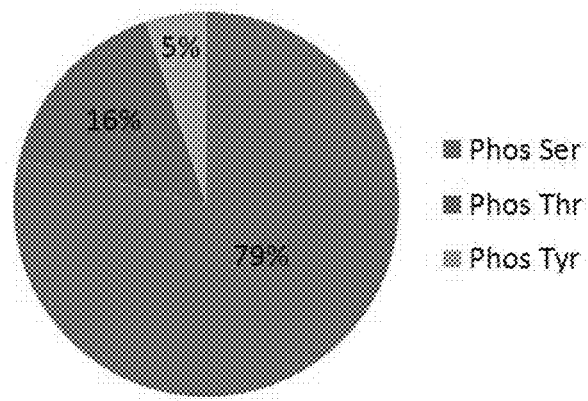
FIG. 14A-14B is a set of graphs is showing the distribution of types of phosphorylated residues and phosphorylated residues per peptide (FIG. 14A) and the biological functions of the phosphorylated proteins (FIG. 14B).
Figure 14A:
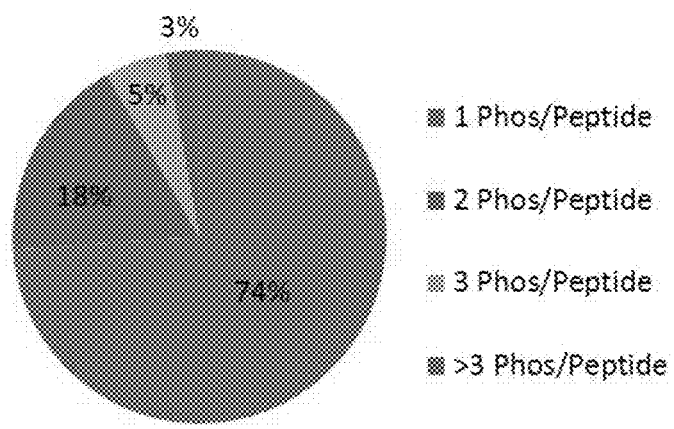
Figure 14B:
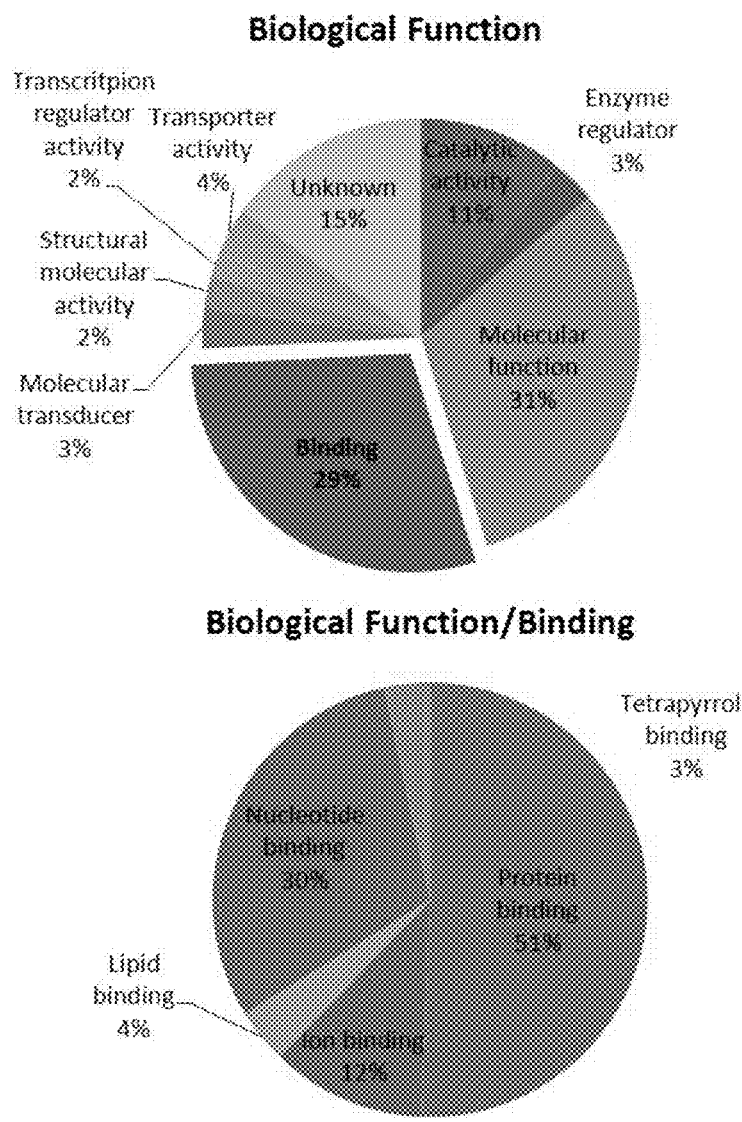

Consistent with a majority of TiO$_2$-enrichment based global mammalian phosphoproteomic studies, 78% (415) of the identified phosphorylated residues were localized to serines, 16% (85) to threonines, and 5% (27) to tyrosines, with an average of 1.4 phosphorylated residues per peptide (FIG. 14A). Gene ontology classification of the biological function of the 155 identified phosphoproteins indicated nearly a third of the phosphoproteins were involved in binding as their primary biological function. Sub-classification of the binding category revealed over 80% of those phosphoproteins were involved in either protein binding (51%) or nucleotide binding (30%) (FIG. 14B). Phosphoproteins involved in ion binding consisted 12% of the total phosphoproteins. These data were expected since our RBC samples were membrane fractions. Consistent with other RBC membrane phosphorylation studies, the phosphoproteins of SS RBC membrane ghosts with the highest number of uniquely phosphorylated peptides (>10), were ankyrin-1 of the ankyrin complex (n=33), spectrin β chain of the cytoskeleton network (n=15), and proteins of the junctional complex involved in binding integral membrane proteins to cytoskeletal proteins, including α- and β-adducins (n=22 and n=18, respectively), dematin (n=18) and protein 4.1 (n=17) (Table 2). However, with the exception of spectrin β chain, addusins α and β, and dematin, inhibition of MEK1/2 and its downstream singling in SS RBCs with the MEK inhibitor U0126, and co-incubation of U0126-treated SS RBC membrane ghosts with active recombinant ERK2, failed to induce significant changes (decrease and increase, respectively) in the abundance of ankyrin-1 and protein 4.1 phosphopeptides (Table 2).

TABLE 2

Unique phosphorylated SS RBC membrane proteomes.

| Protein Description | Gene Name | Unique Phosphorylated Peptides | Unique Phosphorylated Residues |
|---|---|---|---|
| Ankyrin-1 | ANK1 | 33 | 26 |
| Glyophorin A | GYPA | 23 | 8 |
| Alpha-adducin | ADD1 | 22 | 22 |
| Beta-adducin | ADD2 | 18 | |
| Protein 4.1 | EPB41 | 17 | 10 |

TABLE 2-continued

Unique phosphorylated SS RBC membrane proteomes.

| Protein Description | Gene Name | Unique Phosphorylated Peptides | Unique Phosphorylated Residues |
|---|---|---|---|
| Dematin | EPB49 | 16 | |
| Spectrin beta chain | SPTB1 | 15 | 15 |
| Band 3 anion transport protein | SLC4A1 | 14 | 10 |
| Uncharacterized protein LOC388588 | YA047 | 7 | |
| GTPase-activating protein and VPS9 domain-contaning protein 1 | GAPVD1 | 5 | |
| Lipin-2 | LPIN2 | 5 | |
| Serine/threonin-protein kinase WNK1 | WNK1 | 5 | |
| Spectrin alpha chain | SPTA1 | 4 | |
| Erythroid membrane-associated protein | ERMAP | 4 | |
| Heat shock protein HSP90-alpha | HSP90A | 4 | |
| Phosphatidylinositol 4-kinase | PI4K2A | 4 | |
| TSC22 domain family protein 4 | TSC22D4 | 4 | |

Unique phosphopeptides and their unique phosphorylated residues in SS RBC membrane fractions are presented.

Previous studies have shown that protein 4.1 is extensively phosphorylated in sickle red cells. George, et al. Altered phosphorylation of cytoskeleton proteins in sickle red blood cells: the role of protein kinase C, Rac GTPases, and reactive oxygen species. *Blood Cells Mol Dis.* Jun. 15 2010; 45(1):41-45. Protein 4.1 phosphorylation, induced by cAMP-dependent kinase at Ser-331, results in multiple changes in RBC membrane, including significant reduction both in the ability of protein 4.1 to promote spectrin binding to F-actin and in spectrin-protein 4.1 binding. Ling et al., Modulation of red cell band 4.1 function by cAMP-dependent kinase and protein kinase C phosphorylation. *J Biol Chem. Feb.* 15 1988; 263(5):2209-2216. These changes weaken the binding sites for glycophorin C, XK and Duffy of the 30 kDa domain and the stability of the ternary junction complex, with possible effects on membrane mechanical stability and reduction in shear resistance to the membrane. However, while ERK1/2 signaling in SS RBCs is cAMP- and PKA-dependent, increased phosphorylation of protein 4.1 and ankyrin-1 in SS RBCs seems to not involve ERK1/2 signaling. Our data also indicate that in addition to these commonly reported phosphoproteins, several other phosphoproteins with >5 unique phosphorylated peptides were also observed (Table 2). These phosphoproteins also affect RBC shape, flexibility, anion transport and protein trafficking, and adhesion, all of which contribute to the pathophysiology of SCD.

ERK1/2 Induces Atypical Phosphorylation of SS RBC Membrane Proteins.

Figure 15A:
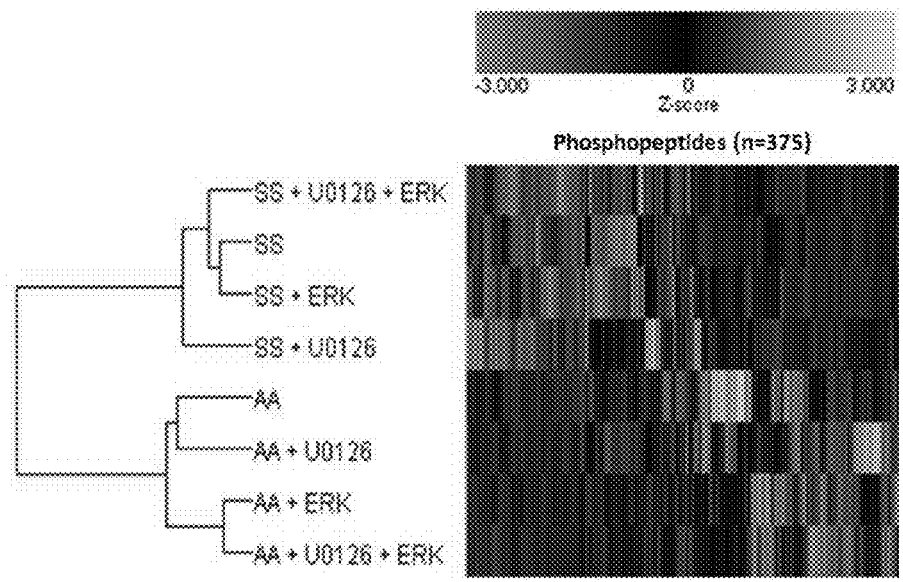
FIG. 15A-15B show two-dimensional (2D) agglomerative cluster analysis of Z-score transformed (i.e., magnitude of significance of change) phosphopeptide intensities across eight unique RBC treatment groups. Person correlations were used as the measure of similarity (−1 dissimilar, +1 identical).
Figure 15B:
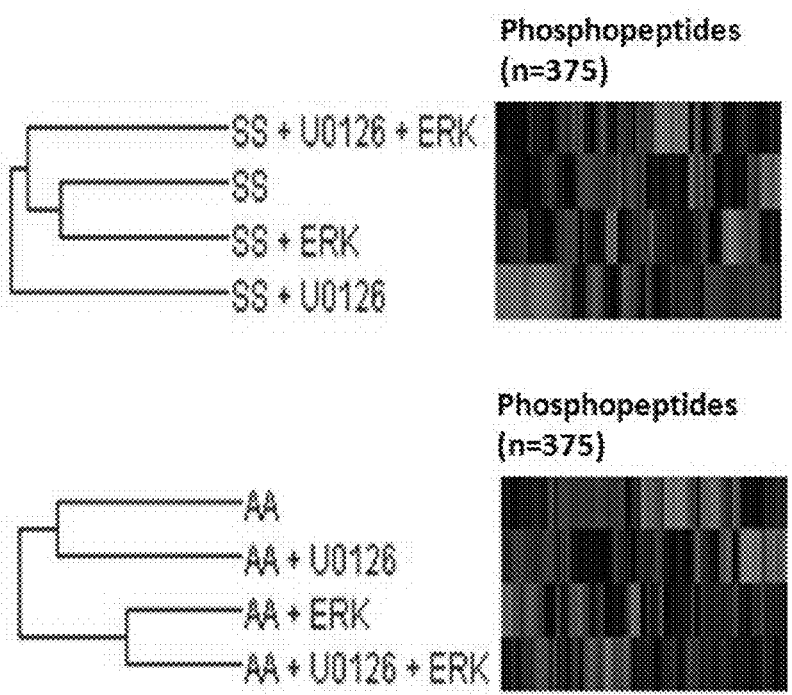

To assess global quantitative differences between all treatment groups, data were subjected to two-dimensional agglomerative clustering of Z-score transformed (i.e. magnitude of significance of change) individual phosphopeptide intensities. This analysis revealed the most significant differentiation (most negative Pearson correlation) across all treatment groups, was the sickle versus healthy red cell phenotype, with 201 phosphopeptides being significantly up-regulated in SS vs AA RBCs at a p-value<0.05 and fold-increase of >1.75 (chosen based on an alpha value corresponding to a 95% confidence interval in a statistical powering calculation). The weight of variation from the sickle state of the RBC (−0.664) was more significant than the addition of exogenous active ERK2 or the inhibition of MEK1/2 activity with the MEK1/2 inhibitor U0126, suggesting that in addition to MEK1/2/ERK1/2 phosphorylation cascades in the SS RBC, other cellular signaling pathway activities are also involved (FIG. 15A). Interestingly, clustering of all phosphopeptides within only the SS RBC samples revealed the strongest differentiating factor was in the presence or absence of U0126 (Pearson correlation, −0.422), which supports the previous observation that ERK1/2 is constitutively hyperactive in these sickle RBCs and inhibiting ERK1/2's upstream activator, MEK1/2, alters a number of signaling events (FIGS. 15A and 15B). Recovery of the U1026 treatment by addition of exogenous active ERK2 resulted in the phosphorylation profile becoming more similar to the sham-treated SS RBCs. In comparison, clustering of all phosphopeptides within only the AA RBC samples revealed the strongest differentiating factor was the addition of exogenous active ERK2 (−0.489), which is consistent with the normal inactivity of ERK1/2 in AA RBCs and suggests that ERK1/2 signaling is indeed mediating downstream phosphorylation of a number of targets (FIGS. 15A and 15B).

Putative downstream targets specific to MEK1/2-dependent activation of ERK1/2 were initially identified comparing individual phosphopeptide intensities between SS RBCs and SS RBCs treated with U0126. The MEK1/2 inhibitor U0126 was able to significantly down-regulate 36 unique RBC membrane phosphopeptides (from 22 unique phosphoproteins) in SS RBCs (Table 3). We analyzed a number of these phosphoproteins referring first to the model of red blood cell membrane functional organization proposed by Anong W A et al. who identified two major protein complexes bridging the RBC membrane to cytoskeleton network: the junctional complex formed by band 3, glycophorin C, Rh group, glucose transporter, dematin, p55, adducin, band 4.1 and 4.2 with associated glycolytic enzymes, and the ankyrin complex formed by band 3, glycophorin A, Rh group, ankyrin, and protein 4.2. Both complexes participate in anchoring the membrane to the actins, and α- and β-spectrins network, involving also other peripheral proteins as tropomyosin and tropomodulin. Here, we found that MEK1/2-dependent ERK1/2 activation in SS RBCs affected membrane-bound proteomes of both the junctional and ankyrin complexes, including dematin, α- and β-adducins, and glycophorin A. Glycophorin A was the most affected protein in SS RBCs by this pathway, which contained 11 unique phosphorylated peptides with 8 unique phosphorylated residues (6 phospho-serines and 2 phospho-threonines). The abundance of 6 of the phosphorylated residues, which was significantly downregulated with U0126 treatment of SS RBCs, was up-regulated in AA RBCs in the presence of exogenous active ERK2, suggesting that increased phosphorylation of glycophorin A by MEK1/2ERK1/2 signaling could potentially affect SS RBC membrane properties. Glycophorin A, is the major sialoglycoprotein, and increased SS RBC adhesion to vascular endothelial cells has been postulated to result from clustering of negatively charged glycophorin-linked sialic acid moieties at the RBC surface. Enhanced SS RBC adhesion may also result from increased phosphorylation of glycophorin A by MEK/1/2/ERK1/2 signaling. In addition, modulation in glycophorin A phosphorylation may also affect glycophorin A interactions with band 3, which could result in decreased in both anion transport by band 3 and band 3 trafficking.

Our data also indicated that adducin-β contained three unique phosphorylated peptides, with phosphorylation of residues within the ERK1/2 consensus motif, suggesting that the cytoskeletal protein adducin-β is a substrate for ERK1/2 in RBCs (Table 3). A significant decrease in phosphorylation of these peptides was observed in U0126-treated SS RBCs, while a significant increase in phosphorylation was observed in both U0126-treated SS RBCs and in AA RBCs when recombinant active ERK2 was added to the membrane ghosts. However, the phosphorylated serine on either adducin-α or dematin, was not within the ERK1/2 consensus motif. Previous studies have shown that rapid phosphorylation of α- and β-adducins by PKC at Ser-726 and Ser-713, respectively, leads to decreased F-actin capping and dissociation of spectrin from actin, implicating adducin phosphorylation in cytoskeletal remodeling. Alternatively, dematin is a substrate for PKC and PKA, and PKA-induced dematin phosphorylation completely abolishes its actin bundling capability. Studies in vitro and in vivo in mice genetically lacking dematin have also shown its important role in maintaining red cell homeostasis and membrane mechanical properties.

TABLE 3

Changes in Phosphorylation of Peptdes in SS and AA RBCs

| Protein Description | Modified Peptide | Fold Change: SS vs SS + U0126 (Relative to SS) | p-value | Fold Change: SS + U0126 vs SS + U0126 + ERK (Relative to SS + U0126) | p-value | Fold Change: AA vs AA + ERK (Relative to AA) | p-value |
|---|---|---|---|---|---|---|---|
| Leucine-zipper-like transcriptional regulator 1 | MAGPGST*GGQIGAAALAGGAR (SEQ ID NO: 8) | -6.48 | 4.50-E02 | 6.70 | 4.54E-06 | | |
| Adenylyl cyclase-associated prtoein 1 | SGPKPFSAPKPQTS*PSPK (SEQ ID NO: 9) | -4.79 | 2.00E-03 | 5.33 | 2.00E-04 | | |
| Dematin | QPLTSPGSVS*PSR (SEQ ID NO: 10) | -4.40 | 1.00E-03 | | | | |
| Alpha-adducin | QKGS*EENLDEAR (SEQ ID NO: 11) | -4.12 | 2.80E-45 | 2.42 | 1.25E-11 | | |
| Protein MICAL-2 | VS*S*GIGAAAEVLVNLY*MNDHRPKAQAT*SPDLESMRK (SEQ ID NO: 12) | -4.06 | 8.44E-05 | | | | |
| facilitated glucose transporter member 1 | QGGAS*QSDKTPEELFHPLGADSQV (SEQ ID NO: 13) | -3.37 | 7.99E-08 | | | | |
| U3 small nucleolar RNA-associated protein 15 | VVHS*FDYAAS*ILSLALAHEDETIVVGMTNGILS*VKHR (SEQ ID NO: 14) | -2.93 | 7.39E-11 | 2.19 | 6.08E-05 | 2.06 | 9.39E-14 |
| Leucine-rich repeats and immunoglobulin-like domains protein 2 | T*HPETIIALRGIVINVLTCTAVSSSDSPMST*VWR (SEQ ID NO: 15) | -2.92 | 1.27E-23 | 1.84 | 2.65E-05 | | |
| Transmembrane protein 151B | SPPGS*AAGES*AAGGGGGGGGPGVSEELTAAAAAAADEGPAR (SEQ ID NO: 16) | -2.85 | 3.91E-05 | | | | |
| Eukaryotic translation initiation factor 4B | SQS*SDTEQQSPTSGGGK (SEQ ID NO: 17) | -2.48 | 4.00E-03 | 1.95 | 2.00E-02 | | |
| Spectrin beta chain, erythrocyte | QIAERPAEETGPQEEEGETAGEAPVS*HHAATER (SEQ ID NO: 18) | -2.42 | 5.77E-04 | | | | |

TABLE 3-continued

Changes in Phosphorylation of Peptdes in SS and AA RBCs

| Protein Description | Modified Peptide | Fold Change: SS vs SS + U0126 (Relative to SS) | p-value | Fold Change: SS + U0126 vs SS + U0126 + ERK (Relative to SS + U0126) | p-value | Fold Change: AA vs AA + ERK (Relative to AA) | p-value |
|---|---|---|---|---|---|---|---|
| Glycophorin-A | KSPSDVKPLPS*PDT*DVP LS*SVEIENPETSDQ (SEQ ID NO: 19) | -2.26 | 5.00E-03 | | | 2.12 | 8.04E-04 |
| Glycophorin-A | SPSDVKPLPSPDTDVPLS* S*VEIENPETSDQV (SEQ ID NO: 20) | -2.18 | 3.00E-03 | | | 2.74 | 7.97E-05 |
| 60S acidic ribosomal protein P2 | KEES*EES*DDDMGFGLFD (SEQ ID NO: 21) | -2.11 | 3.61E-08 | | | | |
| Glycophorin-A | SPSDVKPLPSPDT*DVPLS SVEIENPETSDQ (SEQ ID NO: 22) | -2.00 | 2.59E-21 | | | | |
| Glycophorin-A | S*PS*DVKPLPSPDTDVPL SSVEIENPETS*DQ (SEQ ID NO: 23) | -1.99 | 1.60E-02 | | | 1.87 | 3.10E-02 |
| Glycophorin A | S*PS*DVKPLPSPDTDVPL SSVEIENPETSDQ (SEQ ID NO: 24) | -1.98 | 8.00E-03 | | | | |
| Glycophorin-A | SDSDVKPLPS*PDT*DVPL SSVEIENPETSDQ (SEQ ID NO: 25) | -1.96 | 2.13-07 | | | | |
| Protein Wnt-16 | HERWNCMITAAATTAPMGA SPLFGYELS*SGTK (SEQ ID NO: 26) | -1.95 | 1.90E-02 | | | | |
| UV excision repair protein RAD23 homolog A | EDKS*PSEESAPTTSPESV SGSVPSSGSSGR (SEQ ID NO: 27) | -1.95 | 1.96E-14 | | | 2.19 | 4.13E-32 |
| Glycophorin-A | SPSDVKPLPSPDTDVPLSS VEIENPET*SDQ (SEQ ID NO: 28) | -1.93 | 1.82E-13 | | | | |
| Metabotropic glutamate receptor 7 | LSHKPSDRPNGEAKT*ELC ENVDPNS*PAAK (SEQ ID NO: 29) | -1.91 | 2.95E-09 | | | 2.29 | 7.98E-15 |
| Beta-adducin | ETAPEEPGS*PAKS*APAS *PVQSPAK (SEQ ID NO: 30) | -1.91 | 3.87E-09 | | | 2.36 | 4.21E-06 |
| Glycophorin-A | KS*PSDVKPLPSPDTDVPL SSVEIENPETS*DQ (SEQ ID NO: 31) | -1.88 | 2.10E-02 | | | 1.97 | 5.00E-03 |
| Beta-adducin | TESVTSGPMSPEGSPSKS* PSK (SEQ ID NO: 32) | -1.88 | 3.00E-02 | 1.85 | 3.00E-03 | | |
| Glycophorin-A | SPSDVKPLPSPDTDVPLSS *VEIENPETSDQ (SEQ ID NO: 33) | -1.87 | 3.30E-07 | | | | |
| Lipin-2 | S*GGDETPSQSSDISHVLE TETIFTPSSVK (SEQ ID NO: 34) | -1.86 | 3.37E-04 | | | | |
| Proteasome subunit alpha type-3 | ESLKEEDES*DDDNM (SEQ ID NO: 35) | -1.83 | 5.42E-06 | | | | |

TABLE 3-continued

Changes in Phosphorylation of Peptdes in SS and AA RBCs

| Protein Description | Modified Peptide | Fold Change: SS vs SS + U0126 (Relative to SS) | p-value | Fold Change: SS + U0126 vs SS + U0126 + ERK (Relative to SS + U0126) | p-value | Fold Change: AA vs AA + ERK (Relative to AA) | p-value |
|---|---|---|---|---|---|---|---|
| Beta-adducin | ETAPEEPGSPAKS*APAS*PVQSPAK (SEQ ID NO: 36) | −1.82 | 1.80E-02 | 1.80 | 3.00E-02 | 1.75 | 2.00E-02 |
| E3 ubiquitin-protein ligase UBR4 | T*SPADHGGSVGSESGGSAVDSVAGEHSVSGR (SEQ ID NO: 37) | −1.80 | 1.02E-07 | | | | |
| Spectrin beta chain, erythrocyte | LS*S*SWES*LQPEPSHPY (SEQ ID NO: 38) | −1.80 | 6.00E-03 | | | 4.41 | 4.02E-21 |
| Uncharacterized protein LOC388588 | DGVS*LGAVSST*EEASR (SEQ ID NO: 39) | −1.80 | 4.90E-02 | | | | |
| Glycophorin-A | SPSDVKPLPSPDTDVPLSSVEIENPETS*DQ (SEQ ID NO: 40) | −1.77 | 4.00E-03 | | | | |
| Spectrin beta chain, erythrocyte | LS*SS*WESLQPEPSHPY (SEQ ID NO: 41) | −1.76 | 5.56E-05 | | | 2.02 | 9.30E-11 |
| Uncharacterized protein LOC388588 | DGVS*LGAVS*STEEASR (SEQ ID NO: 42) | −1.76 | 9.99E-05 | | | 2.19 | 2.40E-09 |
| Glycophorin-A | SPSDVKPLPSPDT*DVPLS*SVEIENPETSDQ (SEQ ID NO: 43) | −1.75 | 4.80E-02 | | | | |

*Indicates site of phosphorylation

MEK1/2/ERK1/2 signaling in SS RBCs induced changes within the actins/spectrins network as well, by affecting phosphorylation of β-spectrins (Table 3). Erythrocyte spectrin, the major component of the membrane skeleton, undergoes a number of naturally occurring or pathologically induced posttranslational phosphorylation via a cAMP-dependent protein kinase. $^{32}$P-labeling studies indicate that only the β-subunit of spectrin is phosphorylated in intact erythrocyte, and phosphorylation occurs in a sequential manner where each specific site is completely phosphorylated before the next site is modified with the first phosphorylation event occurring on Ser-2114, followed by Ser-2125, Ser-2123, Ser-2128, Ser-2117, and Ser-2110. However, in situ studies by Manno et al. using intact erythrocyte membranes demonstrated that an increase in β-spectrin phosphorylation by casein kinase I causes a decrease in erythrocyte membrane mechanical stability. In addition, certain leukemia patients with elliptocytosis and poikilocytosis displayed an elevated amount of spectrin dimers coinciding with increased β-spectrin phosphorylation. Our findings are in accordance with these previous studies, and all together strongly suggest that increased phosphorylation of β-spectrin destabilizes tetramer formation and has important in vivo physiological functions. Membrane skeleton also appears to regulate lateral and rotational mobility of band 3 and glycophorin A in the plane of the membrane.

Furthermore and interestingly, label-free proteomic analysis revealed that the peptide metabotropic glutamate receptor 7 (mGlu7) underwent serine phosphorylation at the ERK consensus motif (Table 3). Indeed, studies have also demonstrated that mGluR7 activation occurs via an ERK-dependent mechanism, which increased cofilin activity and F-actin depolymerization. mGLu7 acts as an autoreceptor mediating the feedback inhibition of glutamate release, and prolonged activation of this receptor potentiates glutamate release. Increased phosphorylation of mGlu7 in SS RBCs, could explain the rate of active glutamate transport in these cells, which increases 15-fold over that in normal RBCs. Significant Changes were also observed in the status of leucine-rich repeats and immunoglobulin-like domains protein 2, leucine-zipper-like transcriptional regulator 1, and glucose transporter 1, but only in membrane ghosts prepared from SS RBCs treated with U0126 or after addition of exogenous active ERK2 to these membrane ghosts (Table 3). Changes in the status of these proteins by MEK1/2/ERK1/2 signaling may potentially disturb degradation of misfolded glycoproteins and receptor ubiquitination, and affect protein transcription. Similarly and not surprisingly, ERK1/2 signaling was also found to increase phosphorylated adenylyl cyclase-associated protein 1 (CAP1) only in SS RBCs. CAP1 is known to regulate adenylate cyclase activation to increase cAMP levels under specific environmental conditions. Indeed, basal cAMP levels are much higher in sickle than in healthy RBCs, and cAMP and PKA can act as upstream effectors of MEK1/2/ERK1/2 in SS RBCs. CAPs are also involved in actin binding, SH3 binding, and cell morphology maintenance as well. The failure of recombinant active ERK2 to significantly upregulate the abundance of the phosphorylated peptides, leucine-rich repeats and immunoglobulin-like domains protein 2, leucine-zipper-like transcriptional regulator 1 and CAP1, in healthy RBCs suggests a negative regulatory mechanism might exist in these cells to prevent activation of ERK1/2-dependent phosphorylation of these membrane proteins. PKA for instance, has been shown to exert a negative feedback loop through activation of phosphodiesterases, resulting in cAMP hydrolysis switching off downstream signaling.

ERK1/2 is Involved in Phosphorylation of Glycophorin A.

Figure 16:
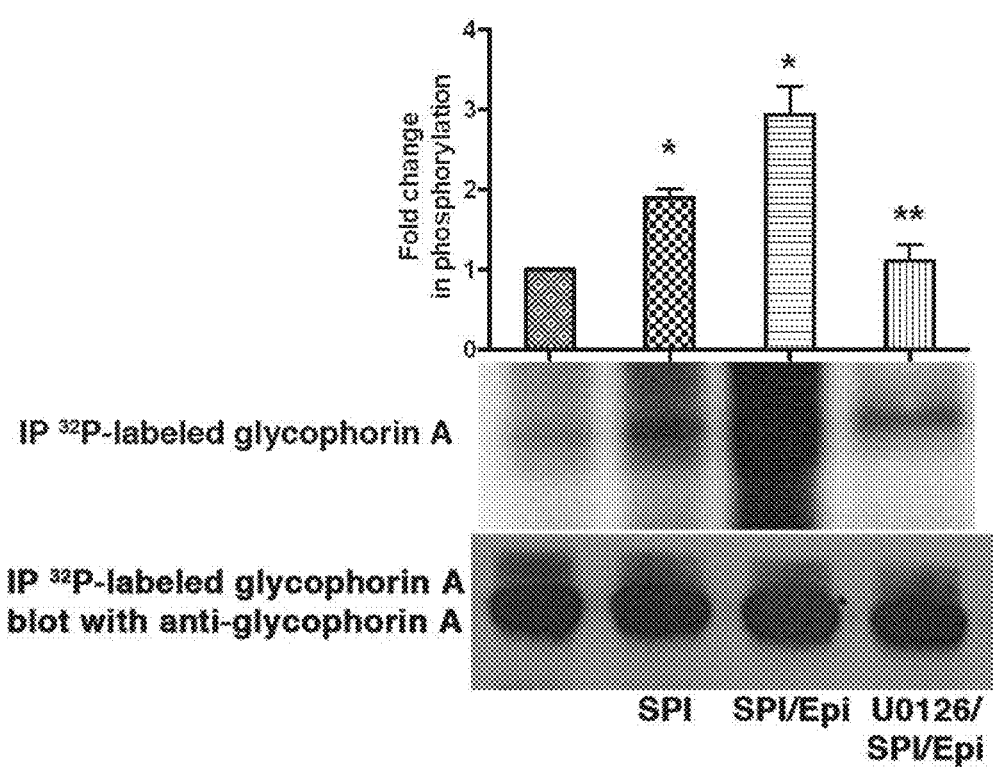
FIG. 16 Shows that ERK1/2 signaling modulates glycophorin A serine phosphorylation. Inorganic $^{32}P$ radiolabeled intact SS RBCs were incubated in the absence (lane 1) or presence (lanes 2, 3 and 4) of serine/threonine protein phosphatase inhibitors (SPI), not followed (lanes 1 and 2) or followed by treatment with epinephrine (epi) (lanes 3 and 4). In lane 4, SS RBCs were preincubated with MEK1/2 inhibitor U0126 prior to treatment with SPI followed by epi treatment. The cpm are representative of three different experiments, calculated by subtraction of cpm present in a lane (not shown) containing immunoprecipitates using immunoglobulin P3 from cpm obtained using anti-glycophorin A mAb for immunoprecipitation under each set of conditions indicated. *: $p<0.05$ and $p<0.001$ for SPI-treated and SPI+epi-treated vs. sham-treated, respectively; **: $p<0.001$ compared to SPI+epi-treated SS RBCs. Total glycophorin A loaded in each lane was detected using nitrocellulose membranes of phosphorylated glycophorin A blotted with anti-glycophorin A mAb. PhosphorImager analysis of immunoprecipitated $^{32}P$-radiolabeled glycophorin A and negative control immune complexes showed that glycophorin A of non-stimulated SS RBCs (FIG. 16, lane 1) is modestly phosphorylated at baseline. Treatment of SS RBCs with serine phosphatase inhibitors (SPI) (lane 2) slightly increased glycophorin A phosphorylation by $1.9\pm0.1$-fold ($p<0.05$, $n=3$), suggesting that increased glycophorin A phosphorylation is a result of serine phosphorylation, as tyrosine phosphatase inhibitors were not present. Epinephrine in the presence of SPI had a stronger effect on glycophorin A phosphorylation ($2.93\pm0.35$-fold increase over sham-treated SS RBCs; $p<0.001$) (lane 3). However, treatment of SS RBCs with the MEK/12 inhibitor U0126 significantly decreased the combined effect of epinephrine and SPI on glycophorin A phosphorylation (lane 4) compared to cells treated with epinephrine and SPI ($p<0.001$) (lane 3).

The pharmacological stress hormone epinephrine can modulate ERK1/2 activation in SS RBCs. Because our proteomics data showed that ERK1/2-induced changes in the phosphorylation state of glycophorin A affected numerous peptides, we determined the contribution of epinephrine-induced increased activation of ERK1/2 signaling in glycophorin A phosphorylation. PhosphorImager analysis of immunoprecipitated $^{32}$P-radiolabeled glycophorin A and negative control immune complexes showed that glycophorin A of non-stimulated SS RBCs (FIG. 16, lane 1) is modestly phosphorylated at baseline. Treatment of SS RBCs with serine phosphatase inhibitors (SPI) (FIG. 16, lane 2) slightly increased glycophorin A phosphorylation by 1.9±0.1-fold (p<0.05, n=3), suggesting that increased glycophorin A phosphorylation is a result of serine phosphorylation, as tyrosine phosphatase inhibitors were not present. Epinephrine in the presence of SPI had a stronger effect on glycophorin A phosphorylation (2.93±0.35-fold increase over sham-treated SS RBCs; p<0.001) (FIG. 16; lane 3). However, treatment of SS RBCs with the MEK/12 inhibitor U0126 significantly decreased the combined effect of epinephrine and SPI on glycophorin A phosphorylation (FIG. 16; lane 4) compared to cells treated with epinephrine and SPI (p<0.001) (FIG. 16; lane 3). Immunoblots of $^{32}$P-radiolabeled glycophorin A immunoprecipitates from stimulated and non-stimulated SS RBCs indicated that a similar amount of glycophorin A was immunoprecipitated from these cells. Our data strongly confirm that increased glycophorin A phosphorylation is dependent on MEK1/2-dependent ERK1/2 signaling pathway in SS RBCs. It has been suggested that glycophorin A contains receptors or other surface recognition sites of the erythrocyte. Although the conformation of glycophorin in the lipid bilayer is not known, it has been suggested that the glycoproteins exist as aggregates in the membrane in order to facilitate receptor function. However, we do not know whether increased phosphorylation of glycophorin A affects the state of aggregation of this glycoprotein. Recently, Shapiro and Marchesi have demonstrated that the site of phosphorylation of glycophorin is located on the cytoplasmic COOH terminal end.[65] It remains to be determined if phosphorylation plays a role in the formation of aggregates of the protein.

Indeed, ERK activation in sickle RBCs not only upregulated sickle red cell adhesion to TNF-α activated endothelial cells in vitro, but affected proteins involved in nitric oxide transport, oxidative stress, proteins of the water channel, maintenance of the integrity of the plasma membrane and to anchor specific ion channels, ion exchangers and ion transporters in the plasma membrane, membrane morphogenesis and cytoskeletal organization, regulation of integrin-mediated signaling, and membrane integrity, permeability and polarity as well (Table 3). The MEK inhibitor U0126 down-regulates phosphorylation of ERK targets. These data suggest that ERK is involved not only in abnormal SS RBC adhesion, but affects multiple other red cell functions related but not limited to oxidative stress, hemolysis and ion transport.

REFERENCES

1. Frenette P S, Atweh G F: Sickle cell disease: old discoveries, new concepts, and future promise, J Clin Invest 2007, 117:850-858

2. Hebbel R P, Boogaerts M A, Eaton J W, Steinberg M H: Erythrocyte adherence to endothelium in sickle-cell anemia. A possible determinant of disease severity, N Engl J Med 1980, 302:992-995

3. Mohandas N, Evans E: Sickle erythrocyte adherence to vascular endothelium. Morphologic correlates and the requirement for divalent cations and collagen-binding plasma proteins, J Clin Invest 1985, 76:1605-1612

4. Zennadi R, Hines P C, De Castro L M, Cartron J P, Parise L V, Telen M J: Epinephrine acts through erythroid signaling pathways to activate sickle cell adhesion to endothelium via LW-alphavbeta3 interactions, Blood 2004, 104:3774-3781

5. Zennadi R, Chien A, Xu K, Batchvarova M, Telen M J: Sickle red cells induce adhesion of lymphocytes and monocytes to endothelium, Blood 2008, 112:3474-3483

6. Zennadi R, Moeller B J, Whalen E J, Batchvarova M, Xu K, Shan S, Delahunty M, Dewhirst M W, Telen M J: Epinephrine-induced activation of LW-mediated sickle cell adhesion and vaso-occlusion in vivo, Blood 2007, 110:2708-2717

7. Schmitt J M, Stork P J: beta 2-adrenergic receptor activates extracellular signal-regulated kinases (ERKs) via the small G protein rap1 and the serine/threonine kinase B-Raf, J Biol Chem 2000, 275:25342-25350

8. Houslay M D, Kolch W: Cell-type specific integration of cross-talk between extracellular signal-regulated kinase and cAMP signaling, Mol Pharmacol 2000, 58:659-668

9. Kolch W: Meaningful relationships: the regulation of the Ras/Raf/MEK/ERK pathway by protein interactions, Biochem J 2000, 351 Pt 2:289-305

10. Brzostowski J A, Kimmel A R: Signaling at zero G: G-protein-independent functions for 7-TM receptors, Trends Biochem Sci 2001, 26:291-297

11. Hall R A, Premont R T, Chow C W, Blitzer J T, Pitcher J A, Claing A, Stoffel R H, Barak L S, Shenolikar S, Weinman E J, Grinstein S, Lefkowitz R J: The beta2-adrenergic receptor interacts with the Na+/H+-exchanger regulatory factor to control Na+/H+ exchange, Nature 1998, 392:626-630

12. Cheung E C, Slack R S: Emerging role for ERK as a key regulator of neuronal apoptosis, Sci STKE 2004, 2004: PE45

13. Fincham V J, James M, Frame M C, Winder S J: Active ERK/MAP kinase is targeted to newly forming cell-matrix adhesions by integrin engagement and v-Src, EMBO J 2000, 19:2911-2923

14. Joslin E J, Opresko L K, Wells A, Wiley H S, Lauffenburger D A: EGF-receptor-mediated mammary epithelial cell migration is driven by sustained ERK signaling from autocrine stimulation, J Cell Sci 2007, 120:3688-3699

15. Park K S, Jeon S H, Kim S E, Bahk Y Y, Holmen S L, Williams B O, Chung K C, Surh Y J, Choi K Y: APC inhibits ERK pathway activation and cellular proliferation induced by RAS, J Cell Sci 2006, 119:819-827

16. Schmidt E K, Fichelson S, Feller S M: PI3 kinase is important for Ras, MEK and Erk activation of Epo-stimulated human erythroid progenitors, BMC Biol 2004, 2:7

17. Bloy C, Blanchard D, Hermand P, Kordowicz M, Sonneborn H H, Cartron J P: Properties of the blood group LW glycoprotein and preliminary comparison with Rh proteins, Mol Immunol 1989, 26:1013-1019

18. Galfre G, Howe S C, Milstein C, Butcher G W, Howard J C: Antibodies to major histocompatibility antigens produced by hybrid cell lines, Nature 1977, 266:550-552

19. Towbin H, Staehelin T, Gordon J: Electrophoretic transfer of proteins from polyacrylamide gels to nitrocellulose sheets: procedure and some applications, Proc Natl Acad Sci USA 1979, 76:4350-4354

20. Udani M, Zen Q, Cottman M, Leonard N, Jefferson S, Daymont C, Truskey G, Telen M J: Basal cell adhesion molecule/lutheran protein. The receptor critical for sickle cell adhesion to laminin, J Clin Invest 1998, 101:2550-2558

21. Brunati A M, Bordin L, Clari G, James P, Quadroni M, Baritono E, Pinna L A, Donella-Deana A: Sequential phosphorylation of protein band 3 by Syk and Lyn tyrosine kinases in intact human erythrocytes: identification of primary and secondary phosphorylation sites, Blood 2000, 96:1550-1557

22. Zamah A M, Delahunty M, Luttrell L M, Lefkowitz R J: Protein kinase A-mediated phosphorylation of the beta 2-adrenergic receptor regulates its coupling to Gs and Gi. Demonstration in a reconstituted system, J Biol Chem 2002, 277:31249-31256

23. Oonishi T, Sakashita K, Uyesaka N: Regulation of red blood cell filterability by Ca2+ influx and cAMP-mediated signaling pathways, Am J Physiol 1997, 273:C1828-1834

24. Crews C M, Alessandrini A, Erikson R L: Erks: their fifteen minutes has arrived, Cell Growth Differ 1992, 3:135-142

25. Lee M H, Klein R L, EI-Shewy H M, Luttrell D K, Luttrell L M: The adiponectin receptors AdipoR1 and AdipoR2 activate ERK1/2 through a Src/Ras-dependent pathway and stimulate cell growth, Biochemistry 2008, 47:11682-11692

26. Yoon M S, Koo J B, Hwang J H, Lee K S, Han J S: Activation of phospholipase D by 8-Br-cAMP occurs through novel pathway involving Src, Ras, and ERK in human endometrial stromal cells, FEBS Lett 2005, 579: 5635-5642

27. Faltynek C R, Schroeder J, Mauvais P, Miller D, Wang S, Murphy D, Lehr R, Kelley M, Maycock A, Michne W, et al.: Damnacanthal is a highly potent, selective inhibitor of p56lck tyrosine kinase activity, Biochemistry 1995, 34:12404-12410

28. Hines P C, Zen Q, Burney S N, Shea D A, Ataga K I, Orringer E P, Telen M J, Parise L V: Novel epinephrine and cyclic AMP-mediated activation of BCAM/Lu-dependent sickle (SS) RBC adhesion, Blood 2003, 101:3281-3287

29. Fukumoto T, Kubota Y, Kitanaka A, Yamaoka G, Ohara-Waki F, Imataki O, Ohnishi H, Ishida T, Tanaka T: Gab1 transduces PI3K-mediated erythropoietin signals to the Erk pathway and regulates erythropoietin-dependent proliferation and survival of erythroid cells, Cell Signal 2009, 21:1775-1783

30. Jindal H K, Ai Z, Gascard P, Horton C, Cohen C M: Specific loss of protein kinase activities in senescent erythrocytes, Blood 1996, 88:1479-1487

31. Shain W, Forman D S, Madelian V, Turner J N: Morphology of astroglial cells is controlled by beta-adrenergic receptors, J Cell Biol 1987, 105:2307-2314

32. Husain-Chishti A, Levin A, Branton D: Abolition of actin-bundling by phosphorylation of human erythrocyte protein 4.9, Nature 1988, 334:718-721

33. Siegel D L, Branton D: Partial purification and characterization of an actin-bundling protein, band 4.9, from human erythrocytes, J Cell Biol 1985, 100:775-785

34. George A, Pushkaran S, Li L, An X, Zheng Y, Mohandas N, Joiner C H, Kalfa T A: Altered phosphorylation of cytoskeleton proteins in sickle red blood cells: the role of protein kinase C, Rac GTPases, and reactive oxygen species, Blood Cells Mol Dis 2010, 45:41-45

35. Ling E, Danilov Y N, Cohen C M: Modulation of red cell band 4.1 function by cAMP-dependent kinase and protein kinase C phosphorylation, J Biol Chem 1988, 263: 2209-2216

36. Zambuzzi W F, Bruni-Cardoso A, Granjeiro J M, Peppelenbosch M P, de Carvalho H F, Aoyama H, Ferreira C V: On the road to understanding of the osteoblast adhesion: cytoskeleton organization is rearranged by distinct signaling pathways, J Cell Biochem 2009, 108:134-14

The invention claimed is:

1. A method of alleviating vaso-occlusion in a patient with the hemoglobinopathy comprising administering an inhibitor selected from an ERK inhibitor, and a Raf inhibitor, wherein the patient has experienced at least one vaso-occlusive event.

2. The method of claim 1, wherein the hemoglobinopathy is selected from the group consisting of sickle cell disease, β-thalassemia, and hemoglobin H disease.

3. The method of claim 2, wherein the hemoglobinopathy is sickle cell disease.

4. The method of claim 1, wherein the subject is human.

5. The method of claim 1, further comprising administering a MEK inhibitor.

6. The method of claim 5, wherein the MEK inhibitor is selected from U0126, PD98059, PD-334581, GDC-0973, CIP-137401, ARRY-162, ARRY-300, PD318088, PD0325901, CI-1040, BMS 777607, AZD8330, AZD6244, AS703026, RDEA119, and GSK1120212.

7. The method of claim 1, wherein the inhibitor is an ERK inhibitor.

8. The method of claim 7, wherein the ERK inhibitor is AEZS-131.

9. The method of claim 1, wherein the inhibitor is a Raf inhibitor.

10. The method of claim 9, wherein the Raf inhibitor is selected from sorafenib tosylate, GDC-0879, PLX-4720, regorafenib, PLX-4032, SB-590885-R, RAF265, GW5074, XL281, and GSK2118436.

11. The method of claim 1, wherein both an ERK inhibitor and a Raf inhibitor are administered.

12. The method of claim 11, further comprising administering a MEK inhibitor.

* * * * *